(12) United States Patent
Kehler et al.

(10) Patent No.: US 11,535,611 B2
(45) Date of Patent: Dec. 27, 2022

(54) PYRAZOLO[3,4-B]PYRIDINES AND IMIDAZO[1,5-B]PYRIDAZINES AS PDE1 INHIBITORS

(71) Applicant: H. Lundbeck A/S, Valby (DK)

(72) Inventors: Jan Kehler, Lyngby (DK); Lars Kyhn Rasmussen, Vanløse (DK); Morten Langgård, Glostrup (DK); Mikkel Jessing, Frederiksberg (DK); Paulo Jorge Vieira Vital, København V (DK); Karsten Juhl, Greve (DK); Mauro Marigo, Skovlunde (DK)

(73) Assignee: H. Lundbeck A/S, Valby (DK)

( * ) Notice: Subject to any disclaimer, the term of this patent is extended or adjusted under 35 U.S.C. 154(b) by 34 days.

(21) Appl. No.: 16/955,926

(22) PCT Filed: Dec. 19, 2018

(86) PCT No.: PCT/EP2018/085725
§ 371 (c)(1),
(2) Date: Jun. 19, 2020

(87) PCT Pub. No.: WO2019/121840
PCT Pub. Date: Jun. 27, 2019

(65) Prior Publication Data
US 2021/0009571 A1    Jan. 14, 2021

(30) Foreign Application Priority Data

Dec. 20, 2017    (DK) .............................. PA201700729

(51) Int. Cl.
*C07D 401/14*    (2006.01)
*C07D 405/14*    (2006.01)

(52) U.S. Cl.
CPC ......... *C07D 405/14* (2013.01); *C07D 401/14* (2013.01)

(58) Field of Classification Search
CPC .................................................. C07D 471/04
See application file for complete search history.

(56) References Cited

U.S. PATENT DOCUMENTS

| | | |
|---|---|---|
| 8,012,936 B2 | 9/2011 | Sigurdsson et al. |
| 8,679,498 B2 | 3/2014 | Lu et al. |
| 8,961,972 B2 | 2/2015 | Lu et al. |
| 10,034,861 B2 | 7/2018 | Kehler et al. |
| 10,351,561 B2 | 7/2019 | Kehler et al. |
| 10,512,632 B2 | 12/2019 | Kehler et al. |
| 10,618,913 B2 | 4/2020 | Juhl et al. |
| 10,689,379 B2 | 6/2020 | Kehler et al. |
| 10,766,893 B2 | 9/2020 | Juhl et al. |
| 10,806,718 B2 | 10/2020 | Kehler et al. |
| 11,026,923 B2 | 6/2021 | Kehler et al. |
| 11,026,924 B2 | 6/2021 | Kehler et al. |
| 2016/0083391 A1 | 3/2016 | Burdi et al. |
| 2016/0083400 A1 | 3/2016 | Burdi et al. |
| 2016/0101173 A1 | 4/2016 | Ma et al. |
| 2018/0000786 A1 | 1/2018 | Kehler et al. |
| 2018/0179200 A1 | 6/2018 | Kehler et al. |
| 2018/0344680 A1 | 12/2018 | Zhang et al. |
| 2018/0359604 A1 | 12/2018 | Chen et al. |
| 2019/0105302 A1 | 4/2019 | Kehler et al. |
| 2019/0185489 A1 | 6/2019 | Juhl et al. |
| 2019/0194189 A1 | 6/2019 | Juhl et al. |
| 2019/0352302 A1 | 11/2019 | Kehler et al. |
| 2020/0129480 A1 | 4/2020 | Kehler et al. |
| 2020/0360343 A1 | 11/2020 | Kehler et al. |
| 2020/0375950 A1 | 12/2020 | Kehler et al. |
| 2020/0385372 A1 | 12/2020 | Kehler et al. |
| 2020/0385381 A1 | 12/2020 | Kehler et al. |
| 2021/0015794 A1 | 1/2021 | Kehler et al. |
| 2021/0023056 A1 | 1/2021 | Kehler et al. |

FOREIGN PATENT DOCUMENTS

| | | |
|---|---|---|
| CN | 1980927 A | 6/2007 |
| RU | 2402549 C2 | 10/2010 |
| RU | 2397160 C9 | 10/2012 |

(Continued)

OTHER PUBLICATIONS

International Search Report and Written Opinion dated Aug. 25, 2017 for Application No. PCT/EP2017/066255.
International Search Report and Written Opinion dated Feb. 7, 2018 for Application No. PCT/EP2017/083721.
International Search Report and Written Opinion dated Feb. 13, 2019 for Application No. PCT/EP2018/085798.
International Search Report and Written Opinion dated Feb. 11, 2019 for Application No. PCT/EP2018/085728.
International Search Report and Written Opinion dated Mar. 6, 2019 for Application No. PCT/EP2018/085725.
International Search Report and Written Opinion dated Apr. 16, 2019 for Application No. PCT/EP2018/084432.
International Search Report and Written Opinion dated Apr. 16, 2019 for Application No. PCT/EP2018/084434.

(Continued)

*Primary Examiner* — Erich A Leeser
(74) *Attorney, Agent, or Firm* — Wolf, Greenfield & Sacks, P.C.

(57) ABSTRACT

The present invention provides compounds of formula (I) that are PDE1 enzyme inhibitors and their use as a medicament, in particular for the treatment of neurodegenerative disorders and psychiatric disorders. The present invention also provides pharmaceutical compositions comprising compounds of the invention and methods of treating disorders using the compounds of the invention.

9 Claims, No Drawings

(56) References Cited

FOREIGN PATENT DOCUMENTS

| WO | WO 00/15222 A1 | 3/2000 | |
|---|---|---|---|
| WO | WO 01/18004 A2 | 3/2001 | |
| WO | WO 03/15812 A2 | 2/2003 | |
| WO | WO 2004/056823 A1 | 7/2004 | |
| WO | WO 2006/004188 A1 | 1/2006 | |
| WO | WO 2006/044821 A1 | 4/2006 | |
| WO | WO 2006/112464 A1 | 10/2006 | |
| WO | WO 2007/071311 A1 | 6/2007 | |
| WO | WO 2008/070095 A1 | 6/2008 | |
| WO | WO 2008/111010 A1 | 9/2008 | |
| WO | WO 2010/065153 A1 | 6/2010 | |
| WO | WO 2010/144711 A2 | 12/2010 | |
| WO | WO 2012/021469 A1 | 2/2012 | |
| WO | WO 2012/136552 A1 | 10/2012 | |
| WO | WO 2012/143143 A1 | 10/2012 | |
| WO | WO 2013/142307 A1 | 9/2013 | |
| WO | WO 2014/170248 A1 | 4/2014 | |
| WO | WO 2015/004007 A1 | 1/2015 | |
| WO | WO 2015/124576 A1 | 8/2015 | |
| WO | WO 2016/042775 A1 | 3/2016 | |
| WO | WO 2016/043997 A1 | 3/2016 | |
| WO | WO 2016/055618 A1 | 4/2016 | |
| WO | WO 2016/075062 A1 | 5/2016 | |
| WO | WO 2016/075063 A1 | 5/2016 | |
| WO | WO 2016/075064 A1 | 5/2016 | |
| WO | WO 2016/147659 A1 | 9/2016 | |
| WO | WO 2016/170064 A1 | 10/2016 | |
| WO | WO 2017/009308 A2 | 1/2017 | |
| WO | WO 2017/024004 A1 | 2/2017 | |
| WO | WO 2017/025559 A1 | 2/2017 | |
| WO | WO 2017/172795 A1 | 10/2017 | |
| WO | WO 2018/007249 A1 | 1/2018 | |
| WO | WO 2019/115566 A1 | 6/2019 | |
| WO | WO-2019115567 A1 * | 6/2019 | ........... C07D 413/14 |

OTHER PUBLICATIONS

Bakker et al., Reduction of hippocampal hyperactivity improves cognition in amnestic mild cognitive impairment. Neuron. May 10, 2012;74(3):467-74.

Bernard et al., Transcriptional architecture of the primate neocortex. Neuron. Mar. 22, 2012;73(6):1083-99.

Blokland et al., PDE Inhibition and Cognition Enhancement. Expert Opinion Thera. Patents. Apr. 2012; 22(4):349-354.

Butchart et al., Etanercept in Alzheimer disease: A randomized, placebo-controlled, double-blind, phase 2 trial. Neurology. May 26, 2015;84(21):2161-8. Epub May 1, 2015. Erratum in: Neurology. Dec. 8, 2015;85(23):2084.

Davtyan et al., Immunogenicity, efficacy, safety, and mechanism of action of epitope vaccine (Lu AF20513) for Alzheimer's disease: prelude to a clinical trial. J Neurosci. Mar. 13, 2013;33(11):4923-34.

Francis et al., Mammalian cyclic nucleotide phosphodiesterases: molecular mechanisms and physiological functions. Physiol Rev. Apr. 2011;91(2):651-90.

Hampel et al., Beta-site amyloid precursor protein cleaving enzyme 1 (BACE1) as a biological candidate marker of Alzheimer's disease. Scand J Clin Lab Invest. Feb. 2009;69(1):8-12.

Jacobsen et al., Combined treatment with a BACE inhibitor and anti-Aβ antibody gantenerumab enhances amyloid reduction in APPLondon mice. J Neurosci. Aug. 27, 2014;34(35):11621-30.

Koh et al., Treatment strategies targeting excess hippocampal activity benefit aged rats with cognitive impairment. Neuropsychopharmacology. Mar. 2010;35(4):1016-25. Epub Dec. 23, 2009.

Li et al., A highly effective one-pot synthesis of quinolines from o-nitroarylcarbaldehydes. Organic & Biomolecular Chemistry. Jan. 2007;5(1):61-4. Epub Nov. 6, 2006.

Medina, Therapeutic Utility of Phosphodiesterase Type I Inhibitors in Neurological Conditions. Front Neurosci. Feb. 2011;5:21. 5 pages.

Saito et al., Pyrrolo[1,2-b]pyridazines, pyrrolo[2,1-f]triazin-4(3H)-ones, and related compounds as novel corticotropin-releasing factor 1 ($CRF_1$) receptor antagonists. Bioorg Med Chem. Jan. 15, 2012;20(2):1122-38. Epub Dec. 3, 2011.

Seeman, Atypical antipsychotics: mechanism of action. Can J Psychiatry. Feb. 2002;47(1):29-40.

Shi et al., Antiepileptics topiramate and levetiracetam alleviate behavioral deficits and reduce neuropathology in APPswe/PS1dE9 transgenic mice. CNS Neurosci Ther. Nov. 2013;19(11):871-81. Epub Jul. 27, 2013.

Yamamoto et al., The effects of a novel phosphodiesterase 7A and -4 dual inhibitor, YM-393059, on T-cell-related cytokine production in vitro and in vivo. Eur J Pharmacol. Jul. 10, 2006;541(1-2):106-14.

Mironov, The Guidelines for Conducting Preclinical Studies of Micaments. Grif & Co. Moscow, Russia. 2012. 941 pages.

* cited by examiner

PYRAZOLO[3,4-B]PYRIDINES AND IMIDAZO[1,5-B]PYRIDAZINES AS PDE1 INHIBITORS

CROSS REFERENCE TO RELATED APPLICATIONS

This Application is a National Stage filing under 35 U.S.C. 371 of International Patent Application No. PCT/EP2018/085725, filed Dec. 19, 2018, which claims foreign priority benefits are claimed under 35 U.S.C. § 119(a)-(d) or 35 U.S.C. § 365(b) of Denmark Application Number PA201700729, filed Dec. 20, 2017. The entire contents of these applications are incorporated herein by reference in their entirety.

FIELD OF THE INVENTION

The present invention provides compounds that are PDE1 enzyme inhibitors and their use as medicaments, in particular for the treatment of neurodegenerative disorders and psychiatric disorders. The present invention also provides pharmaceutical compositions comprising compounds of the invention and methods of treating disorders using the compounds of the invention.

BACKGROUND OF THE INVENTION

The second messenger cyclic Nucleotides (cNs), cyclic adenosine monophosphate (cAMP) and cyclic guanosine monophosphate (cGMP) play a major role in intracellular signal transduction cascade, by regulating cN-dependent protein kinases (PKA and PKG), EPACs (Exchange Protein Activated by cAMP), phosphoprotein phosphatases, and/or cN-gated cation channels. In neurons, this includes the activation of cAMP- and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by phosphodiesterases (PDEs, EC 3.1.4.17). PDEs are bimetallic hydrolases that inactivate cAMP/cGMP by catalytic hydrolysis of the 3'-ester bond, forming the inactive 5'-monophosphate. Since PDEs provide the only means of degrading the cyclic nucleotides cAMP and cGMP in cells, PDEs play an essential role in cyclic nucleotide signalling. The catalytic activities of PDEs provide for breakdown of cNs over a spectrum of cN-concentrations in all cells, and their varied regulatory mechanisms provide for integration and crosstalk with myriads of signalling pathways. Particular PDEs are targeted to discrete compartments within cells where they control cN level and sculpt microenvironments for a variety of cN signalosomes (Sharron H. Francis, Mitsi A. Blount, and Jackie D. Corbin. Physiol Rev 2011, 91: 651-690).

On the basis of substrate specificity, the PDE families can be divided into three groups: 1) The cAMP-specific PDEs, which include PDE4, PDE7, and PDE8, 2) the cGMP-selective enzymes PDE5 and PDE9, and 3) the dual-substrate PDEs, PDE1, PDE2, PDE3, as well as PDE10 and PDE11.

Previously named calmodulin-stimulated PDE (CaM-PDE), PDE1 is unique in that it is $Ca^{2+}$-dependently regulated via calmodulin (CaM, a 16 kDa $Ca^{2+}$-binding protein) complexed with four $Ca^{2+}$ (for review, Sharron H. Francis, Mitsi A. Blount, and Jackie D. Corbin. Physiol Rev 2011, 91: 651-690). Thus, PDE1 represents an interesting regulatory link between cyclic nucleotides and intracellular $Ca^{2+}$. The PDE1 family is encoded by three genes: PDE1A (mapped on human chromosome 2q32), PDE1B (human chromosome location, hcl: 12q13) and PDE1C (hcl: 7p14.3). They have alternative promoters and give rise to a multitude of proteins by alternative splicing which differ in their regulatory properties, substrate affinities, specific activities, activation constants for CaM, tissue distribution and molecular weights. More than 10 human isoforms are identified. Their molecular weights vary from 58 to 86 kDa per monomer. The N-terminal regulatory domain contains two $Ca^{2+}$/CaM binding domains and two phosphorylation sites and different splice variants have different variations of the N-terminal domain, which can give proteins with different amino acid sequence with different biochemical functions. PDE1 is a dual substrate PDE and the PDE1C-subtype has equal activity towards cAMP and cGMP (Km≈1-3 µM), whereas the subtypes PDE1A and PDE1B have a preference for cGMP (Km for cGMP≈1-3 µM and for cAMP≈10-30 µM).

The PDE1 subtypes are highly enriched in the brain and located especially in the striatum (PDE1B), hippocampus (PDE1A) and cortex (PDE1A) and this localization is conserved across species (Amy Bernard et al. Neuron 2012, 73, 1083-1099). In the cortex, PDE1A is present mainly in deep cortical layers 5 and 6 (output layers), and used as a specificity marker for the deep cortical layers. PDE1 inhibitors enhance the levels of the second messenger cNs leading to enhanced neuronal excitability.

Thus, PDE1 is a therapeutic target for regulation of intracellular signalling pathways, preferably in the nervous system and PDE1 inhibitors can enhance the levels of the second messenger's cAMP/cGMP leading to modulation of neuronal processes and to the expression of neuronal plasticity-related genes, neurotrophic factors, and neuroprotective molecules. These neuronal plasticity enhancement properties together with the modulation of synaptic transmission make PDE1 inhibitors good candidates as therapeutic agents in many neurological and psychiatric conditions. The evaluation of PDE1 inhibitors in animal models (for reviews see e.g. Blokland et al. Expert Opinion on Therapeutic Patents (2012), 22(4), 349-354; and Medina, A. E. Frontiers in Neuropharmacology (2011), 5 (February), 21) has suggested the potential for the therapeutic use of PDE1 inhibitors in neurological diseases, like e.g. Alzheimer's, Parkinson's and Huntington's Diseases and in psychiatric disorders like e.g. Attention Deficit Hyperactivity Disorder (ADHD), depression, anxiety, narcolepsy, cognitive impairment and cognitive impairment associated with schizophrenia (CIAS) and in restless leg syndrome. There have also been patent applications claiming that PDE1 inhibitors are useful in diseases that may be alleviated by the enhancement of progesterone-signalling such as female sexual dysfunction (e.g. WO 2008/070095).

Various chemical structures with PDE1 inhibiting activity have been identified. WO 2016/055618 discloses triazolopyrazinones as PDE1 inhibitors; WO 2016/042775, US 2016/0083391 and US 2016/0083400 disclose tricyclic lactams as PDE1 inhibitors; WO 2016/147659 and WO 2016/170064 discloses imidazotriazinones as PDE1 inhibitors; and WO 2016/174188 discloses imidiazopyrazinones as PDE1 inhibitors.

Current treatments for neurodegenerative and/or psychiatric disorders are not efficacious in all patients. Hence, there remains a need for alternative methods of treatment of such diseases and for this purpose PDE1 inhibitors may be a good alternative. The present invention discloses new pyrazolo[3,4-b]pyridines and imidazo[1,5-b]pyridazines with PDE1 inhibitor activity and good physicochemical properties as alternatives to known PDE1 inhibitors.

SUMMARY OF THE INVENTION

PDE1 enzymes are expressed in the Central Nervous System (CNS), making this gene family an attractive source of new targets for the treatment of psychiatric and neurodegenerative disorders.

Accordingly, the present invention relates to a compound according to formula (I)

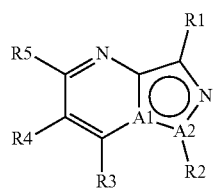

wherein
A1=C, A2=N and R3=—NR6R7, or
A1=C, A2=N and R3=H, or
A1=N, A2=C and R3=H;
R1 is selected from the group consisting of hydrogen, linear or branched $C_{1-4}$ alkyl and $C_{3-4}$ cycloalkyl, wherein said linear or branched $C_{1-4}$ alkyl and $C_{3-4}$ cycloalkyl can optionally be substituted with one or more halogen;
R2 is selected from the group consisting of linear or branched $C_{1-6}$ alkyl, saturated monocyclic $C_{3-6}$ cycloalkyl, oxetanyl, tetrahydrofuranyl and tetrahydropyranyl, wherein said linear or branched $C_{1-6}$ alkyl and saturated monocyclic $C_{3-6}$ cycloalkyl can optionally be substituted with one or more halogen, and wherein said oxetanyl, tetrahydrofuranyl and tetrahydropyranyl can be optionally substituted one or more times with a substituent selected from methyl and halogen;
R4 is selected from the group consisting of hydrogen, linear or branched $C_{1-4}$ alkyl and $C_{3-4}$ cycloalkyl, wherein said linear or branched $C_{1-4}$ alkyl and $C_{3-4}$ cycloalkyl can optionally be substituted with one or more halogen;
R5 is a phenyl, which can be substituted one or more times with one or more substituents selected from $C_{1-4}$ alkoxy, —CH$_2$—$C_{1-4}$alkoxy and —CN wherein said $C_{1-4}$ alkoxy and —CH$_2$—$C_{1-4}$ alkoxy can be optionally substituted with one or more halogen; or
R5 is selected from the group consisting of benzo[1,3]dioxoleyl or 2,3-dihydrobenzo[b][1,4]dioxinyl; or
R5 is a 5-6 membered heteroaryl which can be substituted one or more times with one or more substituents selected from $C_{1-4}$ alkoxy, —CH$_2$—$C_{1-4}$ alkoxy, —CN, linear or branched $C_{1-4}$ alkyl and $C_{3-4}$ cycloalkyl, wherein said linear or branched $C_{1-4}$ alkyl, said $C_{3-4}$ cycloalkyl, said $C_{1-4}$ alkoxy and said —CH$_2$—$C_{1-4}$alkoxy can optionally be substituted with one or more halogen; or
R5 is a 9-membered bicyclic heteroaryl which can be substituted one or more times with one or more substituents selected from $C_{1-4}$ alkoxy, —CH$_2$—$C_{1-4}$alkoxy, —CN, linear or branched $C_{1-4}$ alkyl and $C_{3-4}$ cycloalkyl, wherein said linear or branched $C_{1-4}$ alkyl, said $C_{3-4}$ cycloalkyl, said $C_{1-4}$ alkoxy and said —CH$_2$—$C_{1-4}$alkoxy can optionally be substituted with one or more halogen;

R6 is selected from the group consisting of hydrogen, linear or branched $C_{1-6}$ alkyl and $C_{3-6}$ cycloalkyl, wherein said linear or branched $C_{1-6}$ alkyl and $C_{3-6}$ cycloalkyl can be optionally substituted with one or more fluorine; and R7 is selected from the group consisting of hydrogen, linear or branched $C_{1-6}$ alkyl, $C_{3-6}$ cycloalkyl, oxetanyl, tetrahydrofuranyl, tetrahydropyranyl, —CH$_2$-oxetanyl, —CH$_2$-tetrahydrofuranyl, —CH$_2$-tetrahydropyranyl and —CH$_2$-pyrrolidinyl, wherein said linear or branched $C_{1-6}$ alkyl, $C_{3-6}$ cycloalkyl, oxetanyl, tetrahydrofuranyl, tetrahydropyranyl, —CH$_2$-oxetanyl, —CH$_2$-tetrahydrofuranyl, —CH$_2$— tetrahydropyranyl and CH$_2$-pyrrolidinyl-2-one can be optionally substituted with one or more substituents selected from methyl, methoxy, ethoxy, oxo and fluorine; or
R6 and R7 are connected to form a 5-7 membered saturated heterocyclic ring with the nitrogen atom to which they are attached and 4-6 carbon atoms; wherein said heterocyclic ring can be optionally substituted with one or more substituents selected from methoxy, methyl and fluorine;
or a pharmaceutically acceptable salt thereof;
with the proviso that said compound is not one of the following two compounds or a salt thereof:
1H-Pyrazolo[4,3-b]pyridine, 3-(1,1-dimethylethyl)-1-methyl-5-phenyl-; and
1H-Pyrazolo[4,3-b]pyridine, 5-(3-pyridinyl)-1-(tetrahydro-2H-pyran-2-yl)-.

Reference to compounds of the present invention includes the free base and pharmaceutically acceptable salts of the compounds, such as acid addition salts of the compounds, racemic mixtures of the compounds, or the corresponding enantiomer and/or optical isomer of the compounds for which this is relevant, and polymorphic and amorphic forms of compounds of the present invention and of pharmaceutically acceptable salts of said compounds, as well as tautomeric forms the compounds for which this is relevant. Furthermore, the compounds of the present invention and pharmaceutically acceptable salts thereof may potentially exist in unsolvated as well as in solvated forms with pharmaceutically acceptable solvents such as water, ethanol and the like. Both solvated and unsolvated forms of the compounds and pharmaceutically acceptable salts thereof are encompassed by the present invention.

In one embodiment, the invention relates to a compound according to formula (I) for use in therapy.

In one embodiment, the invention relates to a compound according to formula (I), for use in the treatment of a neurodegenerative disorder, selected from the group consisting of Alzheimer's Disease, Parkinson's Disease and Huntington's Disease or for use in the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

In one embodiment, the invention relates to a pharmaceutical composition comprising a compound according formula (I), and one or more pharmaceutically acceptable carrier or excipient.

In one embodiment, the invention relates to a method for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome, which method comprises the administration of a therapeutically effective amount of a compound according to formula (I) to a patient in need thereof.

In one embodiment, the invention relates to the use of a compound according to formula (I), in the manufacture of a medicament for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

DEFINITIONS

PDE1 Enzymes:

The PDE1 isozyme family includes numerous splice variant PDE1 isoforms. It has three subtypes, PDE1A, PDE1B and PDE1C which divide further into various isoforms. In the context of the present invention PDE1 and PDE1 enzymes are synonymous and refer to PDE1A, PDE1B and PDE1C enzymes as well as their isoforms unless otherwise specified.
PDE1 Inhibitors:

In the context of the present invention, a compound is considered to be a PDE1 inhibitor if the amount required to reach the IC50 level of one or more of the three PDE1 isoforms is 10 micro molar or less, such as less than 9 micro molar, such as 8 micro molar or less, such as 7 micro molar or less, such as 6 micro molar or less, such as 5 micro molar or less, such as 4 micro molar or less, such as 3 micro molar or less. For preferred compounds of the invention the required amount of PDE1 inhibitor required to reach the IC50 level is 2 micro molar or less, such as 1 micro molar or less, in particular 500 nM or less.

Preferred compounds of the invention exhibit selectivity towards the PDE1B isoform meaning that said compounds are stronger as PDE1B inhibitors than as PDE1A and/or PDE1C inhibitors. In preferred embodiments, said compounds are at least two-fold stronger, three-fold stronger, four-fold stronger or five-fold stronger as PDE1B inhibitors than as PDE1A and/or PDE1C inhibitors. In preferred embodiments, the required amount of PDE1 inhibitor required to reach the IC50 level of PDE1B is 400 nM or less, such as 300 nM or less, 200 nM or less, 100 nM or less, or 50 nM or less, for example 25 nM or less. Selectivity towards the PDE1B isoform may prevent potentially unwanted effects associated with PDE1A and/or PDE1C inhibition.
Substituents:

In the present context, "optionally substituted" means that the indicated moiety may or may not be substituted, and when substituted it is mono-, di-, or tri-substituted. It is understood that where no substituents are indicated for an "optionally substituted" moiety, then the position is held by a hydrogen atom.

As used in the context of the present invention, the terms "halo" and "halogen" are used interchangeably and refer to fluorine, chlorine, bromine or iodine. In a preferred embodiment, halogen refers to fluorine.

A given range may interchangeably be indicated with "-" (dash) or "to", e.g. the term "$C_{1-4}$ alkyl" is equivalent to "$C_1$ to $C_4$ alkyl".

The terms "$C_{1-3}$ alkyl", "$C_{1-4}$ alkyl", "$C_{1-5}$ alkyl" and "$C_{1-6}$ alkyl" refer to a linear (i.e. unbranched) or branched saturated hydrocarbon having from one up to 3, 4, 5, or 6 carbon atoms, inclusive. Examples of such groups include, but are not limited to, methyl, ethyl, 1-propyl, 2-propyl, 1-butyl, 2-butyl, 2-methyl-2-propyl, 2-methyl-1-butyl, n-hexyl.

The term "$C_{1-6}$alkoxy" refers to a moiety of the formula —OR', wherein R' indicates $C_{1-6}$ alkyl as defined above.

The term "$C_{3-6}$ cycloalkyl" refers is a saturated monocyclic ring selected from cyclopropyl, cyclobutyl, cyclopentyl and cyclohexyl.

The term "5-6 membered heteroaryl" refers to a 5 to 6 membered aromatic monocyclic ring containing 1 to 6 carbon atoms and one or more heteroatoms selected from oxygen, nitrogen and sulfur. In a preferred embodiment, said 5-6 membered heteroaryl is a 6 membered heteroaryl. Particular mention is made of pyridyl and pyrimidyl.

The term "9 membered heteroaryl" refers to a 9 membered aromatic bicyclic ring containing 4 to 8 carbon atoms and one or more heteroatoms selected from oxygen, nitrogen and sulfur. Particular mention is made of 1H-pyrazolo[1,5-a]pyridine.

The term "5-7 membered saturated heterocyclic ring" refers to a 5, 6 or 7-membered saturated monocyclic ring, containing one nitrogen and optionally one or more additional heteroatoms selected from oxygen, nitrogen and sulfur and at least three carbon atoms. Particular mention is made of pyrrolidinyl.
Isomeric and Tautomeric Forms Where compounds of the present invention contain one or more chiral centers reference to any of the compounds will, unless otherwise specified, cover the enantiomerically or diastereomerically pure compound as well as mixtures of the enantiomers or diastereomers in any ratio.

When a compound of the invention is denoted with the suffix "enantiomer 1" or "enantiomer 2" it is understood that said enantiomer could be either the S-enantiomer or the R-enantiomer. I.e. "enantiomer 1" could be either the S-enantiomer or the R-enantiomer and "enantiomer 2" could be either the S-enantiomer or the R-enantiomer. When both enantiomer 1 and enantiomer 2 have been exemplified for a compound it follows that one is the S-enantiomer and the other is the R-enantiomer.

The absolute stereochemistry for a compound of the invention can be determined by X-ray crystallography or vibrational circular dichroism.

Furthermore, some of the compounds of the present invention may exist in different tautomeric forms and it is intended that any tautomeric forms that the compounds are able to form are included within the scope of the present invention.
Pharmaceutically Acceptable Salts:

The compounds of this invention are generally utilized as the free substance or as a pharmaceutically acceptable salt thereof. When a compound of formula (I) contains a free base, such salts are prepared in a conventional manner by treating a solution or suspension of a free base of formula (I) with a molar equivalent of a pharmaceutically acceptable acid. Representative examples of suitable organic and inorganic acids are described below.

Pharmaceutically acceptable salts in the present context is intended to indicate non-toxic, i.e. physiologically acceptable salts. The term pharmaceutically acceptable salts includes salts formed with inorganic and/or organic acids such as hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, salicylic acid, saccharin and sulfonic acids, such as methanesulfonic acid, ethanesulfonic acid, toluenesulfonic acid and benzenesulfonic acid. Some of the acids listed above are di- or tri-acids, i.e. acids containing two or three acidic hydrogens, such as phosphoric acid, sulphuric acid, fumaric acid and maleic acid.

Additional examples of useful acids and bases to form pharmaceutically acceptable salts can be found e.g. in Stahl and Wermuth (Eds) "Handbook of Pharmaceutical salts. Properties, selection, and use", Wiley-VCH, 2008.

Therapeutically Effective Amount:

In the present context, the term "therapeutically effective amount" of a compound means an amount sufficient to alleviate, arrest, partly arrest, remove or delay the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

Treatment and Treating:

In the present context, "treatment" or "treating" is intended to indicate the management and care of a patient for the purpose of alleviating, arresting, partly arresting, removing or delaying progress of the clinical manifestation of the disease. The patient to be treated is preferably a mammal, in particular a human being.

Combinations

In one embodiment of the invention, the compound of formula (I) is for use as stand-alone treatment as the sole active compound.

In another embodiment of the invention, the compound of formula (I) may be used in combination with a second compound, wherein said second compound is selected from the following: a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody.

In yet another embodiment of the invention, the compound of formula (I) may be used in combination with a second compound, wherein said second compound is a compound that is useful in the treatment of a psychiatric disorder.

The terms "combined use", "in combination with" and "a combination of" and the like as used herein in the context of the method of the invention comprising the combined administration of therapeutically effective amounts of a compound of formula (I), and another pharmaceutically active compound, is intended to mean the administration of a compound of formula (I) simultaneously or sequentially, in any order, together with said second compound.

The two compounds may be administered simultaneously or with a time gap between the administrations of the two compounds. The two compounds may be administered either as part of the same pharmaceutical formulation or composition, or in separate pharmaceutical formulations or compositions. The two compounds may be administered on the same day or on different days. They may be administered by the same route, such for example by oral administration, by depot, by intramuscular injection or intravenous injection; or by different routes wherein one compound is for example administered orally or placed by depot and the other compound is for example injected. The two compounds may be administered by the same dosage regime or interval, such as once or twice daily, weekly, or monthly; or by different dosage regimes for example wherein one is administered once daily and the other is administered twice daily or weekly or monthly.

In some instances, the patient to be treated may already be in treatment with one or more of said second compound when treatment with a compound of formula (I) is initiated. In other instances, the patient may already be in treatment with a compound of formula (I) when treatment with one or more of said second compound is initiated. In other instances, the treatment with a compound of formula (I) and treatment with one or more of said second compound is initiated at the same time.

Compounds for Combination Treatment

In the context of the invention, compounds to be used in combination with a compound of formula (I) in the treatment of a neurodegenerative disorder, is selected from for example a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody. In the context of the invention, compounds to be used in combination with a compound of formula (I) in the treatment of a psychiatric and/or cognitive disorder, is a compound with a pharmacological activity selected from one or more of the following mechanisms: antagonist/inverse agonist/negative modulator/partial agonist/inhibitor of one or more of the targets dopamine D1 receptor, dopamine D2 receptor, dopamine D3 receptor, phosphodiesterase PDE10, serotonin 5-HT2A receptor, serotonin 5-HT6 receptor, and glycine transporter GlyT1; or agonist/positive modulator/partial agonist of one or more of the targets KCNQ channels, NMDA receptor, AMPA receptor and nicotinic alpha-7 receptor. Examples of such compounds includes clozapine, risperidone, paliperidone, olanzapine, quetiapine, amisulpride, ziprasidone, aripiprazole, brexpiprazole, asenapine, haloperidole, iloperidone, lurasidone, chlorpromazine, blonanserin, perphenazine, levomepromazine, sulpiride, fluphenazine, zuclopenthixol, flupenthixol and cariprazine.

Administration Routes

The pharmaceutical compositions comprising a compound of the present invention either as the sole active compound or in combination a second compound defined above, may be specifically formulated for administration by any suitable route such as the oral, rectal, nasal, buccal, sublingual, transdermal and parenteral (e.g. subcutaneous, intramuscular, and intravenous) route; the oral route being preferred.

It will be appreciated that the route will depend on the general condition and age of the subject to be treated, the nature of the condition to be treated and the active ingredient.

Pharmaceutical Formulations and Excipients

In the following, the term, "excipient" or "pharmaceutically acceptable excipient" refers to pharmaceutical excipients including, but not limited to, fillers, antiadherents, binders, coatings, colours, disintegrants, flavours, glidants, lubricants, preservatives, sorbents, sweeteners, solvents, vehicles and adjuvants.

The present invention also provides a pharmaceutical composition comprising a compound of formula (I), such as one of the compounds disclosed in the Experimental Section herein. The present invention also provides a process for making a pharmaceutical composition comprising a compound of formula (I). The pharmaceutical compositions according to the invention may be formulated with pharmaceutically acceptable excipients in accordance with conventional techniques such as those disclosed in Remington, "The Science and Practice of Pharmacy", 22$^{th}$ edition (2012), Edited by Allen, Loyd V., Jr.

Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an orodispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose. If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is requisite that the excipients used for any pharmaceutical formulation comply with the intended route of administration and are compatible with the active ingredients.

Doses:

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 0.1-1000 mg/day of a compound of the present invention, such as 1-500 mg/day, such as 1-100 mg/day or 1-50 mg/day. Conveniently, the compounds of the invention are administered in a unit dosage form containing said compounds in an amount of about 0.1 to 500 mg, such as 10 mg, 50 mg 100 mg, 150 mg, 200 mg or 250 mg of a compound of the present invention.

DETAILED DESCRIPTION OF THE INVENTION

The present inventors have identified compounds that are PDE1 inhibitors, and as such are useful to treat neurodegenerative and psychiatric disorders. The present invention thus provides compounds of formula (I) that are effective in inhibiting PDE1 for use as a medicament in the treatment of a mammal, preferably a human.

The invention provides a compound of formula (I) or a pharmaceutically acceptable salt thereof, as well as a pharmaceutical composition containing such a compound, for use in the treatment of a brain disease which could be a neurodegenerative disorder or a psychiatric disorder. In a preferred embodiment, the neurodegenerative disorder is selected from the group consisting of Alzheimer's Disease, Parkinson's Disease and Huntington's Disease. In another preferred embodiment, the psychiatric disorder is selected from the group consisting of Attention Deficit Hyperactivity Disorder (ADHD), depression, anxiety, narcolepsy, cognitive impairment and cognitive impairment associated with schizophrenia (CIAS). Other brain disorders could be e.g. restless leg syndrome.

This invention further provides a method of treating a brain disease which could be a neurodegenerative or a psychiatric disorder, which method comprises administering to said mammal a pharmaceutically effective amount of a compound of formula (I) or a pharmaceutically acceptable salt thereof. Examples of neurodegenerative disorders that can be treated according to the present invention include Alzheimer's Disease, Parkinson's Disease and Huntington's Disease, which method comprises administering to the subject a therapeutically effective amount of a compound of formula (I). Examples of psychiatric disorders that can be treated according to the present invention include Attention Deficit Hyperactivity Disorder (ADHD), depression, narcolepsy, cognitive impairment and cognitive impairment associated with schizophrenia (CIAS). Other brain disorders to be treated could be e.g. restless leg syndrome.

Embodiments of the Invention

In the following, embodiments of the invention are disclosed. The first embodiment is denoted E1, the second embodiment is denoted E2 and so forth.

E1. A compound according to formula (I)

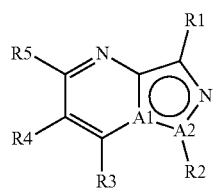

(I)

wherein
A1=C, A2=N and R3=-NR6R7, or
A1=C, A2=N and R3=H, or A1=N, A2=C and R3=H;
R1 is selected from the group consisting of hydrogen, linear or branched $C_{1-4}$ alkyl and $C_{3-4}$ cycloalkyl, wherein said linear or branched $C_{1-4}$ alkyl and $C_{3-4}$ cycloalkyl can optionally be substituted with one or more halogen;
R2 is selected from the group consisting of linear or branched $C_{1-6}$ alkyl, saturated monocyclic $C_{3-6}$ cycloalkyl, oxetanyl, tetrahydrofuranyl and tetrahydropyranyl, wherein said linear or branched $C_{1-6}$ alkyl and saturated monocyclic $C_{3-6}$ cycloalkyl can optionally be substituted with one or more halogen, and wherein said oxetanyl, tetrahydrofuranyl and tetrahydropyranyl can be optionally substituted one or more times with a substituent selected from methyl and halogen;
R4 is selected from the group consisting of hydrogen, linear or branched $C_{1-4}$ alkyl and $C_{3-4}$ cycloalkyl, wherein said linear or branched $C_{1-4}$ alkyl and $C_{3-4}$ cycloalkyl can optionally be substituted with one or more halogen;
R5 is a phenyl, which can be substituted one or more times with one or more substituents selected from $C_{1-4}$ alkoxy, —$CH_2$—$C_{1-4}$alkoxy and —CN, wherein said $C_{1-4}$ alkoxy and —$CH_2$—$C_{1-4}$ alkoxy can be optionally substituted with one or more halogen; or
R5 is selected from the group consisting of benzo[1,3]dioxoleyl or 2,3-dihydrobenzo[b][1,4]dioxinyl; or
R5 is a 5-6 membered heteroaryl which can be substituted one or more times with one or more substituents selected from $C_{1-4}$ alkoxy, —$CH_2$—$C_{1-4}$ alkoxy, —CN, linear or branched $C_{1-4}$ alkyl and $C_{3-4}$ cycloalkyl, wherein said linear or branched $C_{1-4}$ alkyl, said $C_{3-4}$ cycloalkyl, said $C_{1-4}$ alkoxy and said —$CH_2$—$C_{1-4}$alkoxy can optionally be substituted with one or more halogen; or
R5 is a 9-membered bicyclic heteroaryl which can be substituted one or more times with one or more substituents selected from $C_{1-4}$ alkoxy, —$CH_2$—$C_{1-4}$alkoxy, —CN, linear or branched $C_{1-4}$ alkyl and $C_{3-4}$ cycloalkyl, wherein said linear or branched $C_{1-4}$ alkyl, said $C_{3-4}$ cycloalkyl, said $C_{1-4}$ alkoxy and said —$CH_2$—$C_{1-4}$alkoxy can optionally be substituted with one or more halogen;
R6 is selected from the group consisting of hydrogen, linear or branched $C_{1-6}$ alkyl and $C_{3-6}$ cycloalkyl, wherein said linear or branched $C_{1-6}$ alkyl and $C_{3-6}$ cycloalkyl can be optionally substituted with one or more fluorine; and R7 is selected from the group consisting of hydrogen, linear or branched $C_{1-6}$ alkyl, $C_{3-6}$ cycloalkyl, oxetanyl, tetrahydrofuranyl, tetrahydropyranyl, —$CH_2$-oxetanyl, —$CH_2$-tetrahydrofuranyl, —$CH_2$-tetrahydropyranyl and —$CH_2$-pyrrolidinyl, wherein said linear or branched $C_{1-6}$ alkyl, $C_{3-6}$ cycloalkyl, oxetanyl, tetrahydrofuranyl, tetrahydropyranyl, —$CH_2$-oxetanyl, —$CH_2$-tetrahydrofuranyl, —$CH_2$— tetrahydropyranyl and $CH_2$-pyrrolidinyl-2-one can be optionally substituted with one or more substituents selected from methyl, methoxy, ethoxy, oxo and fluorine; or
R6 and R7 are connected to form a 5-7 membered saturated heterocyclic ring with the nitrogen atom to which they are attached and 4-6 carbon atoms; wherein said heterocyclic ring can be optionally substituted with one or more substituents selected from methoxy, methyl and fluorine;
or a pharmaceutically acceptable salt thereof;
with the proviso that said compound is not one of the following two compounds or a salt thereof:
1H-Pyrazolo[4,3-b]pyridine, 3-(1,1-dimethylethyl)-1-methyl-5-phenyl-; and
1H-Pyrazolo[4,3-b]pyridine, 5-(3-pyridinyl)-1-(tetrahydro-2H-pyran-2-yl)-.

E2. The compound according to embodiment 1 of formula (Ia)

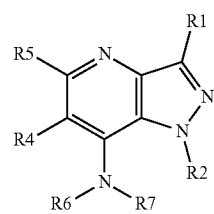

(Ia)

R1, R2, R4, R5, R6 and R7 are as defined in embodiment 1; or a pharmaceutically acceptable salt thereof.

E3. The compound according to embodiment 2, wherein R6 is hydrogen and R7 is selected from the group consisting of hydrogen, linear or branched $C_{1-6}$ alkyl, $C_{3-6}$ cycloalkyl, oxetanyl, tetrahydrofuranyl, tetrahydropyranyl, —$CH_2$-oxetanyl, —$CH_2$-tetrahydrofuranyl, —$CH_2$-tetrahydropyranyl and —$CH_2$-pyrrolidinyl, wherein said linear or branched $C_{1-6}$ alkyl, $C_{3-6}$ cycloalkyl, oxetanyl, tetrahydrofuranyl, tetrahydropyranyl, —$CH_2$— oxetanyl, —$CH_2$-tetrahydrofuranyl, —$CH_2$-tetrahydropyranyl and $CH_2$-pyrrolidinyl-2-one can be optionally substituted with one or more substituents selected from methyl, methoxy, ethoxy, oxo and fluorine.

E4. The compound according to embodiment 2, wherein R6 and R7 are connected to form a 5-7 membered saturated heterocyclic ring with the nitrogen atom to which they are attached and 4-6 carbon atoms; wherein said heterocyclic ring can be optionally substituted with one or more substituents selected from methoxy, methyl and fluorine.

E5. The compound according to embodiment 4, wherein said saturated heterocyclic ring is pyrrolidinyl.

E6. The compound according to embodiment 1 of formula (Ib)

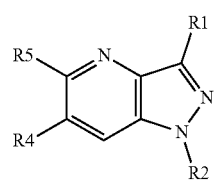

(Ib)

wherein R1, R2, R4 and R5 are as defined in embodiment 1; or a pharmaceutically acceptable salt thereof.

E7. The compound according to embodiment 1 of formula (Ic)

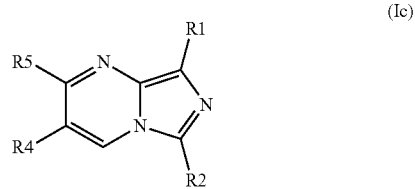

(Ic)

wherein R1, R2, R4 and R5 are as defined in embodiment 1; or a pharmaceutically acceptable salt thereof.

E8. The compound according to any one of embodiments 1-7, wherein R1 is selected from hydrogen and unsubstituted linear or branched $C_{1-4}$ alkyl.

E9. The compound according to embodiment 8, wherein R1 is selected from hydrogen and methyl.

E10. The compound according to any one of embodiments 1-9, wherein R2 is selected from linear or branched $C_{1-6}$ alkyl, saturated monocyclic $C_{3-6}$ cycloalkyl; wherein said linear or branched $C_{1-6}$ alkyl and saturated monocyclic $C_{3-6}$ cycloalkyl can be optionally substituted with one or more halogen.

E11. The compound according to embodiment 10, wherein R2 is selected from methyl, ethyl, 1-propyl, 2-propyl, 2-butyl, 3-pentyl, cyclopropyl, cyclobutyl and cyclopentyl all of which can be optionally substituted with one or more F.

E12. The compound according to any one of embodiments 1-9, wherein R2 is selected from the group consisting of oxetanyl, tetrahydrofuranyl and tetrahydropyranyl, all of which can be optionally substituted with a substituent selected from methyl and halogen.

E13. The compound according to any one of embodiments 1-12, wherein R4 is selected from methyl and hydrogen.

E14. The compound according to any one of embodiments 1-13, wherein R5 is a phenyl, which can be substituted one or more times with one or more substituents selected from $C_{1-4}$ alkoxy, $-CH_2-C_{1-4}$ alkoxy or $-CN$, wherein said $C_{1-4}$ alkoxy and $-CH_2-C_{1-4}$alkoxy can be optionally substituted with one or more fluorine.

E15. The compound according to any of embodiments 1-13, wherein R5 is selected from the group consisting of benzo[1,3]dioxoleyl and 2,3-dihydrobenzo[b][1,4]dioxinyl.

E16. The compound according to any of embodiments 1-13, wherein R5 is a 5-6 membered heteroaryl which can be substituted one or more times with one or more substituents selected from $C_{1-4}$ alkoxy, $-CH_2-C_{1-4}$alkoxy, $-CN$, linear or branched $C_{1-4}$ alkyl and $C_{3-4}$ cycloalkyl, wherein said linear or branched $C_{1-4}$ alkyl, said $C_{3-4}$ cycloalkyl, said $C_{1-4}$ alkoxy and said $-CH_2-C_{1-4}$alkoxy can optionally be substituted with one or more halogen.

E17. The compound according to embodiment 16, wherein said a 5-6 membered heteroaryl is a 6 membered heteroaryl.

E18. The compound according to embodiment 17, wherein said 6 membered heteroaryl is selected from pyridyl and pyrimidyl.

E19. The compound according to any of embodiments 1-13, wherein R5 is a 9-membered bicyclic heteroaryl which can be substituted one or more times with one or more substituents selected from $C_{1-4}$ alkoxy, $-CH_2-C_{1-4}$ alkoxy, $-CN$, linear or branched $C_{1-4}$ alkyl and $C_{3-4}$ cycloalkyl, wherein said linear or branched $C_{1-4}$ alkyl, said $C_{3-4}$ cycloalkyl, said $C_{1-4}$ alkoxy and said $-CH_2-C_{1-4}$alkoxy can optionally be substituted with one or more halogen.

E20. The compound according to embodiment 19, wherein said 9 membered bicyclic heteroaryl is 1H-pyrazolo[1,5-a]pyridine.

E21. The compound according to embodiment 1, wherein the compound is selected from the group consisting of:

1: 5-(2-ethoxy-3-pyridyl)-1,3-dimethyl-7-pyrrolidin-1-yl-pyrazolo[4,3-b]pyridine;

2: 5-(2-ethoxy-3-pyridyl)-N,1-di(tetrahydrofuran-3-yl)pyrazolo[4,3-b]pyridin-7-amine;

3: (±)-5-(2-ethoxy-3-pyridyl)-7-pyrrolidin-1-yl-1-tetrahydrofuran-3-yl-pyrazolo[4,3-b]pyridine;

4: 5-(2-ethoxy-3-pyridyl)-1-(oxetan-3-yl)-7-pyrrolidin-1-yl-pyrazolo[4,3-b]pyridine;

5: (±)-5-(2-ethoxy-3-pyridyl)-1-(oxetan-3-yl)-N-tetrahydrofuran-3-yl-pyrazolo[4,3-b]pyridin-7-amine;

6: 5-(2-ethoxy-3-pyridyl)-1-isopropyl-N-[[(2S)-tetrahydrofuran-2-yl]methyl]pyrazolo[4,3-b]pyridin-7-amine;

7: 5-(2-ethoxy-3-pyridyl)-1-isopropyl-N-[[(2R)-tetrahydrofuran-2-yl]methyl]pyrazolo[4,3-b]pyridin-7-amine;

8: 5-(2-ethoxy-3-pyridyl)-1-isopropyl-N-[(3R)-tetrahydropyran-3-yl]pyrazolo[4,3-b]pyridin-7-amine;

9: 5-(2-ethoxy-3-pyridyl)-1-isopropyl-N-[(3S)-tetrahydropyran-3-yl]pyrazolo[4,3-b]pyridin-7-amine;

10: 5-(2-ethoxy-3-pyridyl)-1-isopropyl-N-tetrahydropyran-4-yl-pyrazolo[4,3-b]pyridin-7-amine;

11: 5-(2-ethoxy-3-pyridyl)-1-isopropyl-N-[trans-4-methoxytetrahydrofuran-3-yl]pyrazolo[4,3-b]pyridin-7-amine;

12: 5-(2-ethoxy-3-pyridyl)-N,1-diisopropyl-pyrazolo[4,3-b]pyridin-7-amine;

13: 5-(2-ethoxy-3-pyridyl)-1-isopropyl-N-methyl-pyrazolo[4,3-b]pyridin-7-amine;

14: 5-(2-ethoxy-3-pyridyl)-1-methyl-7-pyrrolidin-1-yl-pyrazolo[4,3-b]pyridine;

15: 5-(2-ethoxy-3-pyridyl)-1-ethyl-3,6-dimethyl-pyrazolo[4,3-b]pyridine;

16: 5-(2-ethoxy-3-pyridyl)-1-ethyl-7-pyrrolidin-1-yl-pyrazolo[4,3-b]pyridine;

17: 5-(2-ethoxy-3-pyridyl)-1-isopropyl-7-pyrrolidin-1-yl-pyrazolo[4,3-b]pyridine;

18: 5-(2-ethoxy-3-pyridyl)-1-propyl-7-pyrrolidin-1-yl-pyrazolo[4,3-b]pyridine;

19: 5-(2-ethoxy-3-pyridyl)-1-ethyl-N-[tetrahydrofuran-3-yl]pyrazolo[4,3-b]pyridin-7-amine, enantiomer 1;

20: 5-(2-ethoxy-3-pyridyl)-1-ethyl-N-[tetrahydrofuran-3-yl]pyrazolo[4,3-b]pyridin-7-amine, enantiomer 2;

21: 5-(2-ethoxy-3-pyridyl)-1-isopropyl-N-[tetrahydrofuran-3-yl]pyrazolo[4,3-b]pyridin-7-amine, enantiomer 1;

22: 5-(2-ethoxy-3-pyridyl)-1-isopropyl-N-[tetrahydrofuran-3-yl]pyrazolo[4,3-b]pyridin-7-amine, enantiomer 2;

23: 5-(2-ethoxy-3-pyridyl)-1-propyl-N-[tetrahydrofuran-3-yl]pyrazolo[4,3-b]pyridin-7-amine, enantiomer 1.

24: 5-(2-ethoxy-3-pyridyl)-1-propyl-N-[tetrahydrofuran-3-yl]pyrazolo[4,3-b]pyridin-7-amine, enantiomer 2;

25: 1-isopropyl-5-(3-pyridyl)-N-[(3R)-tetrahydrofuran-3-yl]pyrazolo[4,3-b]pyridin-7-amine;

26: 1-isopropyl-5-pyrimidin-5-yl-N-[(3R)-tetrahydrofuran-3-yl]pyrazolo[4,3-b]pyridin-7-amine;

27: 1-isopropyl-5-phenyl-N-[(3R)-tetrahydrofuran-3-yl]pyrazolo[4,3-b]pyridin-7-amine;

28: 1-isopropyl-5-(2-methoxy-3-pyridyl)-N-[(3R)-tetrahydrofuran-3-yl]pyrazolo[4,3-b]pyridin-7-amine;

29: 1-isopropyl-5-(2-methoxy-6-methyl-3-pyridyl)-N-[(3R)-tetrahydrofuran-3-yl]pyrazolo[4,3-b]pyridin-7-amine;
30: 1-isopropyl-5-(3-methoxy-4-pyridyl)-N-[(3R)-tetrahydrofuran-3-yl]pyrazolo[4,3-b]pyridin-7-amine;
31: 1-isopropyl-5-(4-methoxy-3-pyridyl)-N-[(3R)-tetrahydrofuran-3-yl]pyrazolo[4,3-b]pyridin-7-amine;
32: 5-(1,3-benzodioxol-4-yl)-1-isopropyl-N-[(3R)-tetrahydrofuran-3-yl]pyrazolo[4,3-b]pyridin-7-amine;
33: 5-(4-ethoxyphenyl)-1-isopropyl-N-[(3R)-tetrahydrofuran-3-yl]pyrazolo[4,3-b]pyridin-7-amine;
34: 5-(2-ethoxy-4-methyl-3-pyridyl)-1-isopropyl-N-[(3R)-tetrahydrofuran-3-yl]pyrazolo[4,3-b]pyridin-7-amine;
35: 1-isopropyl-5-pyrazolo[1,5-a]pyridin-3-yl-N-[(3R)-tetrahydrofuran-3-yl]pyrazolo[4,3-b]pyridin-7-amine;
36: 5-(2-tert-butoxy-3-pyridyl)-1-isopropyl-N-[(3R)-tetrahydrofuran-3-yl]pyrazolo[4,3-b]pyridin-7-amine;
37: 1-isopropyl-5-[(3-methoxyphenyl)methyl]-N-[(3R)-tetrahydrofuran-3-yl]pyrazolo[4,3-b]pyridin-7-amine;
38: 5-(2,5-dimethoxy-4-pyridyl)-1-isopropyl-N-[(3R)-tetrahydrofuran-3-yl]pyrazolo[4,3-b]pyridin-7-amine;
39: 1-isopropyl-5-(3-methyl-2-pyridyl)-N-[(3R)-tetrahydrofuran-3-yl]pyrazolo[4,3-b]pyridin-7-amine;
40: 1-isopropyl-5-(3-methoxy-2-pyridyl)-N-[(3R)-tetrahydrofuran-3-yl]pyrazolo[4,3-b]pyridin-7-amine;
41: 2-[1-isopropyl-7-[[(3R)-tetrahydrofuran-3-yl]amino]pyrazolo[4,3-b]pyridin-5-yl]benzonitrile;
42: 5-(2,3-dihydro-1,4-benzodioxin-5-yl)-1-isopropyl-N-[(3R)-tetrahydrofuran-3-yl]pyrazolo[4,3-b]pyridin-7-amine;
43: 5-[(4-fluorophenyl)methyl]-1-isopropyl-N-[(3R)-tetrahydrofuran-3-yl]pyrazolo[4,3-b]pyridin-7-amine;
44: 5-[1-isopropyl-7-[[(3R)-tetrahydrofuran-3-yl]amino]pyrazolo[4,3-b]pyridin-5-yl]pyridine-3-carbonitrile;
45: 1-isopropyl-5-[3-(methoxymethyl)phenyl]-N-[(3R)-tetrahydrofuran-3-yl]pyrazolo[4,3-b]pyridin-7-amine;
46: 5-(5-ethoxy-3-pyridyl)-1-isopropyl-N-[(3R)-tetrahydrofuran-3-yl]pyrazolo[4,3-b]pyridin-7-amine;
47: 1-isopropyl-5-(5-methoxy-3-pyridyl)-N-[(3R)-tetrahydrofuran-3-yl]pyrazolo[4,3-b]pyridin-7-amine;
48: 5-[3-(difluoromethoxy)phenyl]-1-isopropyl-N-[(3R)-tetrahydrofuran-3-yl]pyrazolo[4,3-b]pyridin-7-amine;
49: 1-isopropyl-5-(4-methoxypyrimidin-5-yl)-N-[(3R)-tetrahydrofuran-3-yl]pyrazolo[4,3-b]pyridin-7-amine;
50: 5-(4-ethoxypyrimidin-5-yl)-1-isopropyl-N-[(3R)-tetrahydrofuran-3-yl]pyrazolo[4,3-b]pyridin-7-amine;
51: 1-isopropyl-5-(5-methoxy-2-methyl-3-pyridyl)-N-[(3R)-tetrahydrofuran-3-yl]pyrazolo[4,3-b]pyridin-7-amine;
52: 1-isopropyl-5-(2-methoxy-5-methyl-3-pyridyl)-N-[(3R)-tetrahydrofuran-3-yl]pyrazolo[4,3-b]pyridin-7-amine;
53: 5-(2-ethoxyphenyl)-1-isopropyl-N-[(3R)-tetrahydrofuran-3-yl]pyrazolo[4,3-b]pyridin-7-amine;
54: 5-[1-isopropyl-7-[[(3R)-tetrahydrofuran-3-yl]amino]pyrazolo[4,3-b]pyridin-5-yl]-6-methoxy-pyridine-3-carbonitrile;
55: 6-ethoxy-5-[1-isopropyl-7-[[(3R)-tetrahydrofuran-3-yl]amino]pyrazolo[4,3-b]pyridin-5-yl]pyridine-3-carbonitrile;
56: 5-(2-ethyl-3-pyridyl)-1-isopropyl-N-[(3R)-tetrahydrofuran-3-yl]pyrazolo[4,3-b]pyridin-7-amine;
57: 1-isopropyl-5-[(4-methoxyphenyl)methyl]-N-[(3R)-tetrahydrofuran-3-yl]pyrazolo[4,3-b]pyridin-7-amine;
58: 1-isopropyl-5-[2-(methoxymethyl)-3-pyridyl]-N-[(3R)-tetrahydrofuran-3-yl]pyrazolo[4,3-b]pyridin-7-amine;
59: 5-(2-ethoxy-3-pyridyl)-1-isopropyl-3-methyl-pyrazolo[4,3-b]pyridine;
60: 1-isopropyl-3,6-dimethyl-5-phenyl-pyrazolo[4,3-b]pyridine;
61: 1-isopropyl-5-(2-methoxy-3-pyridyl)-3,6-dimethyl-pyrazolo[4,3-b]pyridine;
62: 1-isopropyl-5-(2-methoxyphenyl)-3,6-dimethyl-pyrazolo[4,3-b]pyridine;
63: 5-(2-ethoxy-3-pyridyl)-1-isopropyl-3,6-dimethyl-pyrazolo[4,3-b]pyridine;
64: 1-isopropyl-3,6-dimethyl-5-(2-propoxy-3-pyridyl)pyrazolo[4,3-b]pyridine;
65: 5-(2-ethoxy-3-pyridyl)-1-isopropyl-N,3-dimethyl-pyrazolo[4,3-b]pyridin-7-amine;
66: 5-(2-ethoxy-3-pyridyl)-N-ethyl-1-isopropyl-3-methyl-pyrazolo[4,3-b]pyridin-7-amine;
67: (±)-5-[[[5-(2-ethoxy-3-pyridyl)-1-isopropyl-3-methyl-pyrazolo[4,3-b]pyridin-7-yl]amino]methyl]-1-methyl-pyrrolidin-2-one;
68: 4-[[[5-(2-ethoxy-3-pyridyl)-1-isopropyl-3-methyl-pyrazolo[4,3-b]pyridin-7-yl]amino]methyl]-1-methyl-pyrrolidin-2-one;
69: 5-(2-ethoxy-3-pyridyl)-1-isopropyl-3-methyl-pyrazolo[4,3-b]pyridin-7-amine;
70: 5-(2-ethoxy-3-pyridyl)-1-isopropyl-pyrazolo[4,3-b]pyridine;
71: 2-(2-ethoxy-3-pyridyl)-6-isopropyl-3,8-dimethyl-imidazo[1,5-a]pyrimidine;
72: 2-(2-ethoxy-3-pyridyl)-6-isopropyl-8-methyl-imidazo[1,5-a]pyrimidine;
73: 6-cyclobutyl-2-(2-ethoxy-3-pyridyl)-8-methyl-imidazo[1,5-a]pyrimidine;
74: 6-cyclopropyl-2-(2-ethoxy-3-pyridyl)-8-methyl-imidazo[1,5-a]pyrimidine;
75: 2-(2-ethoxy-3-pyridyl)-6-(1-ethylpropyl)-8-methyl-imidazo[1,5-a]pyrimidine;
76: (±)-2-(2-ethoxy-3-pyridyl)-8-methyl-6-sec-butyl-imidazo[1,5-a]pyrimidine;
77: 2-(2-ethoxy-3-pyridyl)-8-methyl-6-(3-methyloxetan-3-yl)imidazo[1,5-a]pyrimidine;
78: 2-(2-ethoxy-3-pyridyl)-8-methyl-6-(2,2,2-trifluoroethyl)imidazo[1,5-a]pyrimidine;
79: 2-(2-ethoxy-3-pyridyl)-8-methyl-6-(oxetan-3-yl)imidazo[1,5-a]pyrimidine;
80: 6-cyclopentyl-2-(2-ethoxy-3-pyridyl)-8-methyl-imidazo[1,5-a]pyrimidine;
81: (±)-2-(2-ethoxy-3-pyridyl)-8-methyl-6-tetrahydrofuran-3-yl-imidazo[1,5-a]pyrimidine;
82: 6-tert-butyl-2-(2-ethoxy-3-pyridyl)-8-methyl-imidazo[1,5-a]pyrimidine;
83: 2-(2-ethoxy-3-pyridyl)-8-methyl-6-[1-methylpropyl]imidazo[1,5-a]pyrimidine, enantiomer 1;
84: 2-(2-ethoxy-3-pyridyl)-8-methyl-6-[1-methylpropyl]imidazo[1,5-a]pyrimidine, enantiomer 2.
85: 5-(2-ethoxy-3-pyridyl)-7-[(3R)-3-methoxypyrrolidin-1-yl]-1-methyl-pyrazolo[4,3-b]pyridine;
86: 5-(2-ethoxy-3-pyridyl)-N-[(1R,2R)-2-methoxycyclopentyl]-1-methyl-pyrazolo[4,3-b]pyridin-7-amine;
87: (±)-5-(2-ethoxy-3-pyridyl)-7-(3-fluoro-3-methyl-pyrrolidin-1-yl)-1-methyl-pyrazolo[4,3-b]pyridine;
88: 5-(2-ethoxy-3-pyridyl)-N-(3-methoxycyclopentyl)-1-methyl-pyrazolo[4,3-b]pyridin-7-amine;
or a pharmaceutically acceptable salt of any of these compounds.
E22. The compound according to embodiment 1, wherein the compound is selected from the group consisting of:

1: 5-(2-ethoxy-3-pyridyl)-1,3-dimethyl-7-pyrrolidin-1-yl-pyrazolo[4,3-b]pyridine;
2: 5-(2-ethoxy-3-pyridyl)-N,1-di(tetrahydrofuran-3-yl)pyrazolo[4,3-b]pyridin-7-amine;
3: (±)-5-(2-ethoxy-3-pyridyl)-7-pyrrolidin-1-yl-1-tetrahydrofuran-3-yl-pyrazolo[4,3-b]pyridine;
4: 5-(2-ethoxy-3-pyridyl)-1-(oxetan-3-yl)-7-pyrrolidin-1-yl-pyrazolo[4,3-b]pyridine;
5: (±)-5-(2-ethoxy-3-pyridyl)-1-(oxetan-3-yl)-N-tetrahydrofuran-3-yl-pyrazolo[4,3-b]pyridin-7-amine;
6: 5-(2-ethoxy-3-pyridyl)-1-isopropyl-N-[[(2S)-tetrahydrofuran-2-yl]methyl]pyrazolo[4,3-b]pyridin-7-amine;
7: 5-(2-ethoxy-3-pyridyl)-1-isopropyl-N-[[(2R)-tetrahydrofuran-2-yl]methyl]pyrazolo[4,3-b]pyridin-7-amine;
8: 5-(2-ethoxy-3-pyridyl)-1-isopropyl-N-[(3R)-tetrahydropyran-3-yl]pyrazolo[4,3-b]pyridin-7-amine;
9: 5-(2-ethoxy-3-pyridyl)-1-isopropyl-N-[(3S)-tetrahydropyran-3-yl]pyrazolo[4,3-b]pyridin-7-amine;
10: 5-(2-ethoxy-3-pyridyl)-1-isopropyl-N-tetrahydropyran-4-yl-pyrazolo[4,3-b]pyridin-7-amine;
11: 5-(2-ethoxy-3-pyridyl)-1-isopropyl-N-[trans-4-methoxytetrahydrofuran-3-yl]pyrazolo[4,3-b]pyridin-7-amine;
12: 5-(2-ethoxy-3-pyridyl)-N,1-diisopropyl-pyrazolo[4,3-b]pyridin-7-amine;
13: 5-(2-ethoxy-3-pyridyl)-1-isopropyl-N-methyl-pyrazolo[4,3-b]pyridin-7-amine;
14: 5-(2-ethoxy-3-pyridyl)-1-methyl-7-pyrrolidin-1-yl-pyrazolo[4,3-b]pyridine;
15: 5-(2-ethoxy-3-pyridyl)-1-ethyl-3,6-dimethyl-pyrazolo[4,3-b]pyridine;
16: 5-(2-ethoxy-3-pyridyl)-1-ethyl-7-pyrrolidin-1-yl-pyrazolo[4,3-b]pyridine;
17: 5-(2-ethoxy-3-pyridyl)-1-isopropyl-7-pyrrolidin-1-yl-pyrazolo[4,3-b]pyridine;
18: 5-(2-ethoxy-3-pyridyl)-1-propyl-7-pyrrolidin-1-yl-pyrazolo[4,3-b]pyridine;
19: (R)-5-(2-ethoxy-3-pyridyl)-1-ethyl-N-[tetrahydrofuran-3-yl]pyrazolo[4,3-b]pyridin-7-amine or (S)-5-(2-ethoxy-3-pyridyl)-1-ethyl-N-[tetrahydrofuran-3-yl]pyrazolo[4,3-b]pyridin-7-amine;
20: (R)-5-(2-ethoxy-3-pyridyl)-1-ethyl-N-[tetrahydrofuran-3-yl]pyrazolo[4,3-b]pyridin-7-amine or (S)-5-(2-ethoxy-3-pyridyl)-1-ethyl-N-[tetrahydrofuran-3-yl]pyrazolo[4,3-b]pyridin-7-amine;
21: (R)-5-(2-ethoxy-3-pyridyl)-1-isopropyl-N-[tetrahydrofuran-3-yl]pyrazolo[4,3-b]pyridin-7-amine or (S)-5-(2-ethoxy-3-pyridyl)-1-isopropyl-N-[tetrahydrofuran-3-yl]pyrazolo[4,3-b]pyridin-7-amine;
22: (R)-5-(2-ethoxy-3-pyridyl)-1-isopropyl-N-[tetrahydrofuran-3-yl]pyrazolo[4,3-b]pyridin-7-amine or (S)-5-(2-ethoxy-3-pyridyl)-1-isopropyl-N-[tetrahydrofuran-3-yl]pyrazolo[4,3-b]pyridin-7-amine;
23: (R)-5-(2-ethoxy-3-pyridyl)-1-propyl-N-[tetrahydrofuran-3-yl]pyrazolo[4,3-b]pyridin-7-amine or (S)-5-(2-ethoxy-3-pyridyl)-1-propyl-N-[tetrahydrofuran-3-yl]pyrazolo[4,3-b]pyridin-7-amine;
24: (R)-5-(2-ethoxy-3-pyridyl)-1-propyl-N-[tetrahydrofuran-3-yl]pyrazolo[4,3-b]pyridin-7-amine or (S)-5-(2-ethoxy-3-pyridyl)-1-propyl-N-[tetrahydrofuran-3-yl]pyrazolo[4,3-b]pyridin-7-amine;
25: 1-isopropyl-5-(3-pyridyl)-N-[(3R)-tetrahydrofuran-3-yl]pyrazolo[4,3-b]pyridin-7-amine;
26: 1-isopropyl-5-pyrimidin-5-yl-N-[(3R)-tetrahydrofuran-3-yl]pyrazolo[4,3-b]pyridin-7-amine;
27: 1-isopropyl-5-phenyl-N-[(3R)-tetrahydrofuran-3-yl]pyrazolo[4,3-b]pyridin-7-amine;
28: 1-isopropyl-5-(2-methoxy-3-pyridyl)-N-[(3R)-tetrahydrofuran-3-yl]pyrazolo[4,3-b]pyridin-7-amine;
29: 1-isopropyl-5-(2-methoxy-6-methyl-3-pyridyl)-N-[(3R)-tetrahydrofuran-3-yl]pyrazolo[4,3-b]pyridin-7-amine;
30: 1-isopropyl-5-(3-methoxy-4-pyridyl)-N-[(3R)-tetrahydrofuran-3-yl]pyrazolo[4,3-b]pyridin-7-amine;
31: 1-isopropyl-5-(4-methoxy-3-pyridyl)-N-[(3R)-tetrahydrofuran-3-yl]pyrazolo[4,3-b]pyridin-7-amine;
32: 5-(1,3-benzodioxol-4-yl)-1-isopropyl-N-[(3R)-tetrahydrofuran-3-yl]pyrazolo[4,3-b]pyridin-7-amine;
33: 5-(4-ethoxyphenyl)-1-isopropyl-N-[(3R)-tetrahydrofuran-3-yl]pyrazolo[4,3-b]pyridin-7-amine;
34: 5-(2-ethoxy-4-methyl-3-pyridyl)-1-isopropyl-N-[(3R)-tetrahydrofuran-3-yl]pyrazolo[4,3-b]pyridin-7-amine;
35: 1-isopropyl-5-pyrazolo[1,5-a]pyridin-3-yl-N-[(3R)-tetrahydrofuran-3-yl]pyrazolo[4,3-b]pyridin-7-amine;
36: 5-(2-tert-butoxy-3-pyridyl)-1-isopropyl-N-[(3R)-tetrahydrofuran-3-yl]pyrazolo[4,3-b]pyridin-7-amine;
37: 1-isopropyl-5-[(3-methoxyphenyl)methyl]-N-[(3R)-tetrahydrofuran-3-yl]pyrazolo[4,3-b]pyridin-7-amine;
38: 5-(2,5-dimethoxy-4-pyridyl)-1-isopropyl-N-[(3R)-tetrahydrofuran-3-yl]pyrazolo[4,3-b]pyridin-7-amine;
39: 1-isopropyl-5-(3-methyl-2-pyridyl)-N-[(3R)-tetrahydrofuran-3-yl]pyrazolo[4,3-b]pyridin-7-amine;
40: 1-isopropyl-5-(3-methoxy-2-pyridyl)-N-[(3R)-tetrahydrofuran-3-yl]pyrazolo[4,3-b]pyridin-7-amine;
41: 2-[1-isopropyl-7-[[(3R)-tetrahydrofuran-3-yl]amino]pyrazolo[4,3-b]pyridin-5-yl]benzonitrile;
42: 5-(2,3-dihydro-1,4-benzodioxin-5-yl)-1-isopropyl-N-[(3R)-tetrahydrofuran-3-yl]pyrazolo[4,3-b]pyridin-7-amine;
43: 5-[(4-fluorophenyl)methyl]-1-isopropyl-N-[(3R)-tetrahydrofuran-3-yl]pyrazolo[4,3-b]pyridin-7-amine;
44: 5-[1-isopropyl-7-[[(3R)-tetrahydrofuran-3-yl]amino]pyrazolo[4,3-b]pyridin-5-yl]pyridine-3-carbonitrile;
45: 1-isopropyl-5-[3-(methoxymethyl)phenyl]-N-[(3R)-tetrahydrofuran-3-yl]pyrazolo[4,3-b]pyridin-7-amine;
46: 5-(5-ethoxy-3-pyridyl)-1-isopropyl-N-[(3R)-tetrahydrofuran-3-yl]pyrazolo[4,3-b]pyridin-7-amine;
47: 1-isopropyl-5-(5-methoxy-3-pyridyl)-N-[(3R)-tetrahydrofuran-3-yl]pyrazolo[4,3-b]pyridin-7-amine;
48: 5-[3-(difluoromethoxy)phenyl]-1-isopropyl-N-[(3R)-tetrahydrofuran-3-yl]pyrazolo[4,3-b]pyridin-7-amine;
49: 1-isopropyl-5-(4-methoxypyrimidin-5-yl)-N-[(3R)-tetrahydrofuran-3-yl]pyrazolo[4,3-b]pyridin-7-amine;
50: 5-(4-ethoxypyrimidin-5-yl)-1-isopropyl-N-[(3R)-tetrahydrofuran-3-yl]pyrazolo[4,3-b]pyridin-7-amine;
51: 1-isopropyl-5-(5-methoxy-2-methyl-3-pyridyl)-N-[(3R)-tetrahydrofuran-3-yl]pyrazolo[4,3-b]pyridin-7-amine;
52: 1-isopropyl-5-(2-methoxy-5-methyl-3-pyridyl)-N-[(3R)-tetrahydrofuran-3-yl]pyrazolo[4,3-b]pyridin-7-amine;
53: 5-(2-ethoxyphenyl)-1-isopropyl-N-[(3R)-tetrahydrofuran-3-yl]pyrazolo[4,3-b]pyridin-7-amine;
54: 5-[1-isopropyl-7-[[(3R)-tetrahydrofuran-3-yl]amino]pyrazolo[4,3-b]pyridin-5-yl]-6-methoxy-pyridine-3-carbonitrile;
55: 6-ethoxy-5-[1-isopropyl-7-[[(3R)-tetrahydrofuran-3-yl]amino]pyrazolo[4,3-b]pyridin-5-yl]pyridine-3-carbonitrile;
56: 5-(2-ethyl-3-pyridyl)-1-isopropyl-N-[(3R)-tetrahydrofuran-3-yl]pyrazolo[4,3-b]pyridin-7-amine;
57: 1-isopropyl-5-[(4-methoxyphenyl)methyl]-N-[(3R)-tetrahydrofuran-3-yl]pyrazolo[4,3-b]pyridin-7-amine;

58: 1-isopropyl-5-[2-(methoxymethyl)-3-pyridyl]-N-[(3R)-tetrahydrofuran-3-yl]pyrazolo[4,3-b]pyridin-7-amine;
59: 5-(2-ethoxy-3-pyridyl)-1-isopropyl-3-methyl-pyrazolo[4,3-b]pyridine;
60: 1-isopropyl-3,6-dimethyl-5-phenyl-pyrazolo[4,3-b]pyridine;
61: 1-isopropyl-5-(2-methoxy-3-pyridyl)-3,6-dimethyl-pyrazolo[4,3-b]pyridine;
62: 1-isopropyl-5-(2-methoxyphenyl)-3,6-dimethyl-pyrazolo[4,3-b]pyridine;
63: 5-(2-ethoxy-3-pyridyl)-1-isopropyl-3,6-dimethyl-pyrazolo[4,3-b]pyridine;
64: 1-isopropyl-3,6-dimethyl-5-(2-propoxy-3-pyridyl)pyrazolo[4,3-b]pyridine;
65: 5-(2-ethoxy-3-pyridyl)-1-isopropyl-N,3-dimethyl-pyrazolo[4,3-b]pyridin-7-amine;
66: 5-(2-ethoxy-3-pyridyl)-N-ethyl-1-isopropyl-3-methyl-pyrazolo[4,3-b]pyridin-7-amine;
67: (±)-5-[[[5-(2-ethoxy-3-pyridyl)-1-isopropyl-3-methyl-pyrazolo[4,3-b]pyridin-7-yl]amino]methyl]-1-methyl-pyrrolidin-2-one;
68: 4-[[[5-(2-ethoxy-3-pyridyl)-1-isopropyl-3-methyl-pyrazolo[4,3-b]pyridin-7-yl]amino]methyl]-1-methyl-pyrrolidin-2-one;
69: 5-(2-ethoxy-3-pyridyl)-1-isopropyl-3-methyl-pyrazolo[4,3-b]pyridin-7-amine;
70: 5-(2-ethoxy-3-pyridyl)-1-isopropyl-pyrazolo[4,3-b]pyridine;
71: 2-(2-ethoxy-3-pyridyl)-6-isopropyl-3,8-dimethyl-imidazo[1,5-a]pyrimidine;
72: 2-(2-ethoxy-3-pyridyl)-6-isopropyl-8-methyl-imidazo[1,5-a]pyrimidine;
73: 6-cyclobutyl-2-(2-ethoxy-3-pyridyl)-8-methyl-imidazo[1,5-a]pyrimidine;
74: 6-cyclopropyl-2-(2-ethoxy-3-pyridyl)-8-methyl-imidazo[1,5-a]pyrimidine;
75: 2-(2-ethoxy-3-pyridyl)-6-(1-ethylpropyl)-8-methyl-imidazo[1,5-a]pyrimidine;
76: (±)-2-(2-ethoxy-3-pyridyl)-8-methyl-6-sec-butyl-imidazo[1,5-a]pyrimidine;
77: 2-(2-ethoxy-3-pyridyl)-8-methyl-6-(3-methyloxetan-3-yl)imidazo[1,5-a]pyrimidine;
78: 2-(2-ethoxy-3-pyridyl)-8-methyl-6-(2,2,2-trifluoroethyl)imidazo[1,5-a]pyrimidine;
79: 2-(2-ethoxy-3-pyridyl)-8-methyl-6-(oxetan-3-yl)imidazo[1,5-a]pyrimidine;
80: 6-cyclopentyl-2-(2-ethoxy-3-pyridyl)-8-methyl-imidazo[1,5-a]pyrimidine;
81: (±)-2-(2-ethoxy-3-pyridyl)-8-methyl-6-tetrahydrofuran-3-yl-imidazo[1,5-a]pyrimidine;
82: 6-tert-butyl-2-(2-ethoxy-3-pyridyl)-8-methyl-imidazo[1,5-a]pyrimidine;
83: (R)-2-(2-ethoxy-3-pyridyl)-8-methyl-6-[1-methylpropyl]imidazo[1,5-a]pyrimidine or (S)-2-(2-ethoxy-3-pyridyl)-8-methyl-6-[1-methylpropyl]imidazo[1,5-a]pyrimidine;
84: (R)-2-(2-ethoxy-3-pyridyl)-8-methyl-6-[1-methylpropyl]imidazo[1,5-a]pyrimidine or (S)-2-(2-ethoxy-3-pyridyl)-8-methyl-6-[1-methylpropyl]imidazo[1,5-a]pyrimidine;
85: 5-(2-ethoxy-3-pyridyl)-7-[(3R)-3-methoxypyrrolidin-1-yl]-1-methyl-pyrazolo[4,3-b]pyridine;
86: 5-(2-ethoxy-3-pyridyl)-N-[(1R,2R)-2-methoxycyclopentyl]-1-methyl-pyrazolo[4,3-b]pyridin-7-amine;
87: (±)-5-(2-ethoxy-3-pyridyl)-7-(3-fluoro-3-methyl-pyrrolidin-1-yl)-1-methyl-pyrazolo[4,3-b]pyridine;
88: 5-(2-ethoxy-3-pyridyl)-N-(3-methoxycyclopentyl)-1-methyl-pyrazolo[4,3-b]pyridin-7-amine;
or a pharmaceutically acceptable salt of any of these compounds.

E23. A compound of any one of embodiments 1-22, wherein said compound has a PDE1A, PDE1B or PDE1C $IC_{50}$ value, determined as described in the section "PDE1 inhibition assay", of 10 micro molar or less, such as 5 micro molar or less, such as 4 micro molar or less, such as 3 micro molar or less, such as 2 micro molar or less, such as 1 micro molar or less, such as 500 nM or less, such as 400 nM or less, such as 300 nM or less, such as 200 nM or less, such as 100 nM or less.

E24. A compound of any one of embodiments 1-23 for use in therapy.

E25. A compound according to any one of embodiments 1-23, for use as a medicament.

E26. A pharmaceutical composition comprising a therapeutically effective amount of a compound of any one of embodiments 1-23 and one or more pharmaceutically acceptable carriers, diluents and excipients.

E27. The pharmaceutical composition according to embodiment 26 for use in the treatment of a neurodegenerative disorder, selected from the group consisting of Alzheimer's Disease, Parkinson's Disease and Huntington's Disease or for use in the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

E28. The pharmaceutical composition according to embodiment 26, wherein said pharmaceutical composition further comprises a second compound, which compound is selected from a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody.

E29. The pharmaceutical composition according to embodiment 27, wherein said composition is for use in the treatment of a neurodegenerative disorder selected from the group consisting of Alzheimer's Disease, Parkinson's Disease and Huntington's Disease.

E30. The pharmaceutical composition according to embodiment 26, further comprising a second compound, which compound is useful in the treatment of a psychiatric disorder.

E31. The pharmaceutical composition according to embodiment 30, wherein said second compound has a pharmacological activity selected from one or more of the following mechanisms: antagonist/inverse agonist/negative modulator/partial agonist/inhibitor of one or more of the targets dopamine D1 receptor, dopamine D2 receptor, dopamine D3 receptor, phosphodiesterase PDE10, serotonin 5-HT2A receptor, serotonin 5-HT6 receptor, and glycine transporter GlyT1; or agonist/positive modulator/partial agonist of one or more of the targets KCNQ channels, NMDA receptor, AMPA receptor and nicotinic alpha-7 receptor.

E32. The pharmaceutical composition according to embodiment 30, wherein said second compound is selected from the list comprising clozapine, risperidone, paliperidone, olanzapine, quetiapine, amisulpride, ziprasidone, aripiprazole, brexpiprazole, asenapine, haloperidole, iloperidone, lurasidone, chlorpromazine, blonanserin, perphenazine, levomepromazine, sulpiride, fluphenazine, zuclopenthixol, flupenthixol and cariprazine.

E33. The pharmaceutical composition according to any of embodiments 30-32, wherein said composition is for use in the treatment of a psychiatric disorder such as Attention Deficit Hyperactivity Disorder (ADHD), depression, anxiety, narcolepsy, cognitive impairment and cognitive impairment associated with schizophrenia (CIAS).

E34. A compound according to any one of embodiments 1-23 for use in the treatment of a neurodegenerative disorder, selected from the group consisting of Alzheimer's Disease, Parkinson's Disease and Huntington's Disease or for use in the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

E35. A compound according to any of embodiments 1-23, for the use in the treatment of a neurodegenerative disorder selected from the group consisting of Alzheimer's Disease, Parkinson's Disease and Huntington's Disease, wherein said compound is used in combination with a second compound, which compound is selected from a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody.

E36. The compound according to any of embodiments 1-23, for the use in the treatment of a psychiatric disorder such as Attention Deficit Hyperactivity Disorder (ADHD), depression, anxiety, narcolepsy, cognitive impairment and cognitive impairment associated with schizophrenia (CIAS), wherein said compound is used in combination with a second compound, which compound is useful in the treatment of a psychiatric disorder.

E37. The compound according to embodiment 36, wherein said second compound, which compound is useful in the treatment of a psychiatric disorder, has a pharmacological activity selected from one or more of the following mechanisms: antagonist/inverse agonist/negative modulator/partial agonist/inhibitor of one or more of the targets dopamine D1 receptor, dopamine D2 receptor, dopamine D3 receptor, phosphodiesterase PDE10, serotonin 5-HT2A receptor, serotonin 5-HT6 receptor, and glycine transporter GlyT1; or agonist/positive modulator/partial agonist of one or more of the targets KCNQ channels, NMDA receptor, AMPA receptor and nicotinic alpha-7 receptor.

E38. The compound according to embodiment 36, wherein said second compound, which compound is useful in the treatment of a psychiatric disorder, is selected from the list comprising clozapine, risperidone, paliperidone, olanzapine, quetiapine, amisulpride, ziprasidone, aripiprazole, brexpiprazole, asenapine, haloperidole, iloperidone, lurasidone, chlorpromazine, blonanserin, perphenazine, levomepromazine, sulpiride, fluphenazine, zuclopenthixol, flupenthixol and cariprazine.

E39. A method for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome, which method comprises the administration of a therapeutically effective amount of a compound according to any one of embodiments 1-23 to a patient in need thereof.

E40. A method for the treatment of a neurodegenerative disorder, selected from the group consisting of Alzheimer's Disease, Parkinson's Disease and Huntington's Disease, which method comprises the administration of a therapeutically effective amount of a compound according to any of embodiments 1-23 in combination with a therapeutically effective amount of a second compound, which compound is selected from a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody; to a patient in need thereof.

E41. A method for the treatment of a psychiatric disorder such as Attention Deficit Hyperactivity Disorder (ADHD), depression, anxiety, narcolepsy, cognitive impairment and cognitive impairment associated with schizophrenia (CIAS), which method comprises the administration of a therapeutically effective amount of a compound according to any of embodiments 1-23 in combination with a therapeutically effective amount of a second compound, which compound is useful in the treatment of a psychiatric disorder; to a patient in need thereof.

E42. The method according to embodiment 41, wherein said second compound, which compound is useful in the treatment of a psychiatric disorder, has a pharmacological activity selected from one or more of the following mechanisms: antagonist/inverse agonist/negative modulator/partial agonist/inhibitor of one or more of the targets dopamine D1 receptor, dopamine D2 receptor, dopamine D3 receptor, phosphodiesterase PDE10, serotonin 5-HT2A receptor, serotonin 5-HT6 receptor, and glycine transporter GlyT1; or agonist/positive modulator/partial agonist of one or more of the targets KCNQ channels, NMDA receptor, AMPA receptor and nicotinic alpha-7 receptor.

E43. The method according to embodiment 41, wherein said second compound, which compound is useful in the treatment of a psychiatric disorder, is selected from the list comprising clozapine, risperidone, paliperidone, olanzapine, quetiapine, amisulpride, ziprasidone, aripiprazole, brexpiprazole, asenapine, haloperidole, iloperidone, lurasidone, chlorpromazine, blonanserin, perphenazine, levomepromazine, sulpiride, fluphenazine, zuclopenthixol, flupenthixol and cariprazine.

E44. Use of a compound according to any one of embodiments 1-23, in the manufacture of a medicament for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

E45. Use of a compound according to any of embodiments 1-23, in the manufacture of a medicament for the treatment of a neurodegenerative disorder, selected from the group consisting of Alzheimer's Disease, Parkinson's Disease and Huntington's Disease, wherein said medicament is for use in combination with a second compound, which compound is selected from a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody.

E46. Use of a compound according to any of embodiments 1-23, in the manufacture of a medicament for the treatment of a psychiatric disorder such as Attention Deficit Hyperactivity Disorder (ADHD), depression, anxiety, narcolepsy, cognitive impairment and cognitive impairment associated with schizophrenia (CIAS), wherein said medicament is for use in combination with a second compound, which compound is useful in the treatment of a psychiatric disorder.

E47. The use according to embodiment 46, wherein said second compound, which compound is useful in the treatment of a psychiatric disorder, has a pharmacological activity selected from one or more of the following mechanisms: antagonist/inverse agonist/negative modulator/partial agonist/inhibitor of one or more of the targets dopamine D1 receptor, dopamine D2 receptor, dopamine D3 receptor, phosphodiesterase PDE10, serotonin 5-HT2A receptor, serotonin 5-HT6 receptor, and glycine transporter GlyT1; or agonist/positive modulator/partial agonist of one or more of the targets KCNQ channels, NMDA receptor, AMPA receptor and nicotinic alpha-7 receptor.

E48. The use according to embodiment 46, wherein said second compound, which compound is useful in the treatment of a psychiatric disorder, is selected from the list comprising clozapine, risperidone, paliperidone, olanzapine, quetiapine, amisulpride, ziprasidone, aripiprazole, brexpiprazole, asenapine, haloperidole, iloperidone, lurasidone, chlorpromazine, blonanserin, The two compounds 1H-Pyrazolo[4,3-b]pyridine, 3-(1,1-dimethylethyl)-1-methyl-5-phenyl-[CAS No. 924629-04-9] and 1H-Pyrazolo[4,3-b]pyridine, 5-(3-pyridinyl)-1-(tetrahydro-2H-pyran-2-yl)-[CAS No. 2077940-89-5] are known in the art and thus disclaimed from the scope of the present invention.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

Compounds of the Invention

TABLE 1

| | | Compounds of the invention | | |
|---|---|---|---|---|
| Example | Compound | PDE1 A, IC$_{50}$ (nM) | PDE1 B, IC$_{50}$ (nM) | PDE1 C, IC$_{50}$ (nM) |
| 1 | 5-(2-ethoxy-3-pyridyl)-1,3-dimethyl-7-pyrrolidin-1-yl-pyrazolo[4,3-b]pyridine | 70% @ 1 μM | 170 | 49% @ 1 μM |
| 2 | 5-(2-ethoxy-3-pyridyl)-N,1-di(tetrahydrofuran-3-yl)pyrazolo[4,3-b]pyridin-7-amine | 13% @ 1 μM | 445 | 403 |
| 3 | (±)-5-(2-ethoxy-3-pyridyl)-7-pyrrolidin-1-yl-1-tetrahydrofuran-3-yl-pyrazolo[4,3-b]pyridine | 27% @ 1 μM | 550 | 29% @ 1 μM |
| 4 | 5-(2-ethoxy-3-pyridyl)-1-(oxetan-3-yl)-7-pyrrolidin-1-yl-pyrazolo[4,3-b]pyridine | 641 | 95 | 56% @ 1 μM |
| 5 | (±)-5-(2-ethoxy-3-pyridyl)-1-(oxetan-3-yl)-N-tetrahydrofuran-3-yl-pyrazolo[4,3-b]pyridin-7-amine | 47% @ 1 μM | 447 | 20% @ 1 μM |
| 6 | 5-(2-ethoxy-3-pyridyl)-1-isopropyl-N-[[(2S)-tetrahydrofuran-2-yl]methyl]pyrazolo[4,3-b]pyridin-7-amine | 653 | 111 | 1391 |
| 7 | 5-(2-ethoxy-3-pyridyl)-1-isopropyl-N-[[(2R)-tetrahydrofuran-2-yl]methyl]pyrazolo[4,3-b]pyridin-7-amine | 449 | 83 | 1708 |
| 8 | 5-(2-ethoxy-3-pyridyl)-1-isopropyl-N-[(3R)-tetrahydropyran-3-yl]pyrazolo[4,3-b]pyridin-7-amine | 2156 | 423 | 2871 |
| 9 | 5-(2-ethoxy-3-pyridyl)-1-isopropyl-N-[(3S)-tetrahydropyran-3-yl]pyrazolo[4,3-b]pyridin-7-amine | 687 | 295 | 2701 |
| 10 | 5-(2-ethoxy-3-pyridyl)-1-isopropyl-N-tetrahydropyran-4-yl-pyrazolo[4,3-b]pyridin-7-amine | 71% @ 10 μM | 126 | 2665 |
| 11 | 5-(2-ethoxy-3-pyridyl)-1-isopropyl-N-[trans-4-methoxytetrahydrofuran-3-yl]pyrazolo[4,3-b]pyridin-7-amine | 575 | 82 | 1480 |
| 12 | 5-(2-ethoxy-3-pyridyl)-N,1-diisopropyl-pyrazolo[4,3-b]pyridin-7-amine | 1118 | 108 | 2228 |
| 13 | 5-(2-ethoxy-3-pyridyl)-1-isopropyl-N-methyl-pyrazolo[4,3-b]pyridin-7-amine | 1029 | 85 | 1057 |

TABLE 1-continued

Compounds of the invention

| Example | Compound | PDE1 A, IC$_{50}$ (nM) | PDE1 B, IC$_{50}$ (nM) | PDE1 C, IC$_{50}$ (nM) |
|---|---|---|---|---|
| 14 | 5-(2-ethoxy-3-pyridyl)-1-methyl-7-pyrrolidin-1-yl-pyrazolo[4,3-b]pyridine | 1092 | 640 | 3500 |
| 15 | 5-(2-ethoxy-3-pyridyl)-1-ethyl-3,6-dimethyl-pyrazolo[4,3-b]pyridine | 1007 | 156 | 1891 |
| 16 | 5-(2-ethoxy-3-pyridyl)-1-ethyl-7-pyrrolidin-1-yl-pyrazolo[4,3-b]pyridine | 461 | 129 | 1815 |
| 17 | 5-(2-ethoxy-3-pyridyl)-1-isopropyl-7-pyrrolidin-1-yl-pyrazolo[4,3-b]pyridine | 353 | 83 | 50% @ 1 μM |
| 18 | 5-(2-ethoxy-3-pyridyl)-1-propyl-7-pyrrolidin-1-yl-pyrazolo[4,3-b]pyridine | 637 | 336 | 64% @ 10 μM |
| 19 | 5-(2-ethoxy-3-pyridyl)-1-ethyl-N-[tetrahydrofuran-3-yl]pyrazolo[4,3-b]pyridin-7-amine, enantiomer 1 | 326 | 86 | 3058 |
| 20 | 5-(2-ethoxy-3-pyridyl)-1-ethyl-N-[tetrahydrofuran-3-yl]pyrazolo[4,3-b]pyridin-7-amine, enantiomer 2 | 467 | 179 | 957 |
| 21 | 5-(2-ethoxy-3-pyridyl)-1-isopropyl-N-[tetrahydrofuran-3-yl]pyrazolo[4,3-b]pyridin-7-amine, enantiomer 1 | 622 | 48 | 1539 |
| 22 | 5-(2-ethoxy-3-pyridyl)-1-isopropyl-N-[tetrahydrofuran-3-yl]pyrazolo[4,3-b]pyridin-7-amine, enantiomer 2 | 458 | 32 | 683 |
| 23 | 5-(2-ethoxy-3-pyridyl)-1-propyl-N-[tetrahydrofuran-3-yl]pyrazolo[4,3-b]pyridin-7-amine, enantiomer 1 | 481 | 171 | 2541 |
| 24 | 5-(2-ethoxy-3-pyridyl)-1-propyl-N-[tetrahydrofuran-3-yl]pyrazolo[4,3-b]pyridin-7-amine, enantiomer 2 | 327 | 177 | 703 |
| 25 | 1-isopropyl-5-(3-pyridyl)-N-[(3R)-tetrahydrofuran-3-yl]pyrazolo[4,3-b]pyridin-7-amine | 2159 | 648 | 65% @ 10 μM |
| 26 | 1-isopropyl-5-pyrimidin-5-yl-N-[(3R)-tetrahydrofuran-3-yl]pyrazolo[4,3-b]pyridin-7-amine | 54% @ 10 μM | 3647 | 70% @ 10 μM |
| 27 | 1-isopropyl-5-phenyl-N-[(3R)-tetrahydrofuran-3-yl]pyrazolo[4,3-b]pyridin-7-amine | 2004 | 690 | 3549 |
| 28 | 1-isopropyl-5-(2-methoxy-3-pyridyl)-N-[(3R)-tetrahydrofuran-3-yl]pyrazolo[4,3-b]pyridin-7-amine | 533 | 124 | 1081 |
| 29 | 1-isopropyl-5-(2-methoxy-6-methyl-3-pyridyl)-N-[(3R)-tetrahydrofuran-3-yl]pyrazolo[4,3-b]pyridin-7-amine | 31% @ 10 μM | 1693 | 68% @ 10 μM |
| 30 | 1-isopropyl-5-(3-methoxy-4-pyridyl)-N-[(3R)-tetrahydrofuran-3-yl]pyrazolo[4,3-b]pyridin-7-amine | 1554 | 236 | 2561 |
| 31 | 1-isopropyl-5-(4-methoxy-3-pyridyl)-N-[(3R)-tetrahydrofuran-3-yl]pyrazolo[4,3-b]pyridin-7-amine | 63% @ 10 μM | 1227 | 76% @ 10 μM |
| 32 | 5-(1,3-benzodioxol-4-yl)-1-isopropyl-N-[(3R)-tetrahydrofuran-3-yl]pyrazolo[4,3-b]pyridin-7-amine | 1294 | 284 | 1200 |
| 33 | 5-(4-ethoxyphenyl)-1-isopropyl-N-[(3R)-tetrahydrofuran-3-yl]pyrazolo[4,3-b]pyridin-7-amine | 20% @ 10 μM | 46% @ 10 μM | 24% @ 10 μM |
| 34 | 5-(2-ethoxy-4-methyl-3-pyridyl)-1-isopropyl-N-[(3R)-tetrahydrofuran-3-yl]pyrazolo[4,3-b]pyridin-7-amine | 380 | 157 | 580 |
| 35 | 1-isopropyl-5-pyrazolo[1,5-a]pyridin-3-yl-N-[(3R)-tetrahydrofuran-3-yl]pyrazolo[4,3-b]pyridin-7-amine | 1621 | 604 | 2143 |
| 36 | 5-(2-tert-butoxy-3-pyridyl)-1-isopropyl-N-[(3R)-tetrahydrofuran-3-yl]pyrazolo[4,3-b]pyridin-7-amine | 260 | 91 | 3228 |
| 37 | 1-isopropyl-5-[(3-methoxyphenyl)methyl]-N-[(3R)-tetrahydrofuran-3-yl]pyrazolo[4,3-b]pyridin-7-amine | 60% @ 10 μM | 1336 | 1675 |
| 38 | 5-(2,5-dimethoxy-4-pyridyl)-1-isopropyl-N-[(3R)-tetrahydrofuran-3-yl]pyrazolo[4,3-b]pyridin-7-amine | 1160 | 308 | 566 |
| 39 | 1-isopropyl-5-(3-methyl-2-pyridyl)-N-[(3R)-tetrahydrofuran-3-yl]pyrazolo[4,3-b]pyridin-7-amine | 61% @ 10 μM | 1890 | 59% @ 10 μM |

TABLE 1-continued

Compounds of the invention

| Example | Compound | PDE1 A, IC$_{50}$ (nM) | PDE1 B, IC$_{50}$ (nM) | PDE1 C, IC$_{50}$ (nM) |
|---|---|---|---|---|
| 40 | 1-isopropyl-5-(3-methoxy-2-pyridyl)-N-[(3R)-tetrahydrofuran-3-yl]pyrazolo[4,3-b]pyridin-7-amine | 81% @ 10 μM | 2140 | 26% @ 10 μM |
| 41 | 2-[1-isopropyl-7-[[(3R)-tetrahydrofuran-3-yl]amino]pyrazolo[4,3-b]pyridin-5-yl]benzonitrile | 951 | 248 | 1714 |
| 42 | 5-(2,3-dihydro-1,4-benzodioxin-5-yl)-1-isopropyl-N-[(3R)-tetrahydrofuran-3-yl]pyrazolo[4,3-b]pyridin-7-amine | 1570 | 546 | 68% @ 10 μM |
| 43 | 5-[(4-fluorophenyl)methyl]-1-isopropyl-N-[(3R)-tetrahydrofuran-3-yl]pyrazolo[4,3-b]pyridin-7-amine | 2856 | 1224 | 621 |
| 44 | 5-[1-isopropyl-7-[[(3R)-tetrahydrofuran-3-yl]amino]pyrazolo[4,3-b]pyridin-5-yl]pyridine-3-carbonitrile | 33% @ 10 μM | 4010 | 47% @ 10 μM |
| 45 | 1-isopropyl-5-[3-(methoxymethyl)phenyl]-N-[(3R)-tetrahydrofuran-3-yl]pyrazolo[4,3-b]pyridin-7-amine | 2480 | 341 | 72% @ 10 μM |
| 46 | 5-(5-ethoxy-3-pyridyl)-1-isopropyl-N-[(3R)-tetrahydrofuran-3-yl]pyrazolo[4,3-b]pyridin-7-amine | 51% @ 10 μM | 1571 | 2918 |
| 47 | 1-isopropyl-5-(5-methoxy-3-pyridyl)-N-[(3R)-tetrahydrofuran-3-yl]pyrazolo[4,3-b]pyridin-7-amine | 1520 | 599 | 1546 |
| 48 | 5-[3-(difluoromethoxy)phenyl]-1-isopropyl-N-[(3R)-tetrahydrofuran-3-yl]pyrazolo[4,3-b]pyridin-7-amine | 1099 | 384 | 1727 |
| 49 | 1-isopropyl-5-(4-methoxypyrimidin-5-yl)-N-[(3R)-tetrahydrofuran-3-yl]pyrazolo[4,3-b]pyridin-7-amine | 43% @ 10 μM | 2667 | 1868 |
| 50 | 5-(4-ethoxypyrimidin-5-yl)-1-isopropyl-N-[(3R)-tetrahydrofuran-3-yl]pyrazolo[4,3-b]pyridin-7-amine | 2995 | 916 | 1813 |
| 51 | 1-isopropyl-5-(5-methoxy-2-methyl-3-pyridyl)-N-[(3R)-tetrahydrofuran-3-yl]pyrazolo[4,3-b]pyridin-7-amine | 20% @ 10 μM | 3247 | 3849 |
| 52 | 1-isopropyl-5-(2-methoxy-5-methyl-3-pyridyl)-N-[(3R)-tetrahydrofuran-3-yl]pyrazolo[4,3-b]pyridin-7-amine | 56% @ 10 μM | 1317 | 1817 |
| 53 | 5-(2-ethoxyphenyl)-1-isopropyl-N-[(3R)-tetrahydrofuran-3-yl]pyrazolo[4,3-b]pyridin-7-amine | 73% @ 10 μM | 299 | 61% @ 10 μM |
| 54 | 5-[1-isopropyl-7-[[(3R)-tetrahydrofuran-3-yl]amino]pyrazolo[4,3-b]pyridin-5-yl]-6-methoxy-pyridine-3-carbonitrile | 59% @ 10 μM | 1528 | 2397 |
| 55 | 6-ethoxy-5-[1-isopropyl-7-[[(3R)-tetrahydrofuran-3-yl]amino]pyrazolo[4,3-b]pyridin-5-yl]pyridine-3-carbonitrile | 69% @ 10 μM | 1379 | 2500 |
| 56 | 5-(2-ethyl-3-pyridyl)-1-isopropyl-N-[(3R)-tetrahydrofuran-3-yl]pyrazolo[4,3-b]pyridin-7-amine | 51% @ 10 μM | 1525 | 59% @ 10 μM |
| 57 | 1-isopropyl-5-[(4-methoxyphenyl)methyl]-N-[(3R)-tetrahydrofuran-3-yl]pyrazolo[4,3-b]pyridin-7-amine | 874 | 303 | 506 |
| 58 | 1-isopropyl-5-[2-(methoxymethyl)-3-pyridyl]-N-[(3R)-tetrahydrofuran-3-yl]pyrazolo[4,3-b]pyridin-7-amine | 52% @ 10 μM | 2192 | 31% @ 10 μM |
| 59 | 5-(2-ethoxy-3-pyridyl)-1-isopropyl-3-methyl-pyrazolo[4,3-b]pyridine | 52 | 26 | 180 |
| 60 | 1-isopropyl-3,6-dimethyl-5-phenyl-pyrazolo[4,3-b]pyridine | 225 | 122 | 198 |
| 61 | 1-isopropyl-5-(2-methoxy-3-pyridyl)-3,6-dimethyl-pyrazolo[4,3-b]pyridine | 288 | 84 | 236 |
| 62 | 1-isopropyl-5-(2-methoxyphenyl)-3,6-dimethyl-pyrazolo[4,3-b]pyridine | 694 | 159 | 568 |
| 63 | 5-(2-ethoxy-3-pyridyl)-1-isopropyl-3,6-dimethyl-pyrazolo[4,3-b]pyridine | 86 | 16 | 175 |
| 64 | 1-isopropyl-3,6-dimethyl-5-(2-propoxy-3-pyridyl)pyrazolo[4,3-b]pyridine | 118 | 25 | 220 |
| 65 | 5-(2-ethoxy-3-pyridyl)-1-isopropyl-N,3-dimethyl-pyrazolo[4,3-b]pyridin-7-amine | 50 | 7 | 111 |
| 66 | 5-(2-ethoxy-3-pyridyl)-N-ethyl-1-isopropyl-3-methyl-pyrazolo[4,3-b]pyridin-7-amine | 60 | 5 | 161 |

TABLE 1-continued

Compounds of the invention

| Example | Compound | PDE1 A, IC$_{50}$ (nM) | PDE1 B, IC$_{50}$ (nM) | PDE1 C, IC$_{50}$ (nM) |
|---|---|---|---|---|
| 67 | (±)-5-[[[5-(2-ethoxy-3-pyridyl)-1-isopropyl-3-methyl-pyrazolo[4,3-b]pyridin-7-yl]amino]methyl]-1-methyl-pyrrolidin-2-one | 70 | 11 | 106 |
| 68 | 4-[[[5-(2-ethoxy-3-pyridyl)-1-isopropyl-3-methyl-pyrazolo[4,3-b]pyridin-7-yl]amino]methyl]-1-methyl-pyrrolidin-2-one | 53 | 12 | 88 |
| 69 | 5-(2-ethoxy-3-pyridyl)-1-isopropyl-3-methyl-pyrazolo[4,3-b]pyridin-7-amine | 62 | 13 | 129 |
| 70 | 5-(2-ethoxy-3-pyridyl)-1-isopropyl-pyrazolo[4,3-b]pyridine | 836 | 99 | 2168 |
| 71 | 2-(2-ethoxy-3-pyridyl)-6-isopropyl-3,8-dimethyl-imidazo[1,5-a]pyrimidine | 74 | 17 | 99 |
| 72 | 2-(2-ethoxy-3-pyridyl)-6-isopropyl-8-methyl-imidazo[1,5-a]pyrimidine | 96 | 34 | 213 |
| 73 | 6-cyclobutyl-2-(2-ethoxy-3-pyridyl)-8-methyl-imidazo[1,5-a]pyrimidine | 1554 | 296 | 2086 |
| 74 | 6-cyclopropyl-2-(2-ethoxy-3-pyridyl)-8-methyl-imidazo[1,5-a]pyrimidine | 394 | 121 | 1184 |
| 75 | 2-(2-ethoxy-3-pyridyl)-6-(1-ethylpropyl)-8-methyl-imidazo[1,5-a]pyrimidine | 244 | 36 | 394 |
| 76 | (±)-2-(2-ethoxy-3-pyridyl)-8-methyl-6-sec-butyl-imidazo[1,5-a]pyrimidine | 61 | 9 | 112 |
| 77 | 2-(2-ethoxy-3-pyridyl)-8-methyl-6-(3-methyloxetan-3-yl)imidazo[1,5-a]pyrimidine | 448 | 239 | 730 |
| 78 | 2-(2-ethoxy-3-pyridyl)-8-methyl-6-(2,2,2-trifluoroethyl)imidazo[1,5-a]pyrimidine | 321 | 207 | 717 |
| 79 | 2-(2-ethoxy-3-pyridyl)-8-methyl-6-(oxetan-3-yl)imidazo[1,5-a]pyrimidine | 406 | 78 | 632 |
| 80 | 6-cyclopentyl-2-(2-ethoxy-3-pyridyl)-8-methyl-imidazo[1,5-a]pyrimidine | 3232 | 591 | 2285 |
| 81 | (±)-2-(2-ethoxy-3-pyridyl)-8-methyl-6-tetrahydrofuran-3-yl-imidazo[1,5-a]pyrimidine | 1126 | 145 | 1632 |
| 82 | 6-tert-butyl-2-(2-ethoxy-3-pyridyl)-8-methyl-imidazo[1,5-a]pyrimidine | 29% @ 10 µM | 54% @ 10 µM | 28% @ 10 µM |
| 83 | 2-(2-ethoxy-3-pyridyl)-8-methyl-6-[1-methylpropyl]imidazo[1,5-a]pyrimidine, enantiomer 1 | 51 | 6 | 77 |
| 84 | 2-(2-ethoxy-3-pyridyl)-8-methyl-6-[1-methylpropyl]imidazo[1,5-a]pyrimidine, enantiomer 2 | 159 | 33 | 323 |
| 85 | 5-(2-ethoxy-3-pyridyl)-7-[(3R)-3-methoxypyrrolidin-1-yl]-1-methyl-pyrazolo[4,3-b]pyridine | 23% @ 1 µM | 536 | 56% @ 1 µM |
| 86 | 5-(2-ethoxy-3-pyridyl)-N-[(1R,2R)-2-methoxycyclopentyl]-1-methyl-pyrazolo[4,3-b]pyridin-7-amine | 22% @ 1 µM | 536 | 20% @ 1 µM |
| 87 | (±)-5-(2-ethoxy-3-pyridyl)-7-(3-fluoro-3-methyl-pyrrolidin-1-yl)-1-methyl-pyrazolo[4,3-b]pyridine | 42% @ 1 µM | 376 | 26% @ 1 µM |
| 88 | 5-(2-ethoxy-3-pyridyl)-N-(3-methoxycyclopentyl)-1-methyl-pyrazolo[4,3-b]pyridin-7-amine | 16% @ 1 µM | 311 | 47% @ 1 µM |

Table 1 lists the IC$_{50}$ values for inhibition of PDE1 by the compounds of the invention. The IC$_{50}$ value refers to the concentration (nM) of the compound required to reach 50% inhibition of the PDE1 enzyme at the specified substrate concentration. PDE1 assays are described in the Experimental Section.

EXPERIMENTAL SECTION

Preparation of the Compounds of the Invention—General Methods

The compounds of formula (I) may be prepared by methods described below, together with synthetic methods known in the art of organic chemistry, or modifications that are familiar to those of ordinary skill in the art. The starting materials used herein are available commercially or may be prepared by routine methods known in the art, such as those methods described in standard reference books such as "Compendium of Organic Synthetic Methods, Vol. I-XIII" (published with Wiley-Interscience, ISSN: 1934-4783). Preferred methods include, but are not limited to, those described below.

The schemes are representative of methods useful in synthesizing the compounds of the present invention. They are not to constrain the scope of the invention in any way.

Method 1:

Scheme 1

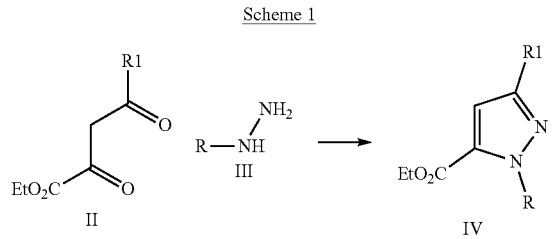

where R1 is as described for formula I and R is hydrogen or R is R2 as described for formula I.

Compounds of general formula IV (Scheme 1) can be prepared from compounds of general formula II and III.

Method 2:

Scheme 2

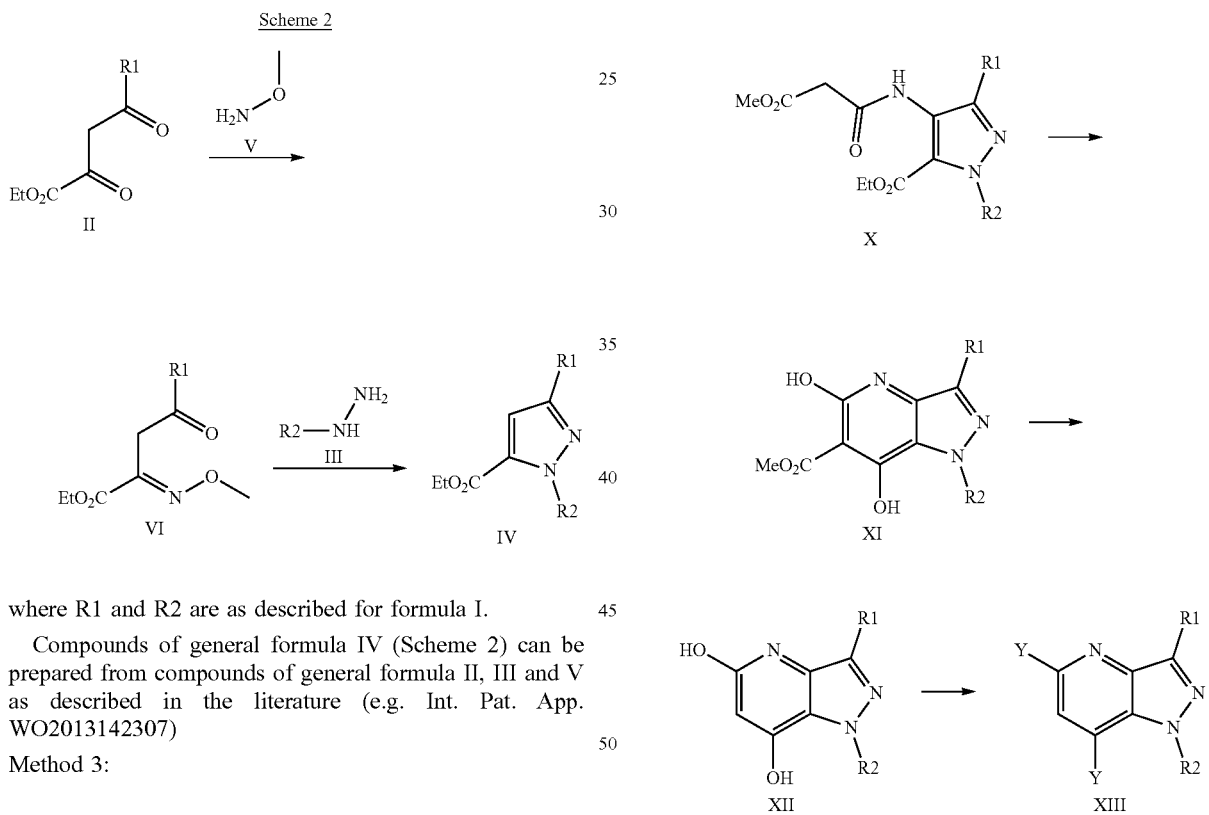

where R1 and R2 are as described for formula I.

Compounds of general formula IV (Scheme 2) can be prepared from compounds of general formula II, III and V as described in the literature (e.g. Int. Pat. App. WO2013142307)

Method 3:

Scheme 3

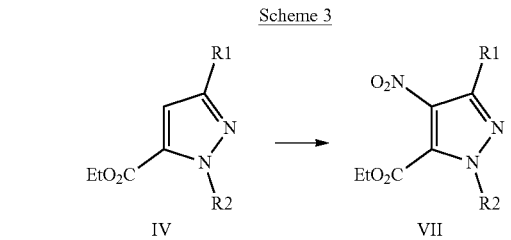

where R1 and R2 is are described for formula I.

Compounds of general formula VII (Scheme 3) can be prepared by nitration of compounds of general formula IV.

Method 4:

Scheme 4 where R1 and R2 are as described for formula I and Y is a halogen such as chlorine or bromine.

Compounds of general formula VIII (Scheme 4) can be prepared by reduction of compounds of general formula VII. Compounds of general formula XI can be prepared by reaction of compounds of general formula VIII with methyl 3-chloro-3-oxopropanoate followed by ring-closure in the presence of a base such as sodium ethoxide or sodium methoxide. Hydrolysis and decarboxylation of compounds of general formula XI followed by treatment with phosphoryl trichloride or phosphoryl tribromide gives compounds of general formula XIII.

Method 5:

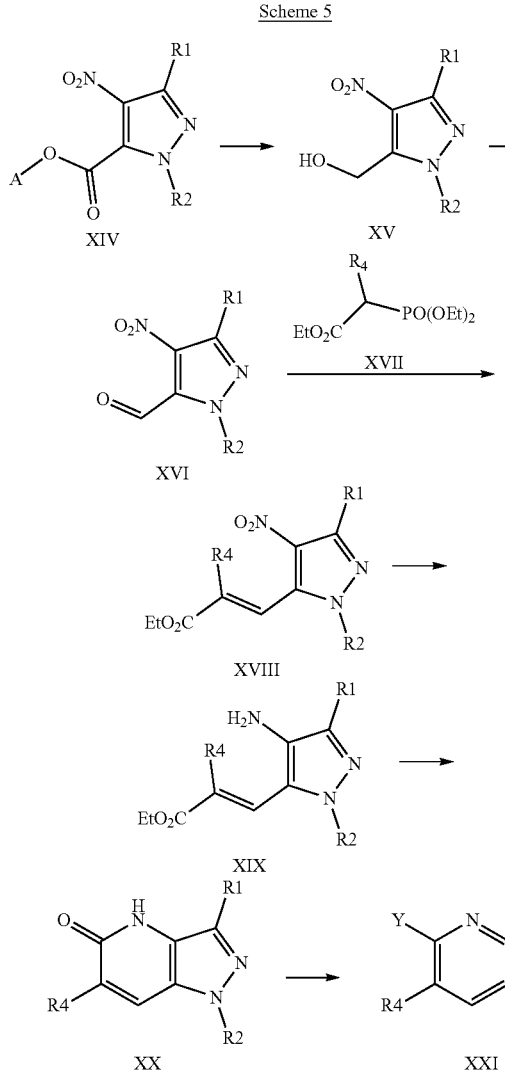

where R1, R2 and R4 are as described for formula I, A is an alkyl group such as methyl or ethyl and Y is a halogen such as chlorine or bromine.

Compounds of general formula XV (Scheme 5) can be prepared by reduction of compounds of general formula XIV with a reagent such as borane. Compounds of general formula XV can be oxidized to compounds of general formula XVI by treatment with an oxidant such as the Dess-Martin periodinane (1,1,1-triacetoxy-1,1-dihydro-1,2-benziodoxol-3(1H)-one). Compounds of general formula XVIII can be prepared by treatment of compounds of general formula XVI with compounds of general formula XVII in the presence of LiCl and as base such as DIPEA (N,N-diisopropylethylamine). Selective reduction of the nitro moiety with reagents such as iron and ammonium chloride gives compounds of general formula XIX. Treatment of compounds of general formula XIX with a reagent such as tributylphosphine or iodine leads to double bond isomerization and ring-closure to form compounds of general formula XX followed by treatment with phosphoryl trichloride or phosphoryl tribromide gives compounds of general formula XXI.

Method 6:

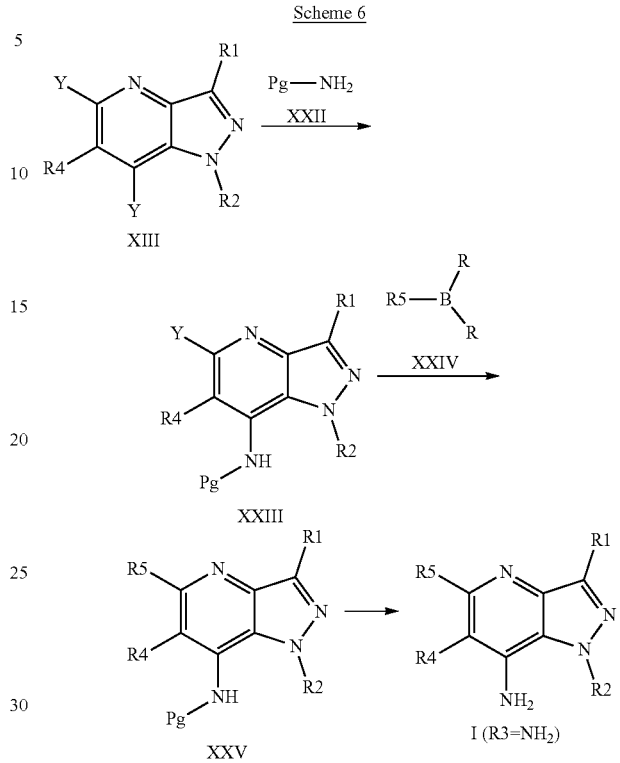

where R1, R2, R4 and R5 are as described for formula I, R are hydroxy groups or R together with the boron atom form a 4,4,5,5-tetramethyl-1,3,2-dioxaborolane group and Pg is a protection group such as para-methoxy benzyl. Y is a halogen such as chlorine or bromine.

Compounds of general formula XXIII (Scheme 6) can be prepared by treatment of compounds of general formula XIII with compounds of general formula XXII in the presence of a base such as but not limited to cesium fluoride or N,N-diisopropylethylamine. Compounds of general formula XXV can be prepared from compounds of general formulae XXIII and XXIV in the presence of a palladium catalyst such as [1,1'-bis(diphenylphosphino)ferrocene]palladium (II) dichloride and a base such as potassium carbonate or other Suzuki-Miyaura coupling reaction conditions known to chemists skilled in the art of organic synthesis. Compounds of general formula I (R3=NH$_2$) can be prepared deprotection of compounds of general formula XXV. If the protection group is para-methoxy benzyl, the deprotection can be performed by treatment with an acid such as trifluoroacetic acid.

Method 7:

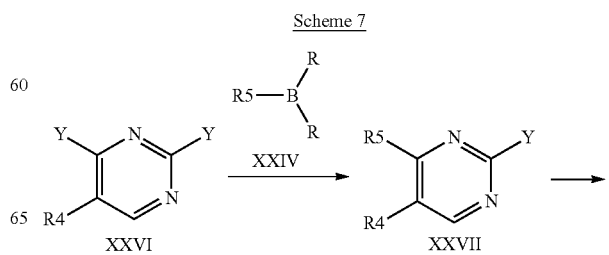

-continued

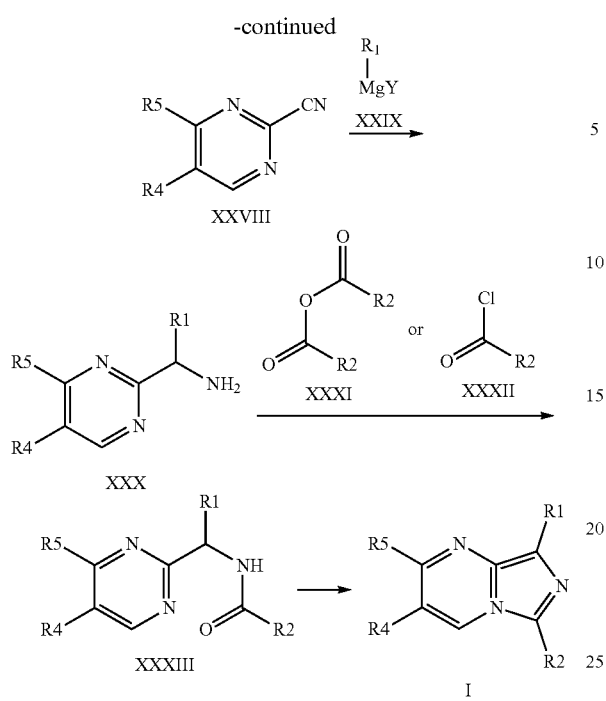

where R1, R2, R3, R4 and R5 are as described for formula I, R are hydroxy groups or R together with the boron atom form a 4,4,5,5-tetramethyl-1,3,2-dioxaborolane group.

Compounds of general formula XXVII (Scheme 7) can be prepared from compounds of general formulae XXVI and XXIV in the presence of a palladium catalyst such as [1,1'-bis(diphenylphosphino)ferrocene]palladium(II) dichloride and a base such as potassium carbonate or other Suzuki-Miyaura coupling reaction conditions known to chemists skilled in the art of organic synthesis. Treatment of compounds of general formula XXVII with reagents such as NaCN and DABCO (1,4-diazabicyclo[2.2.2]octane) gives compounds of general formula XXVIII. Addition of a reagent such as XXIX to compounds of general formula XXVIII followed by reduction with a reagent such as NaBH₄ gives compounds of general formula XXX. Compounds of general formula XXXIII are obtained by reaction of compounds of general formula XXX with acid anhydrides such as XXXI or acid chlorides such as XXXII. Treatment of compounds of general formula XXXIII with reagents such as triflic anhydride and 2-methoxy pyridine gives compounds of general formula I.

Method 8:

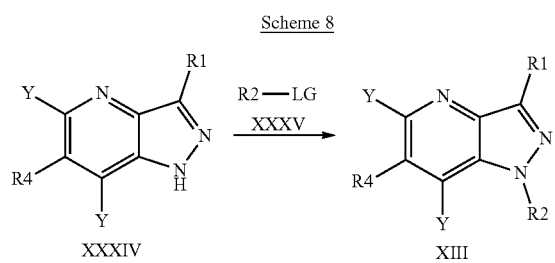

where R1, R2 and R4 are as described for formula I, Y is a halogen such as chlorine or bromine, LG is a leaving group such as OH or a halogen such as chlorine, bromine or iodine.

Compounds of general formula XIII (Scheme 8) can be prepared by alkylation of compounds of general formula XXXIV with compounds of general formula XXXV. When LG is a halogen such as chlorine, bromine or iodine the reaction can be done in the presence of a base such as Cs₂CO₃. When LG is a OH the reaction can be done in the presence of reagents such as diisopropyl azodicarboxylate and triphenylphosphine.

Method 9:

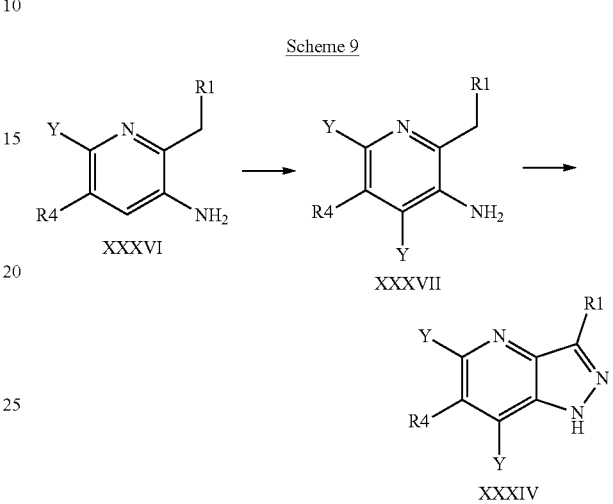

where R1 and R4 are as described for formula I, Y is a halogen such as chlorine or bromine.

Compounds of general formula XXXVII (Scheme 9) can be prepared by treatment of compounds of general formula XXXVI with a reagent such as bromine. Treatment of compounds of general formula XXVII with a reagent such as isopentyl nitrite gives compounds of general formula XXXIV.

Method 10:

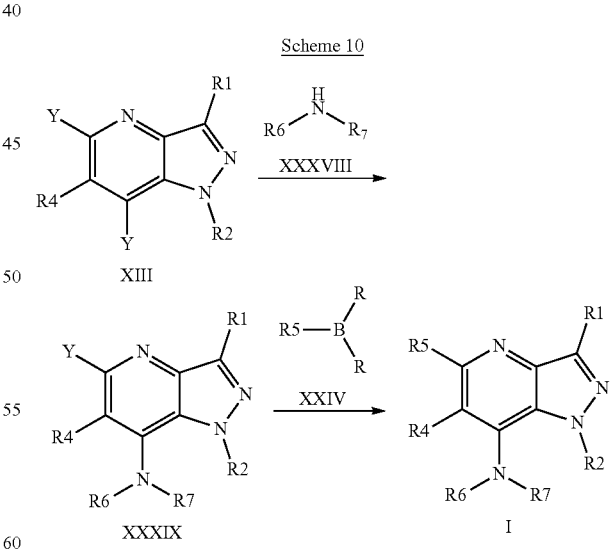

where R1, R2, R4, R5, R6 and R7 are as described for formula I, R are hydroxy groups or R together with the boron atom form a 4,4,5,5-tetramethyl-1,3,2-dioxaborolane group. Y is a halogen such as chlorine or bromine.

Compounds of general formula XXXIX (Scheme 10) can be prepared by treatment of compounds of general formula XIII with compounds of general formula XXXVIII in the presence of a base such as but not limited to cesium fluoride or N,N-diisopropylethylamine. Compounds of general formula I can be prepared from compounds of general formulae XXXIX and XXIV in the presence of a palladium catalyst such as [1,1'-bis(diphenylphosphino)ferrocene]palladium (II) dichloride and a base such as potassium carbonate or other Suzuki-Miyaura coupling reaction conditions known to chemists skilled in the art of organic synthesis.

Method 11:

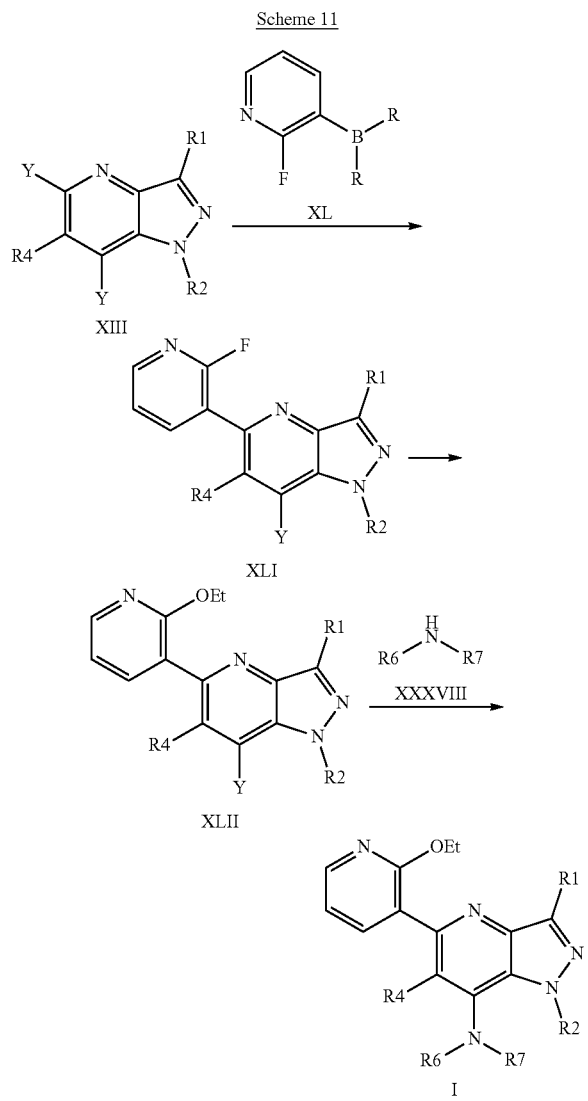

Scheme 11 where R1, R2, R4, R6 and R7 are as described for formula I, R are hydroxy groups or R together with the boron atom form a 4,4,5,5-tetramethyl-1,3,2-dioxaborolane group. Y is a halogen such as chlorine or bromine.

Compounds of general formula XLI (Scheme 11) can be prepared from compounds of general formulae XIII and XL in the presence of a palladium catalyst such as [1,1'-bis(diphenylphosphino)ferrocene]palladium(II) dichloride and a base such as potassium carbonate or other Suzuki-Miyaura coupling reaction conditions known to chemists skilled in the art of organic synthesis. A substitution reaction with ethanol and a base such as sodium hydride converts compounds of general formula XLI to compounds of general formula XLII. A coupling reaction of compounds of general formula XLII with amines of general formula XXXVIII in the presence of a catalyst such as $Pd_2(dba)_3$ (dba=dibenzylidene acetone) and BINAP (BINAP=2,2'-bis (diphenylphosphino)-1,1'-binaphthyl) and a base such as KOtBu gives compounds of general formula I.

Preparation of Intermediates

LC-MS Methods

Method A: An Agilent 1200 LCMS system with ELS detector was used. Phenomenex Luna-C18, 5 μm; 2.0×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=90:10 to 0:100 in 4.0 minutes and with a flow rate of 0.8 mL/min.

Method B: An Agilent 1200 LCMS system with ELS detector was used. Column: Waters XBridge ShieldRP18, 2.1×50 mm, 5 μm; Column temperature: 40° C.; Solvent system: A=water/ammonia (99.95:0.05) and B=acetonitrile; Method: Linear gradient elution with A:B=95:5 to 0:100 in 4.0 minutes and with a flow rate of 0.8 mL/min.

Method C: An Agilent 1200 LCMS system with ELS detector was used. Phenomenex Luna-C18, 5 μm; 2.0×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=99:1 to 0:100 in 4.0 minutes and with a flow rate of 0.8 mL/min.

Method D: A Waters Acquity UPLC-MS was used. Column: Acquity UPLC BEH C18 1.7 μm; 2.1×50 mm; Column temperature: 60° C.; Solvent system: A=water/trifluoroacetic acid (99.965:0.035) and B=acetonitrile/water/trifluoroacetic acid (94.965:5:0.035); Method: Linear gradient elution with A:B=90:10 to 0:100 in 1.0 minutes and with a flow rate of 1.2 mL/min.

Method E: A Waters Acquity UPLC-MS was used. Column: Acquity UPLC BEH C18 1.7 μm; 2.1×50 mm; Column temperature: 60° C.; Solvent system: A=water/formic acid (99.9:0.1) and B=acetonitrile/water/formic acid (94.9:5:0.1); Method: Linear gradient elution with A:B=90:10 to 0:100 in 1.0 minutes and with a flow rate of 1.2 mL/min.

Method F: An Agilent 1200 LCMS system with ELS detector was used. Column: Waters XBridge ShieldRP18, 2.1×50 mm, 5 μm; Column temperature: 40° C.; Solvent system: A=water/ammonia (99.95:0.05) and B=acetonitrile; Method: Linear gradient elution with A:B=85:15 to 0:100 in 3.4 minutes and with a flow rate of 0.8 mL/min.

Method G: An Agilent 1200 LCMS system with ELS detector was used. Column: Agilent TC-C18 5 μm; 2.1×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=99:1 to 0:100 in 4.0 minutes and with a flow rate of 0.8 mL/min.

Method J: A Waters Acquity UPLC-MS was used. Column: Acquity UPLC BEH C18 1.7 μm; 2.1×50 mm; Column temperature: 60° C.; Solvent system: A=water/trifluoroacetic acid (99.965:0.035) and B=acetonitrile/water/trifluoroacetic acid (94.965:5:0.035); Method: Linear gradient elution with A:B=98:2 to 0:100 in 1.0 minutes and with a flow rate of 1.2 mL/min.

Method K: An Agilent 1200 LCMS system with ELS detector was used. Column: Agilent TC-C18 5 μm; 2.1×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=90:10 to 0:100 in 4.0 minutes and with a flow rate of 0.8 mL/min.

Preparation of ethyl 2-(methoxyimino)-4-oxopentanoate

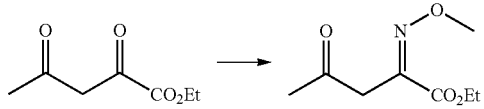

A mixture of ethyl 2,4-dioxopentanoate (27 g, 171 mmol, 24 mL) and methoxylamine (15 g, 179 mmol, 13.6 mL) in ethanol (150 mL) was stirred at 25° C. for 18 hours under a nitrogen atmosphere. The mixture was concentrated. The crude mixture was purified by flash silica gel chromatography with petroleum ether:ethyl acetate=10:1 to give the title compound.

Preparation of ethyl 1-isopropyl-3-methyl-1H-pyrazole-5-carboxylate

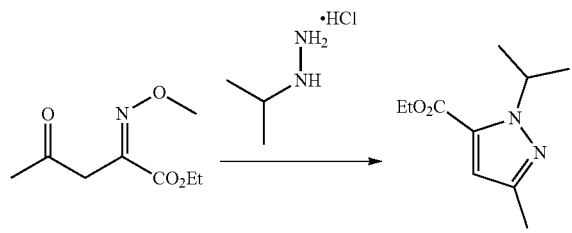

To a solution of ethyl 2-(methoxyimino)-4-oxopentanoate (14.6 g, 78.0 mmol) in ethanol (200 mL) was added isopropylhydrazine hydrochloride (17.25 g, 156 mmol). The mixture was stirred at 80° C. for 18 hours. The mixture was concentrated. Saturated aqueous NaHCO$_3$ was added into the residue to adjust the pH to 7. Then the mixture was extracted with dichloromethane (100 mL×3), the combined organic layers were washed with brine, dried over Na$_2$SO$_4$ and concentrated. The crude mixture was purified by flash silica gel chromatography with petroleum ether:ethyl acetate=10:1 to give ethyl 1-isopropyl-3-methyl-1H-pyrazole-5-carboxylate. $^1$H NMR (chloroform-d 400 MHz): δ 6.59 (s, 1H), 5.41-5.44 (m, 1H), 4.35-4.29 (m, 2H), 2.29 (s, 3H), 1.48 (d, J=6.8 Hz, 6H), 1.39-1.35 (m, 3H).

Preparation of ethyl 1-isopropyl-3-methyl-4-nitro-1H-pyrazole-5-carboxylate

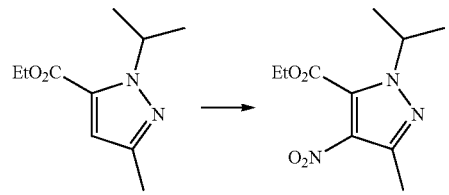 [SMILES: CCOC(=O)c1cc(C)nn1C(C)C ; CCOC(=O)c1c([N+](=O)[O-])c(C)nn1C(C)C]

To a solution of ethyl 1-isopropyl-3-methyl-1H-pyrazole-5-carboxylate (8 g, 40.8 mmol) and (2,2,2-trifluoroacetyl) 2,2,2-trifluoroacetate (59.9 g, 285.4 mmol, 39.7 mL) in TFA (80 mL) was added ammonium nitrate (6.5 g, 81.5 mmol, 3.8 mL) slowly at 0° C. The mixture was stirred at 20° C. for 18 hours. The solution was cooled to 0° C. and then neutralized with aqueous K$_2$CO$_3$ and the product was extracted with ethyl acetate:dichloromethane=40:1 (205 mL×4). The combined organic layers were washed with brine (150 mL), dried over Na$_2$SO$_4$ and concentrated to give ethyl 1-isopropyl-3-methyl-4-nitro-1H-pyrazole-5-carboxylate.

Preparation of (1-ethyl-3-methyl-4-nitro-1H-pyrazol-5-yl)methanol

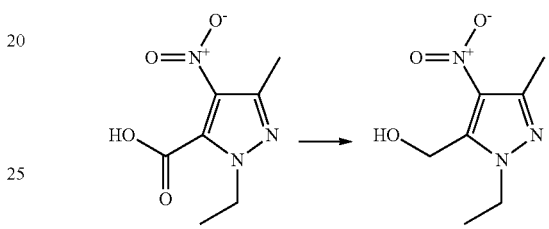

Borane tetrahydrofuran complex (19 ml, 19 mmol, 1 molar, THF) was added to 1-ethyl-3-methyl-4-nitro-1H-pyrazole-5-carboxylic acid (1.13 g, 5.67 mmol) in THF (25 mL) at 0° C. The reaction mixture was stirred at 0° C. for 1 hour, then heated to reflux overnight. Borane tetrahydrofuran complex (10 ml, 10 mmol, 1 molar, THF) was added. The reaction mixture was heated to reflux for 5 hours. The reaction mixture was cooled on ice bath. Water was added. The mixture was extracted with ethyl acetate. The organic phase was washed with brine, dried over MgSO$_4$ and concentrated in vacuo to give the title compound which was used in the next step without further purification.

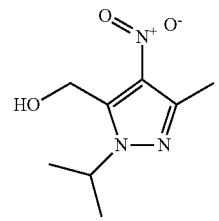

(1-isopropyl-3-methyl-4-nitro-1H-pyrazol-5-yl)methanol was prepared in a similar way from 1-isopropyl-3-methyl-4-nitro-1H-pyrazole-5-carboxylic acid Preparation of 1-ethyl-3-methyl-4-nitro-1H-pyrazole-5-carbaldehyde

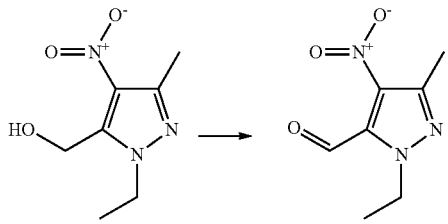

Dess-Martin Periodinane (1.80 g, 4.25 mmol) was added to (1-ethyl-3-methyl-4-nitro-1H-pyrazol-5-yl)methanol (524 mg, 2.83 mmol) in dichloromethane (10 mL). Water (56 µL) was added. The reaction mixture was stirred at room temperature overnight. 50 mL 10% $Na_2S_2O_3$ (aq) and 50 mL sat. $NaHCO_3$ (aq) were added. The reaction mixture was stirred at room temperature for 1 hour. The mixture was extracted with ethyl acetate. The organic phase was washed with brine, dried over $MgSO_4$ and concentrated in vacuo. The crude material was purified via flash chromatography on silica gel (ethyl acetate/heptane) to afford the title compound.

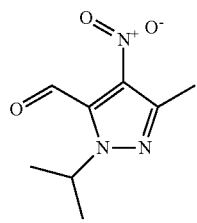

1-isopropyl-3-methyl-4-nitro-1H-pyrazole-5-carbaldehyde was prepared in a similar way from (1-isopropyl-3-methyl-4-nitro-1H-pyrazol-5-yl)methanol Preparation of methyl (E)-ethyl 3-(1-ethyl-3-methyl-4-nitro-1H-pyrazol-5-yl)-2-methylacrylate

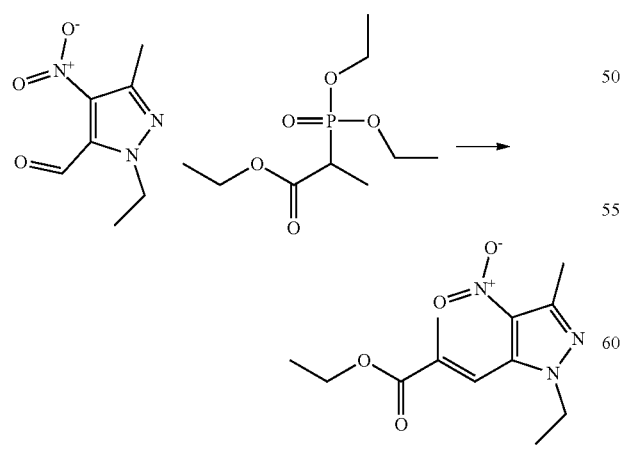

Ethyl 2-(diethoxyphosphoryl)propanoate (177 mg, 160 µl, 0.744 mmol) and lithium chloride (112 mg, 2.64 mmol) were added to 1-ethyl-3-methyl-4-nitro-1H-pyrazole-5-carbaldehyde (125 mg, 0.682 mmol) and diisopropyl ethylamine (125 mg, 169 µl, 0.970 mmol) in acetonitrile (2 mL). The reaction mixture was stirred at room temperature overnight. The reaction mixture was concentrated in vacuo. Water was added. The mixture was extracted with ethyl acetate. The organic phase was washed with brine, dried over $MgSO_4$ and concentrated in vacuo. The crude material was purified via flash chromatography on silica gel (etyl acetate/heptane) to afford the title compound.

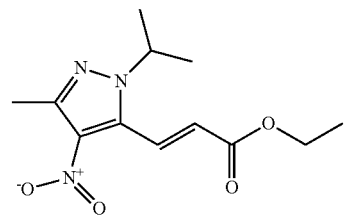

ethyl 3-(1-isopropyl-3-methyl-4-nitro-1H-pyrazol-5-yl) acrylate was prepared in a similar way from 1-isopropyl-3-methyl-4-nitro-1H-pyrazole-5-carbaldehyde and ethyl 2-(diethoxyphosphoryl)acetate

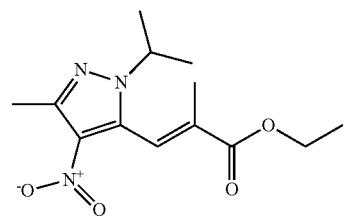

ethyl 3-(1-isopropyl-3-methyl-4-nitro-1H-pyrazol-5-yl)-2-methylacrylate was prepared in a similar way from 1-isopropyl-3-methyl-4-nitro-1H-pyrazole-5-carbaldehyde and ethyl 2-(diethoxyphosphoryl)propanoate Preparation of (E)-ethyl 3-(4-amino-1-ethyl-3-methyl-1H-pyrazol-5-yl)-2-methylacrylate

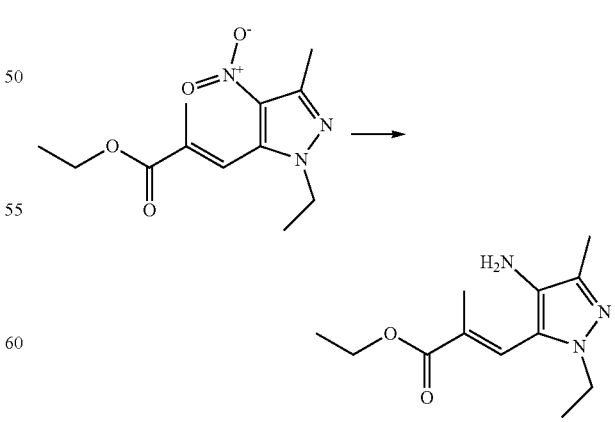

Iron (400 mg, 7.16 mmol) was added to (E)-ethyl 3-(1-ethyl-3-methyl-4-nitro-1H-pyrazol-5-yl)-2-methylacrylate (70 mg, 0.262 mmol) in methanol (1 ml). Saturated aqueous ammonium chloride (1 ml) was added. The reaction mixture was stirred at 80° C. overnight. The reaction mixture was filtered and concentrated in vacuo. Water was added. The mixture was extracted with ethyl acetate. The organic phase was washed with brine, dried over MgSO$_4$ and concentrated in vacuo to give (E)-ethyl 3-(4-amino-1-ethyl-3-methyl-1H-pyrazol-5-yl)-2-methylacrylate (as a mixture of methyl- and ethyl esters) which was used in the next step without further purification.

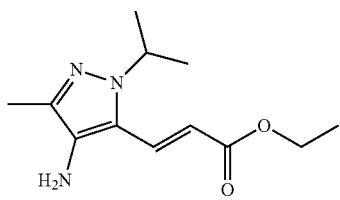 [SMILES: CCOC(=O)/C=C/c1c(N)c(C)nn1C(C)C]

ethyl 3-(4-amino-1-isopropyl-3-methyl-1H-pyrazol-5-yl)acrylate was prepared in a similar way from ethyl 3-(1-isopropyl-3-methyl-4-nitro-1H-pyrazol-5-yl)acrylate

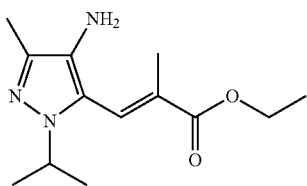 [SMILES: CCOC(=O)/C(C)=C/c1c(N)c(C)nn1C(C)C]

ethyl 3-(4-amino-1-isopropyl-3-methyl-1H-pyrazol-5-yl)-2-methylacrylate was prepared in a similar way from ethyl 3-(1-isopropyl-3-methyl-4-nitro-1H-pyrazol-5-yl)-2-methylacrylate Preparation of 1-ethyl-3,6-dimethyl-1H-pyrazolo[4,3-b]pyridin-5(4H)-one

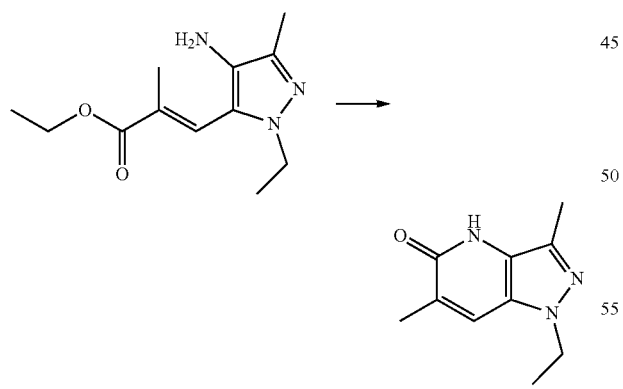

Iodine (0.5 mg, 2 µmol) was added to (E)-ethyl 3-(4-amino-1-ethyl-3-methyl-1H-pyrazol-5-yl)-2-methylacrylate (55 mg, 0.232 mmol) (as a mixture of methyl- and ethyl esters) in toluene (1.2 mL). The reaction mixture was stirred at 140° C. for 3 hours Iodine (0.5 mg, 2 µmop was added. The reaction mixture was stirred at 130° C. for 3 days. 10% aqueous Na$_2$S$_2$O$_3$ was added at room temperature. The mixture was extracted with ethyl acetate. The organic phase was washed with brine, dried over MgSO$_4$ and concentrated in vacuo to give the title compound which was used in the next step without further purification.

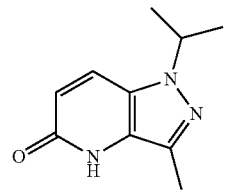

1-isopropyl-3-methyl-1,4-dihydro-5H-pyrazolo[4,3-b]pyridin-5-one was prepared in a similar way from ethyl 3-(4-amino-1-isopropyl-3-methyl-1H-pyrazol-5-yl)acrylate

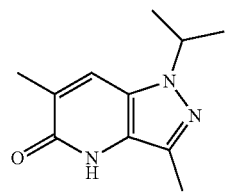

1-isopropyl-3,6-dimethyl-1,4-dihydro-5H-pyrazolo[4,3-b]pyridin-5-one was prepared in a similar way from ethyl 3-(4-amino-1-isopropyl-3-methyl-1H-pyrazol-5-yl)-2-methylacrylate Preparation of 5-chloro-1-ethyl-3,6-dimethyl-1H-pyrazolo[4,3-b]pyridine

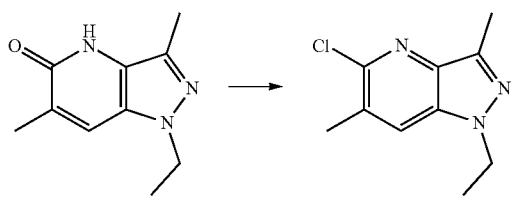

1-ethyl-3,6-dimethyl-1H-pyrazolo[4,3-b]pyridin-5(4H)-one (41 mg, 0.214 mmol) in phosphorus oxychloride (300 µL) was stirred at 80° C. overnight. The reaction mixture was poured into water. The mixture was neutralized with saturated aqueous NaHCO$_3$. The mixture was extracted with ethyl acetate. The organic phase was washed with brine, dried over MgSO$_4$ and concentrated in vacuo to give the title compound which was used in the next step without further purification.

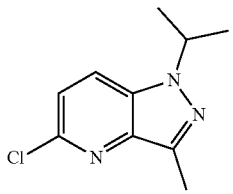

5-chloro-1-isopropyl-3-methyl-1H-pyrazolo[4,3-b]pyridine was prepared in a similar way from 1-isopropyl-3-methyl-1,4-dihydro-5H-pyrazolo[4,3-b]pyridin-5-one

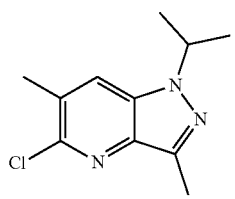

5-chloro-1-isopropyl-3,6-dimethyl-1H-pyrazolo[4,3-b]pyridine was prepared in a similar way from 1-isopropyl-3,6-dimethyl-1,4-dihydro-5H-pyrazolo[4,3-b]pyridin-5-one Preparation of ethyl 4-amino-1-isopropyl-3-methyl-1H-pyrazole-5-carboxylate

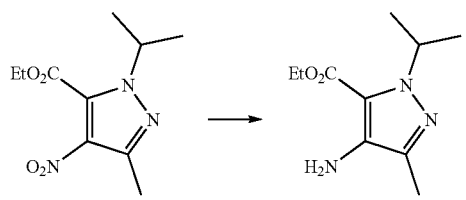 [SMILES: CCOC(=O)c1c([N+](=O)[O-])c(C)nn1C(C)C ; CCOC(=O)c1c(N)c(C)nn1C(C)C]

To a solution of ethyl 1-isopropyl-3-methyl-4-nitro-1H-pyrazole-5-carboxylate (10.23 g, 42.41 mmol) in ethyl acetate (200 mL) was added Pd—C (10%, 2.0 g, wet) under nitrogen. The suspension was degassed under vacuo and purged with hydrogen several times. The mixture was stirred under hydrogen (30 psi) at 40° C. for 18 hours. The mixture was filtered and the residue was washed with ethyl acetate (150 ml×3), the combined filtrates were concentrated to give ethyl 4-amino-1-isopropyl-3-methyl-1H-pyrazole-5-carboxylate.

Preparation of ethyl 1-isopropyl-4-(3-methoxy-3-oxopropanamido)-3-methyl-1H-pyrazole-5-carboxylate

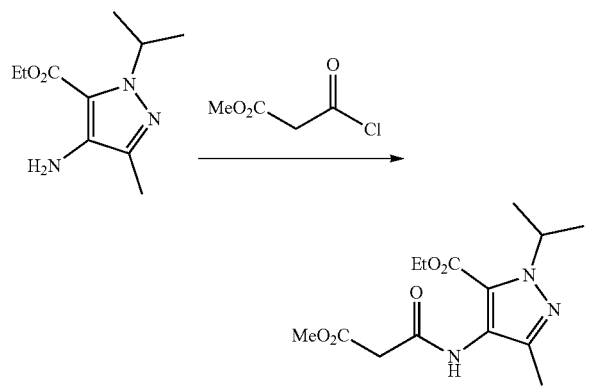

To a solution of ethyl 4-amino-1-isopropyl-3-methyl-1H-pyrazole-5-carboxylate (7.96 g, 37.7 mmol) in dichloromethane (150 mL) was added methyl 3-chloro-3-oxopropanoate (5.14 g, 37.7 mmol, 4.02 mL). The mixture was stirred at 50° C. for 45 minutes. After the reaction mixture had cooled to room temperature, the mixture was partitioned between dichloromethane (200 mL) and saturated aqueous NaHCO₃ (100 mL), the aqueous phase was extracted with dichloromethane (100 mL×2), the combined organic layers were washed with brine (50 mL), dried over MgSO₄ and concentrated to give ethyl 1-isopropyl-4-(3-methoxy-3-oxopropanamido)-3-methyl-1H-pyrazole-5-carboxylate.

Preparation of methyl 5,7-dihydroxy-1-isopropyl-3-methyl-1H-pyrazolo[4,3-b]pyridine-6-carboxylate

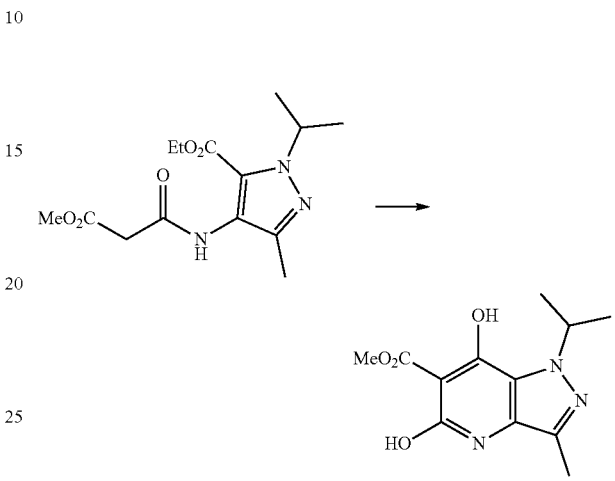

To a solution of ethyl 1-isopropyl-4-(3-methoxy-3-oxopropanamido)-3-methyl-1H-pyrazole-5-carboxylate (12.5 g, 40 mmol) in ethanol (200 mL) was added NaOEt (5.45 g, 80 mmol). The mixture was stirred at 20° C. for 1 hour. The mixture was concentrated. The crude product was used into the next step without further purification.

Preparation of 1-isopropyl-3-methyl-1H-pyrazolo[4,3-b]pyridine-5,7-diol

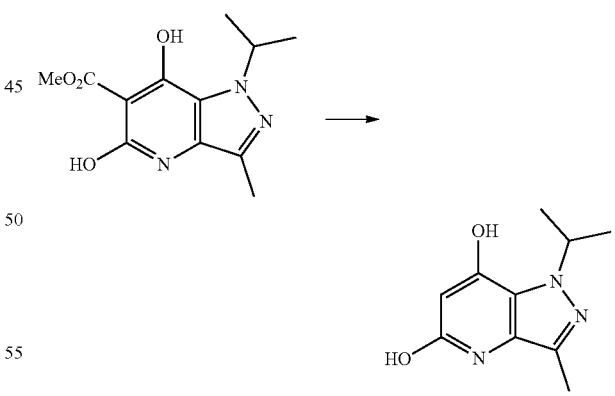

A mixture of methyl 5,7-dihydroxy-1-isopropyl-3-methyl-1H-pyrazolo[4,3-b]pyridine-6-carboxylate (10.62 g, 40.04 mmol) in aqueous NaOH (2 N, 150 mL) was stirred at 110° C. for 6 hours. The mixture was cooled to 0° C., then saturated aqueous KHSO₄ was added to adjust the pH to 2~3. The resulting mixture was filtered and the residue was washed with water (50 mL×3), then dried to give 1-isopropyl-3-methyl-1H-pyrazolo[4,3-b]pyridine-5,7-diol.

Preparation of 5,7-dichloro-1-isopropyl-3-methyl-1H-pyrazolo[4,3-b]pyridine

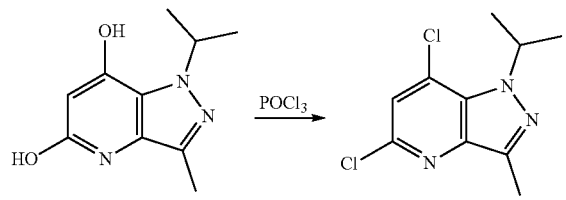

A mixture of 1-isopropyl-3-methyl-1H-pyrazolo[4,3-b]pyridine-5,7-diol (3.50 g, 16.9 mmol) in phosphoryl trichloride (30 mL) was stirred at 80° C. for 18 hours. The mixture was stirred at 85° C. for another 1 hour. The mixture was concentrated and then water (50 mL) was added slowly, followed by saturated aqueous NaHCO$_3$ to adjust pH to 7. The aqueous phase was extracted with ethyl acetate (70 mL×3), the combined organic layers were washed with brine (50 mL), dried over Na$_2$SO$_4$ and concentrated. The crude product was purified by flash chromatography with petroleum ether:ethyl acetate=20:1 to give 5,7-dichloro-1-isopropyl-3-methyl-1H-pyrazolo[4,3-b]pyridine.

Preparation of 5-chloro-1-isopropyl-N-(4-methoxybenzyl)-3-methyl-1H-pyrazolo[4,3-b]pyridin-7-amine

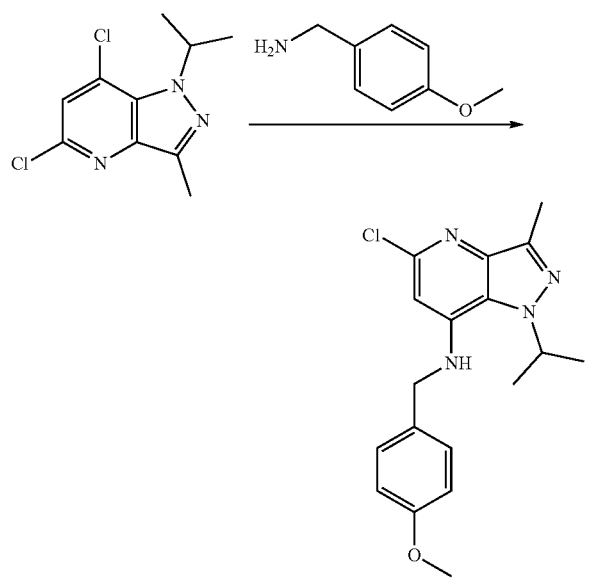

To a solution of 5,7-dichloro-1-isopropyl-3-methyl-1H-pyrazolo[4,3-b]pyridine (100 mg, 410 μmop and (4-methoxyphenyl)methanamine (67 mg, 492 μmol, 64 μL) in NMP (5 mL) was added CsF (124 mg, 819 μmol, 30 μL). The mixture was stirred at 100° C. for 18 hours. Water (20 mL) was added and the mixture was filtered and concentrated in vacuo. The crude mixture was purified by flash chromatography with petroleum ether:ethyl acetate=3:1 to give the title compound.

Preparation of 5-(2-ethoxypyridin-3-yl)-1-isopropyl-N-(4-methoxybenzyl)-3-methyl-1H-pyrazolo[4,3-b]pyridin-7-amine

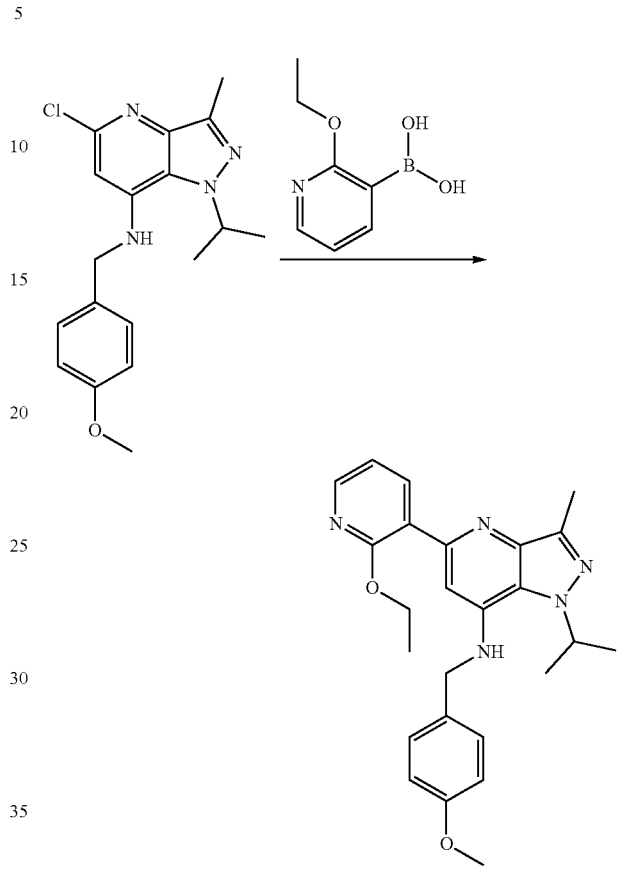

To a solution of 5-chloro-1-isopropyl-N-(4-methoxybenzyl)-3-methyl-1H-pyrazolo[4,3-b]pyridin-7-amine (60 mg, 174 μmol) in dioxane (2 mL) and H$_2$O (0.5 mL) was added Pd(1,1'-bis(diphenylphosphino)ferrocene)Cl$_2$ (25 mg, 35 μma) and Cs$_2$CO$_3$ (141.72 mg, 435 μmol) and (2-ethoxypyridin-3-yl)boronic acid (52 mg, 313 μmol). The mixture was stirred at 100° C. for 1 hour under microwave irradiation. Water (30 mL) was added and the mixture was extracted with ethyl acetate (30 mL×3). The combined organic layers were washed with brine (20 mL), dried over Na$_2$SO$_4$ and concentrated. The crude mixture was purified by flash chromatography with petroleum ether:ethyl acetate=1:1 to 0:1 to give the title compound.

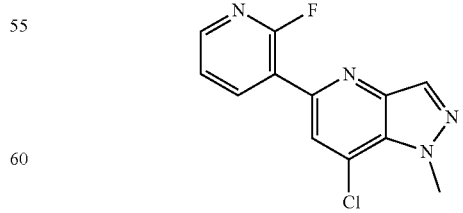

7-chloro-5-(2-fluoropyridin-3-yl)-1-methyl-1H-pyrazolo[4,3-b]pyridine was prepared in a similar way from (2-fluoropyridin-3-yl)boronic acid and 5,7-dichloro-1-methyl-1H-pyrazolo[4,3-b]pyridine.

Preparation of 2-chloro-4-(2-ethoxypyridin-3-yl)-5-methylpyrimidine

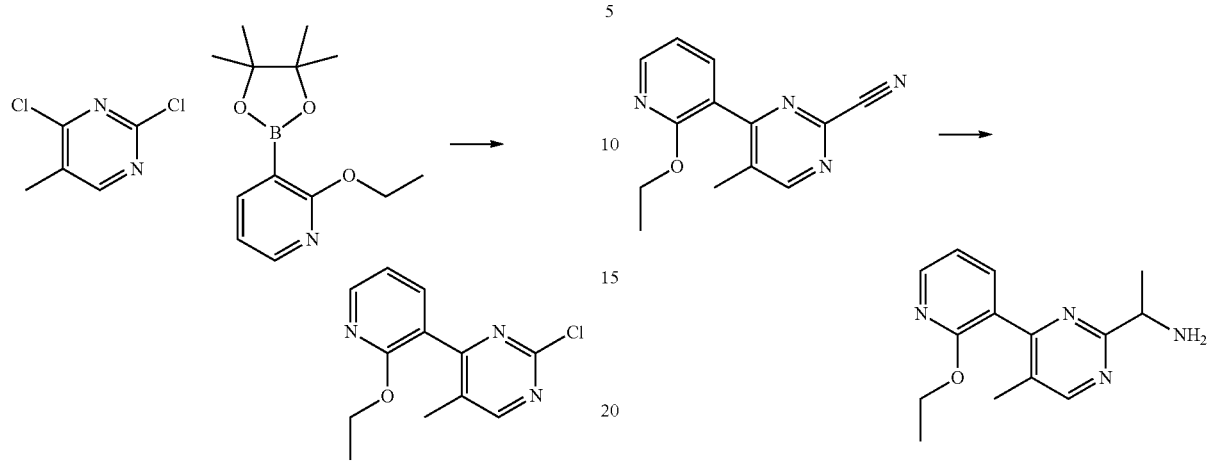

2,4-Dichloro-5-methylpyrimidine (2.87 g, 17.6 mmol), 2-ethoxy-3-(4,4,5,5-tetramethyl-1,3,2-dioxaborolan-2-yl)pyridine (3.50 g, 14.1 mmol), 1,1'-bis(diphenylphosphino)ferrocenepalladium (II) dichloride (1.29 g, 1.76 mmol), potassium carbonate (5.59 g, 40.4 mmol), 1,4-dioxane (58 mL) and water (19 mL) were mixed in a vial. The vial was flushed with nitrogen for 2 min then sealed and stirred overnight at 100° C. Water was added. The mixture was extracted with ethyl acetate. The organic phase was washed with brine, dried over MgSO$_4$ and concentrated in vacuo. The crude material was purified via flash chromatography on silica gel (etyl acetate/heptane) to afford the title compound.

Preparation of 4-(2-ethoxypyridin-3-yl)-5-methylpyrimidine-2-carbonitrile

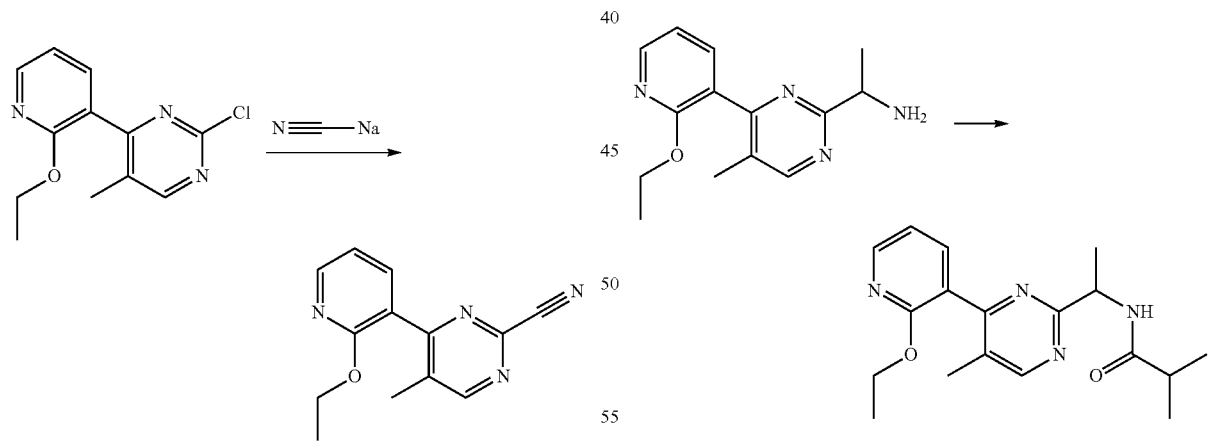

2-Chloro-4-(2-ethoxypyridin-3-yl)-5-methylpyrimidine (2.31 g, 9.25 mmol), NaCN (1.05 g, 21.4 mmol) and DABCO (1,4-diazabicyclo[2.2.2]octane) (0.440 g, 3.92 mmol) were dissolved in DMSO (23 mL)/water (5 mL) and the solution was stirred at 80° C. for 2.5 hours. Water was added. The mixture was extracted with ethyl acetate. The organic phase was washed with saturated aqueous NaHCO$_3$ and brine, dried over MgSO$_4$ and concentrated in vacuo. The crude material was purified via flash chromatography on silica gel (etyl acetate/heptane) to afford the title compound.

Preparation of 1-(4-(2-ethoxypyridin-3-yl)-5-methylpyrimidin-2-yl)ethanamine

To a solution of 4-(2-ethoxypyridin-3-yl)-5-methylpyrimidine-2-carbonitrile (1.83 g, 7.62 mmol) in THF (80 mL) was added methylmagnesium bromide (5.35 ml, 18.2 mmol, 3.4 M in THF) dropwise at room temperature. The reaction mixture was stirred for 5 minutes at room temperature, then heated to reflux for 1 hour. Ethanol (124 mL) and NaBH$_4$ (0.775 g, 20.5 mmol) were added. The reaction mixture was stirred at room temperature for 1 hour. The reaction mixture was concentrated in vacuo to give the crude title compound which was used in the next step without further purification.

Preparation of N-(1-(4-(2-ethoxypyridin-3-yl)-5-methylpyrimidin-2-yl)ethyl)isobutyramide 1-(4-(2-Ethoxypyridin-3-yl)-5-methylpyrimidin-2-yl)ethanamine (1.968 g, 7.62 mmol) was dissolved in THF (82 mL), N,N-diisopropylethylamine (3.98 ml, 22.8 mmol) was added followed by isobutyric anhydride (3.79 ml, 22.9 mmol). The reaction mixture was stirred at room temperature overnight. The reaction mixture was concentrated in vacuo. The residue was stirred with ethylacetate for 10 minutes, then filtered and evaporated. The crude material was purified via flash chromatography on silica gel (etyl acetate/heptane) to afford the title compound.

Preparation of 7-bromo-5-chloro-1-methyl-1H-pyrazolo[4,3-b]pyridine

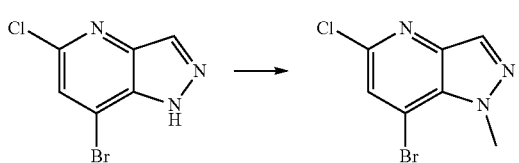

To a mixture of 7-bromo-5-chloro-1H-pyrazolo[4,3-b]pyridine (prepared as described in Jpn. Kokai Tokkyo Koho, 2011246389) (5.30 g, 22.8 mmol) and Cs₂CO₃ (14.86 g, 45.60 mmol) in DMF (50 mL) was added MeI (7.20 g, 50.73 mmol) dropwise with stirring at 0° C. The mixture was stirred at 0° C. for 0.5 hours. Water was added. The mixture was extracted with ethyl acetate. The organic phase was washed with brine, dried over Na₂SO₄ and concentrated in vacuo. The crude material was purified via flash chromatography on silica gel (etyl acetate/petroleum ether) to afford the title compound.

Preparation of (±)-7-bromo-5-chloro-1-(tetrahydrofuran-3-yl)-1H-pyrazolo[4,3-b]pyridine

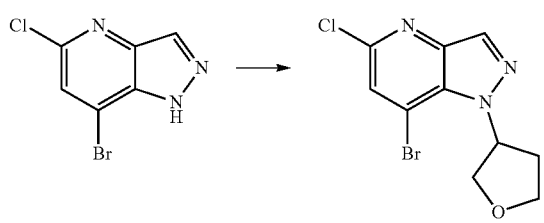 [SMILES: Clc1cc(Br)c2[nH]ncc2n1 ; Clc1cc(Br)c2c(cnn2C2CCOC2)n1]

Diisopropyl azodicarboxylate (254 µl, 1.29 mmol) was dropwise added to an ice cold solution of 7-bromo-5-chloro-1H-pyrazolo[4,3-b]pyridine (200 mg, 0.860 mmol), tetrahydrofuran-3-ol (racemic) (91 mg, 83 µl, 1.032 mmol) and triphenylphosphine (338 mg, 1.291 mmol) in THF (4 mL). After stirring at ice bath temperature over approx. 15 minutes, the reaction mixture was allowed to reach room temperature and was stirred overnight. The reaction mixture was concentrated in vacuo. Ethyl acetate was added and the mixture was washed with aqueous NaOH (1N) and brine, dried over Na₂SO₄ and concentrated in vacuo. The crude material was purified via flash chromatography on silica gel (etyl acetate/heptane) to afford the title compound.

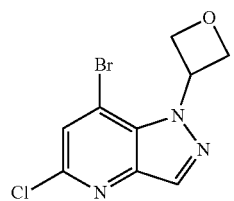 [SMILES: Clc1cc(Br)c2c(cnn2C2COC2)n1]

7-Bromo-5-chloro-1-(oxetan-3-yl)-1H-pyrazolo[4,3-b]pyridine was prepared in a similar way from 7-bromo-5-chloro-1H-pyrazolo[4,3-b]pyridine and oxetan-3-ol.

Preparation of 4,6-dibromo-2-methylpyridin-3-amine

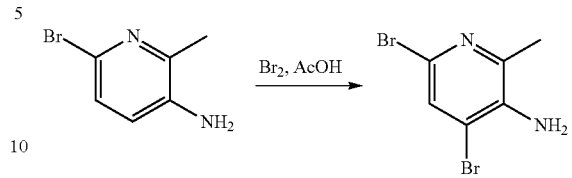

A solution of 6-bromo-2-methylpyridin-3-amine (24 g, 128 mmol) and AcOH (14.7 mL 257 mmol) in MeOH (200 mL) was cooled to 0° C., Br₂ (36.9 g, 230.9 mmol, 11.9 mL) was added and stirred at 0° C. for 5 hours. The mixture was quenched with saturated aqueous Na₂SO₃ (500 mL), extracted with ethyl acetate (300 mL×3). The organic layer was washed with brine (200 mL), dried over Na₂SO₄, and concentrated in vacuo. The residue was purified by silica gel chromatography (petroleum ether:ethyl acetate=2:1) to afford 4,6-dibromo-2-methylpyridin-3-amine.

Preparation of 5,7-dibromo-1H-pyrazolo[4,3-b]pyridine

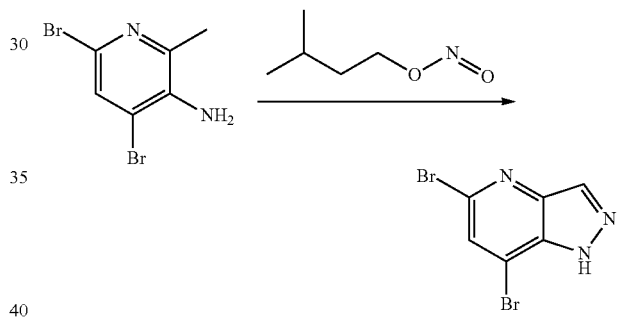

To a mixture of 4,6-dibromo-2-methylpyridin-3-amine (15.0 g, 56.4 mmol) and AcOK (13.8 g, 141 mmol) in AcOH (30 mL) and toluene (200 mL) was added isopentyl nitrite (13.2 g, 112.8 mmol). The mixture was stirred at 25° C. for 1 hour then at 60° C. for 19 hours. The mixture was concentrated in vacuo, diluted with water (300 mL) and extracted with ethyl acetate (200 mL×2). The organic layer was washed with brine (100 mL), dried over Na₂SO₄ and concentrated in vacuo to give 5,7-dibromo-1H-pyrazolo[4,3-b]pyridine.

Preparation of 5,7-dibromo-1-ethyl-1H-pyrazolo[4,3-b]pyridine

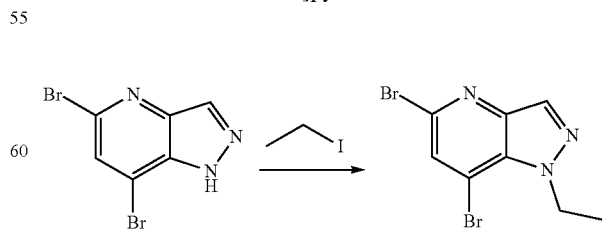

To a mixture of 5,7-dibromo-1H-pyrazolo[4,3-b]pyridine (1 g, 3.6 mmol) and Cs₂CO₃ (2.4 g, 7.2 mmol) in anhydrous DMF (10 mL) was added iodoethane (0.8 g, 5.4 mmol). The mixture was stirred at 0° C. for 0.5 hours. The mixture was diluted with water (20 mL), extracted with ethyl acetate (30 mL×2). The organic layer was washed with water (20 mL), brine (20 mL) and dried with Na$_2$SO$_4$, concentrated in vacuo. The residue was purified by silica gel chromatography (petroleum ether:ethyl acetate=10:1-5:1) to give 5,7-dibromo-1-ethyl-1H-pyrazolo[4,3-b]pyridine.

The following compounds were prepared in a similar manner:

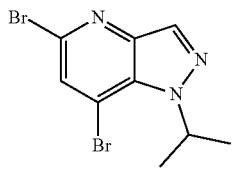

5,7-Dibromo-1-isopropyl-1H-pyrazolo[4,3-b]pyridine from 5,7-dibromo-1H-pyrazolo[4,3-b]pyridine and 2-iodopropane.

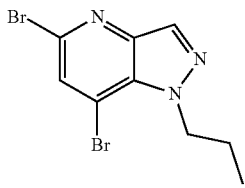

5,7-Dibromo-1-propyl-1H-pyrazolo[4,3-b]pyridine from 5,7-dibromo-1H-pyrazolo[4,3-b]pyridine and 1-iodopropane.

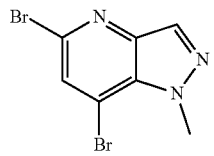

5,7-Dibromo-1-methyl-1H-pyrazolo[4,3-b]pyridine from 5,7-dibromo-1H-pyrazolo[4,3-b]pyridine and iodomethane.

Preparation of 5-chloro-N,1-bis(tetrahydrofuran-3-yl)-1H-pyrazolo[4,3-b]pyridin-7-amine

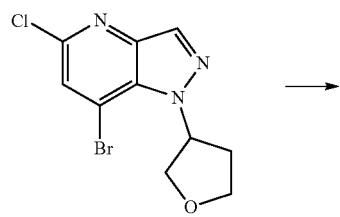 →

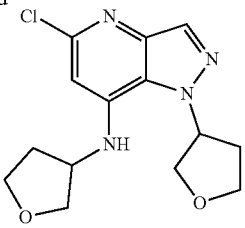

A mixture of (±)-7-bromo-5-chloro-1-(tetrahydrofuran-3-yl)-1H-pyrazolo[4,3-b]pyridine (50 mg, 0.17 mmol), (±)-tetrahydrofuran-3-amine (145 mg, 1.7 mmol) and N,N-diisopropylethylamine (0.14 ml, 0.83 mmol) in NMP (650 µL) was heated to 120° C. for 2.25 hours under microwave irradiation. Water was added. The mixture was extracted with ethyl acetate. The organic phase was washed with brine, dried over Na$_2$SO$_4$ and concentrated in vacuo. The crude material was purified via flash chromatography on silica gel (ethyl acetate/heptane) to afford the title compound.

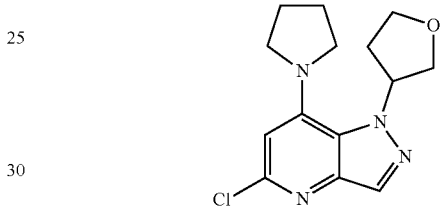

(±)-5-chloro-7-(pyrrolidin-1-yl)-1-(tetrahydrofuran-3-yl)-1H-pyrazolo[4,3-b]pyridine was prepared in a similar way from (±)-7-bromo-5-chloro-1-(tetrahydrofuran-3-yl)-1H-pyrazolo[4,3-b]pyridine and pyrrolidine.

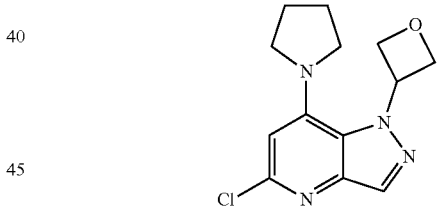

5-Chloro-1-(oxetan-3-yl)-7-(pyrrolidin-1-yl)-1H-pyrazolo[4,3-b]pyridine was prepared in a similar way from 7-bromo-5-chloro-1-(oxetan-3-yl)-1H-pyrazolo[4,3-b]pyridine and pyrrolidine.

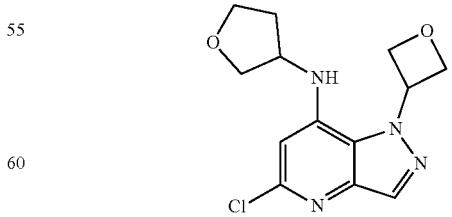

(±)-5-Chloro-1-(oxetan-3-yl)-N-(tetrahydrofuran-3-yl)-1H-pyrazolo[4,3-b]pyridin-7-amine was prepared in a similar way from 7-bromo-5-chloro-1-(oxetan-3-yl)-1H-pyrazolo[4,3-b]pyridine and (±)-tetrahydrofuran-3-amine.

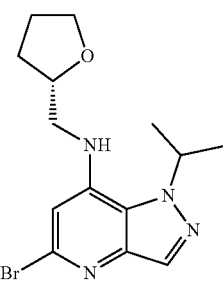 [SMILES: CC(C)n1ncc2nc(Br)cc(NC[C@@H]3CCCO3)c21]

(S)-5-bromo-1-isopropyl-N-((tetrahydrofuran-2-yl)methyl)-1H-pyrazolo[4,3-b]pyridin-7-amine was prepared in a similar way from 5,7-dibromo-1-isopropyl-1H-pyrazolo[4,3-b]pyridine and (S)-(tetrahydrofuran-2-yl)methanamine.

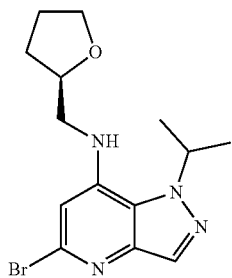 [SMILES: CC(C)n1ncc2nc(Br)cc(NC[C@H]3CCCO3)c21]

(R)-5-bromo-1-isopropyl-N-((tetrahydrofuran-2-yl)methyl)-1H-pyrazolo[4,3-b]pyridin-7-amine was prepared in a similar way from 5,7-dibromo-1-isopropyl-1H-pyrazolo[4,3-b]pyridine and (R)-(tetrahydrofuran-2-yl)methanamine.

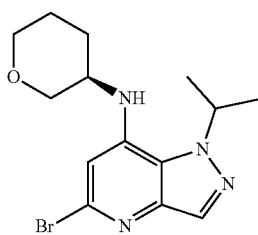 [SMILES: CC(C)n1ncc2nc(Br)cc(N[C@@H]3CCCOC3)c21]

(R)-5-bromo-1-isopropyl-N-(tetrahydro-2H-pyran-3-yl)-1H-pyrazolo[4,3-b]pyridin-7-amine was prepared in a similar way from 5,7-dibromo-1-isopropyl-1H-pyrazolo[4,3-b]pyridine and (R)-tetrahydro-2H-pyran-3-amine hydrochloride

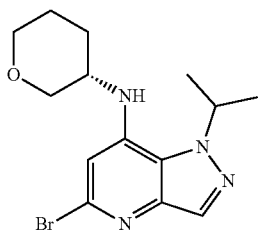 [SMILES: CC(C)n1ncc2nc(Br)cc(N[C@H]3CCCOC3)c21]

(S)-5-bromo-1-isopropyl-N-(tetrahydro-2H-pyran-3-yl)-1H-pyrazolo[4,3-b]pyridin-7-amine was prepared in a similar way from 5,7-dibromo-1-isopropyl-1H-pyrazolo[4,3-b]pyridine and (S)-tetrahydro-2H-pyran-3-amine hydrochloride.

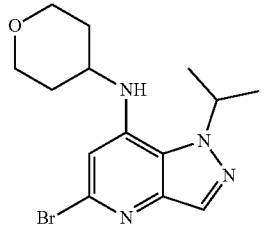 [SMILES: CC(C)n1ncc2nc(Br)cc(NC3CCOCC3)c21]

5-bromo-1-isopropyl-N-(tetrahydro-2H-pyran-4-yl)-1H-pyrazolo[4,3-b]pyridin-7-amine was prepared in a similar way from 5,7-dibromo-1-isopropyl-1H-pyrazolo[4,3-b]pyridine and tetrahydro-2H-pyran-4-amine.

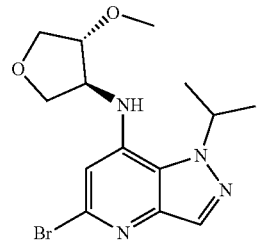 [SMILES: CO[C@H]1COC[C@@H]1Nc1cc(Br)nc2cnn(C(C)C)c12]

Trans-(±)-5-bromo-1-isopropyl-N-(trans-4-methoxytetrahydrofuran-3-yl)-1H-pyrazolo[4,3-b]pyridin-7-amine was prepared in a similar way from 5,7-dibromo-1-isopropyl-1H-pyrazolo[4,3-b]pyridine and trans-(±)-4-methoxytetrahydrofuran-3-amine.

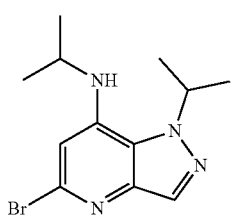 [SMILES: CC(C)Nc1cc(Br)nc2cnn(C(C)C)c12]

5-bromo-N,1-diisopropyl-1H-pyrazolo[4,3-b]pyridin-7-amine was prepared in a similar way from 5,7-dibromo-1-isopropyl-1H-pyrazolo[4,3-b]pyridine and propan-2-amine.

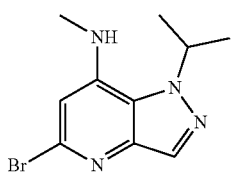

5-bromo-1-isopropyl-N-methyl-1H-pyrazolo[4,3-b]pyridin-7-amine was prepared in a similar way from 5,7-dibromo-1-isopropyl-1H-pyrazolo[4,3-b]pyridine and methylamine.

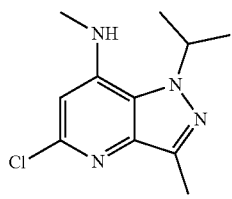 [SMILES: CNc1cc(Cl)nc2c(C)nn(C(C)C)c12]

5-chloro-1-isopropyl-N,3-dimethyl-1H-pyrazolo[4,3-b]pyridin-7-amine was prepared in a similar way from 5,7-dichloro-1-isopropyl-3-methyl-1H-pyrazolo[4,3-b]pyridine and methylamine.

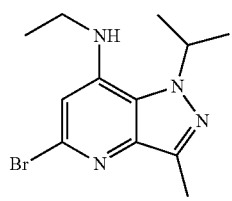 [SMILES: CCNc1cc(Br)nc2c(C)nn(C(C)C)c12]

5-bromo-N-ethyl-1-isopropyl-3-methyl-1H-pyrazolo[4,3-b]pyridin-7-amine was prepared in a similar way from 5,7-dibromo-1-isopropyl-3-methyl-1H-pyrazolo[4,3-b]pyridine and methylamine.

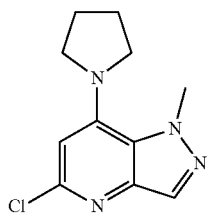

5-chloro-1-methyl-7-(pyrrolidin-1-yl)-1H-pyrazolo[4,3-b]pyridine was prepared in a similar way from 7-bromo-5-chloro-1-methyl-1H-pyrazolo[4,3-b]pyridine and pyrrolidine.

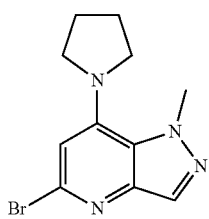 [SMILES: Cn1ncc2nc(Cl)cc(N3CCCC3)c21]

5-bromo-1-methyl-7-(pyrrolidin-1-yl)-1H-pyrazolo[4,3-b]pyridine was prepared in a similar way from 5,7-dibromo-1-methyl-1H-pyrazolo[4,3-b]pyridine and pyrrolidine.

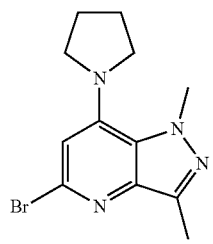 [SMILES: Cc1nn(C)c2c(N3CCCC3)cc(Br)nc12]

5-bromo-1,3-dimethyl-7-(pyrrolidin-1-yl)-1H-pyrazolo[4,3-b]pyridine was prepared in a similar way from 5,7-dibromo-1,3-dimethyl-1H-pyrazolo[4,3-b]pyridine and pyrrolidine.

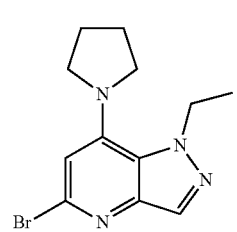 [SMILES: CCn1ncc2nc(Br)cc(N3CCCC3)c21]

5-bromo-1-ethyl-7-(pyrrolidin-1-yl)-1H-pyrazolo[4,3-b]pyridine was prepared in a similar way from 5,7-dibromo-1-ethyl-1H-pyrazolo[4,3-b]pyridine and pyrrolidine.

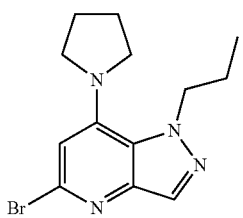 [SMILES: CCCn1ncc2nc(Br)cc(N3CCCC3)c21]

5-bromo-1-propyl-7-(pyrrolidin-1-yl)-1H-pyrazolo[4,3-b]pyridine was prepared in a similar way from 5,7-dibromo-1-propyl-1H-pyrazolo[4,3-b]pyridine and pyrrolidine.

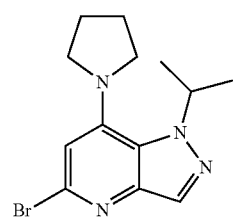

5-bromo-1-isopropyl-7-(pyrrolidin-1-yl)-1H-pyrazolo[4,3-b]pyridine was prepared in a similar way from 5,7-dibromo-1-isopropyl-1H-pyrazolo[4,3-b]pyridine and pyrrolidine.

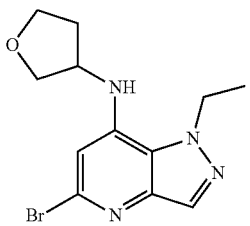 [SMILES: CCn1ncc2nc(Br)cc(NC3CCOC3)c21]

(±)-5-bromo-1-ethyl-N-(tetrahydrofuran-3-yl)-1H-pyrazolo[4,3-b]pyridin-7-amine was prepared in a similar way from 5,7-dibromo-1-ethyl-1H-pyrazolo[4,3-b]pyridine and (±)-tetrahydro-2H-pyran-3-amine hydrochloride.

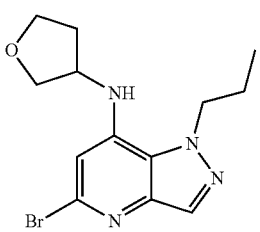 [SMILES: CCCn1ncc2nc(Br)cc(NC3CCOC3)c21]

(±)-5-bromo-1-propyl-N-(tetrahydrofuran-3-yl)-1H-pyrazolo[4,3-b]pyridin-7-amine was prepared in a similar way from 5,7-dibromo-1-propyl-1H-pyrazolo[4,3-b]pyridine and (±)-tetrahydro-2H-pyran-3-amine hydrochloride.

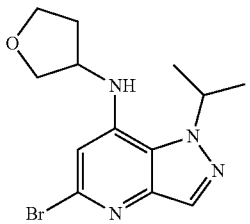 [SMILES: CC(C)n1ncc2nc(Br)cc(NC3CCOC3)c21]

(±)-5-bromo-1-isopropyl-N-(tetrahydrofuran-3-yl)-1H-pyrazolo[4,3-b]pyridin-7-amine was prepared in a similar way from 5,7-dibromo-1-isopropyl-1H-pyrazolo[4,3-b]pyridine and (±)-tetrahydro-2H-pyran-3-amine hydrochloride.

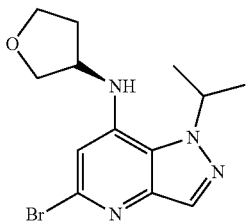

(R)-5-bromo-1-isopropyl-N-(tetrahydrofuran-3-yl)-1H-pyrazolo[4,3-b]pyridin-7-amine was prepared in a similar way from 5,7-dibromo-1-isopropyl-1H-pyrazolo[4,3-b]pyridine and (R)-tetrahydro-2H-pyran-3-amine hydrochloride.

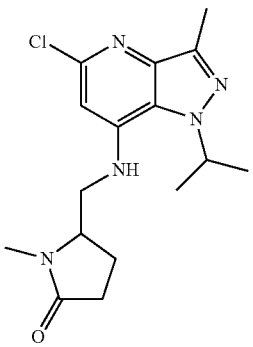 [SMILES: Cc1nn(C(C)C)c2c(NCC3CCC(=O)N3C)cc(Cl)nc12]

(±)-5-(((5-chloro-1-isopropyl-3-methyl-1H-pyrazolo[4,3-b]pyridin-7-yl)amino)methyl)-1-methylpyrrolidin-2-one was prepared in a similar way from from 5,7-dichloro-1-isopropyl-3-methyl-1H-pyrazolo[4,3-b]pyridine and 5-(aminomethyl)-1-methylpyrrolidin-2-one.

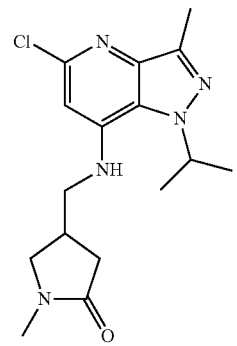 [SMILES: Cc1nn(C(C)C)c2c(NCC3CC(=O)N(C)C3)cc(Cl)nc12]

(±)-4-(((5-chloro-1-isopropyl-3-methyl-1H-pyrazolo[4,3-b]pyridin-7-yl)amino)methyl)-1-methylpyrrolidin-2-one was prepared in a similar way from 5,7-dichloro-1-isopropyl-3-methyl-1H-pyrazolo[4,3-b]pyridine and 4-(aminomethyl)-1-methylpyrrolidin-2-one.

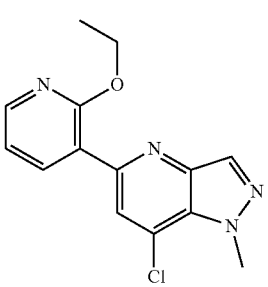 [SMILES: CCOc1ncccc1-c1cc(Cl)c2c(cnn2C)n1]

7-chloro-5-(2-ethoxypyridin-3-yl)-1-methyl-1H-pyrazolo[4,3-b]pyridine was prepared in a similar way from 7-chloro-5-(2-fluoropyridin-3-yl)-1-methyl-1H-pyrazolo[4,3-b]pyridine and ethanol.

Preparation of 3-bromo-4-methylpyridin-2-ol

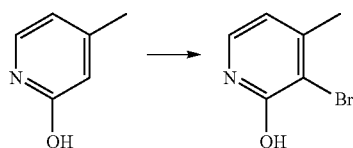

4-Methylpyridin-2-ol (5.00 g, 45.8 mmol) in AcOH (75 mL) and ethyl acetate (150 mL) was treated with NBS (7.50 g, 42.2) and stirred at 15° C. for 1 hour. The mixture was then taken to pH 8 with aqueous ammonia (40 mL) and extracted with ethyl acetate. The separated organics were washed with 1:1 H₂O/brine (30 mL/30 mL), the dried with anhydrous Na₂SO₄, filtered and concentrated. The residue was purified by preperative-HPLC to afford the title compound.

Preparation of 3-bromo-2-ethoxy-4-methylpyridine

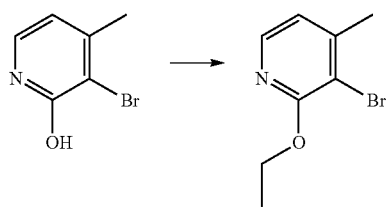

3-bromo-4-methylpyridin-2-ol in anhydrous dichloromethane (60 mL) was treated with ethyl iodide (89.4 mmol, 7.15 mL) and Ag₂CO₃ (4.93 g, 17.9 mmol). The mixture was stirred at 30° C. for 80 hours. The mixture was filtered and concentrated under reduced pressure to give a residue. The residue was purified by column chromatography on silica gel to afford the title compound.

Preparation of 2-ethoxy-4-methyl-3-(4,4,5,5-tetramethyl-1,3,2-dioxaborolan-2-yl)pyridine

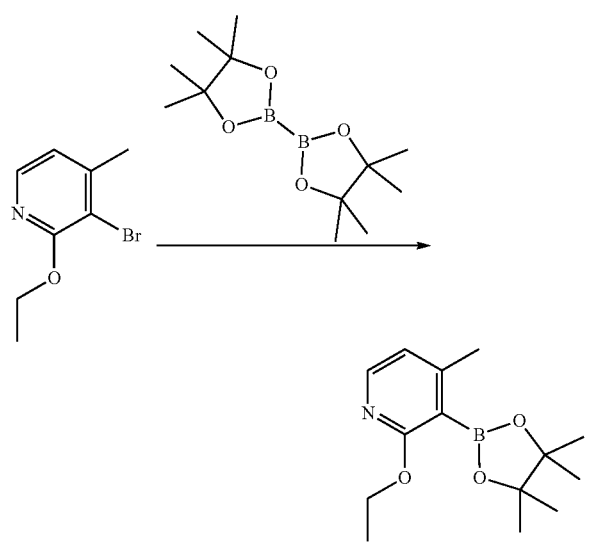

A mixture of 3-bromo-2-ethoxy-4-methylpyridine (500 mg, 2.31 mmol), 4,4,4',4',5,5,5',5'-octamethyl-2,2'-bi(1,3,2-dioxaborolane) (880 mg, 3.47 mmol), KOAc (680 mg, 6.93 mmol), Pd(dppf)Cl₂ (169 mg, 0.231 mmol) in dioxane (10 mL) was degassed and purged with N₂ 3 times, and then the mixture was stirred at 100° C. for 12 hour under a N₂ atmosphere. The reaction mixture was concentrated under reduced pressure. The residue was purified by flash silica gel chromatography (ethyl acetate/petroleum ether) to afford the title compound.

Preparation of
(2-methoxy-5-methylpyridin-4-yl)boronic acid

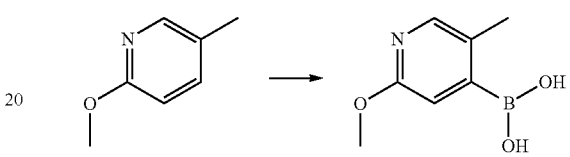

n-BuLi (2.5 M, 1.95 mL) was added dropwise to a solution of 2-methoxy-5-methylpyridine (500 mg, 4.06 mmol) in THF (9 mL) at −78° C. and the mixture was stirred at −40° C. for 0.5 hours. A solution of triisopropyl borate (1.15 g, 6.09 mmol) in THF (1 mL) was added dropwise, and stirring continued for 0.5 hours at −78° C. Then the reaction mixture was stirred at 20° C. for an additional 12 hours. The reaction mixture was poured into water (10 mL) and stirred for 5 minutes. The aqueous phase was extracted with dichloromethane. The organic phase was washed with brine, dried over anhydrous Na₂SO₄, filtered and concentrated in vacuo. The residue was purified by silica gel chromatography (petroleum ether/ethyl acetate) to afford the title compound.

Preparation of 3-ethoxy-5-(4,4,5,5-tetramethyl-1,3,2-dioxaborolan-2-yl)pyridine

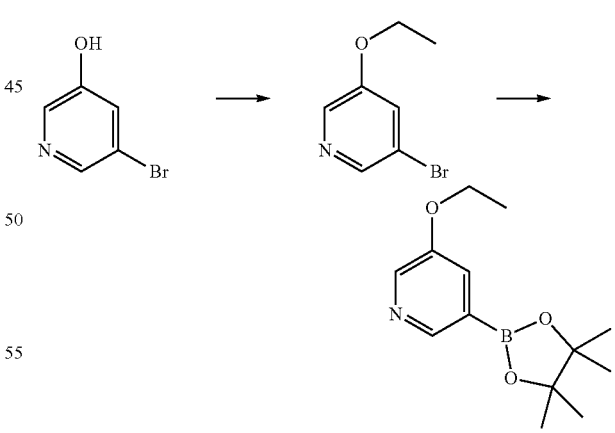

A mixture of 5-bromopyridin-3-ol (500 mg, 2.87 mmol), ethyl bromide (375 mg, 3.44 mmol) and K₂CO₃ (793 mg, 5.74 mmol) in DMF (15 mL) was stirred at 60° C. for 18 hours. To the mixture was added (i-Pr)₂O (20 mL). The mixture was washed with 2N NaOH (aqueous, 5 mL×2), the aqueous phase was re-extracted with (i-Pr)₂O (10 mL×2). The combined organic layers were washed with H₂O (10 mL×3), brine (10 mL), dried over Na₂SO₄, filtered and concentrated to give 3-bromo-5-ethoxypyridine which was used for next step without purification. A mixture of 3-bromo-5-ethoxypyridine (100 mg), Pd(dppf)Cl₂ (11 mg, 0.15 mmol), 4,4,4',4',5,5,5',5'-octamethyl-2,2'-bi(1,3,2-dioxaborolane) (138 mg, 0.54 mmol) and KOAc (146 mg, 1.48 mmol) in dioxane (3 mL) was stirred at 90° C. for 1.5 hours under Ar. The mixture was filtered. To the filtrate was added ethyl acetate (10 mL). The filtrate was washed with brine (5 mL×2), dried over Na₂SO₄, filtered and concentrated to give 3-ethoxy-5-(4,4,5,5-tetramethyl-1,3,2-dioxaborolan-2-yl)pyridine which was used for next step without purification.

Preparation of Compounds of the Invention

Example 1: 5-(2-ethoxy-3-pyridyl)-1,3-dimethyl-7-pyrrolidin-1-yl-pyrazolo[4,3-b]pyridine

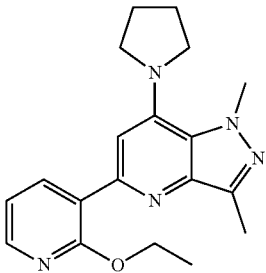 [SMILES: CCOc1ncccc1-c1cc(N2CCCC2)c2c(n1)c(C)nn2C]

A solution of 5-bromo-1,3-dimethyl-7-pyrrolidin-1-yl-pyrazolo[4,3-b]pyridine (40 mg, 0.14 mmol), 2-ethoxy-3-(4,4,5,5-tetramethyl-1,3,2-dioxaborolan-2-yl)pyridine (41 mg, 0.16 mmol), Cs₂CO₃ (88 mg, 0.27) and Pd(dppf)Cl₂ (99 mg, 0.14 mmol) in dioxane (5 mL) and water (1 mL) was stirred at 90° C. for 16 hours. The reaction was concentrated. The residue was diluted with ethyl acetate (5 mL) and water (3 mL), filtered and extracted with ethyl acetate (5 mL×3). The combined organic layers were washed with brine (5 mL×2), dried over Na₂SO₄, filtered and concentrated. The residue was purified by silica gel column chromatography (petroleum:ethyl acetate=10:1~1:1) followed by further purification by preparative HPLC to afford the title compound. ¹H-NMR (400 MHz, Chloroform-d): δ 8.28 (d, J=7.2 Hz, 1H), 8.17 (d, J=5.2 Hz, 1H), 7.45 (s, 1H), 7.03 (dd, J=7.2, 5.2 Hz, 1H), 4.46 (q, J=7.2 Hz, 2H), 4.13 (s, 3H), 3.37-3.35 (m, 4H), 2.64 (s, 3H), 2.05-2.02 (m, 4H), 1.42 (t, J=7.2 Hz, 3H). LC-MS: tR=1.9 min (Method K), m/z=338.1 [M+H]⁺.

Example 2: 5-(2-ethoxy-3-pyridyl)-N,1-di(tetrahydrofuran-3-yl)pyrazolo[4,3-b]pyridin-7-amine

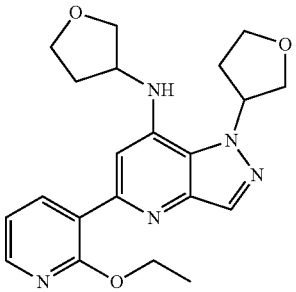 [SMILES: CCOc1ncccc1-c1cc(NC2CCOC2)c2c(cnn2C2CCOC2)n1]

Prepared using the same procedure as described for example 1, from 2-ethoxy-3-(4,4,5,5-tetramethyl-1,3,2-dioxaborolan-2-yl)pyridine and 5-chloro-N,1-bis(tetrahydrofuran-3-yl)-1H-pyrazolo[4,3-b]pyridin-7-amine. Prepared as a 1:1 mixture of diastereomers. 1H-NMR (600 MHz, Chloroform-d): δ 8.23-8.16 (m, 2H), 8.08 (dd, J=4.8, 0.8 Hz, 1H), 7.07 (d, J=3.7 Hz, 1H), 7.03 (ddd, J=7.2, 5.1, 0.8 Hz, 1H), 6.35 (s, 0.5H), 6.23 (s, 0.5H), 5.69-5.57 (m, 1H), 4.49 (qt, J=6.0, 1.0 Hz, 2H), 4.40 (td, J=8.7, 2.8 Hz, 0.5H), 4.38-4.32 (m, 0.5H), 4.32-4.22 (m, 2H), 4.21-4.11 (m, 1H), 4.08-3.99 (m, 2H), 3.98-3.89 (m, 1H), 3.80 (dtd, J=13.4, 9.6, 6.6 Hz, 1H), 2.77-2.64 (m, 1H), 2.51-2.29 (m, 2H), 2.18-2.08 (m, 1H), 1.70 (s, 1H), 1.49-1.39 (m, 3H). LC-MS: tR=0.46 min (Method D), m/z=396.2 [M+H]⁺.

Example 3: (±)-5-(2-ethoxy-3-pyridyl)-7-pyrrolidin-1-yl-1-tetrahydrofuran-3-yl-pyrazolo[4,3-b]pyridine

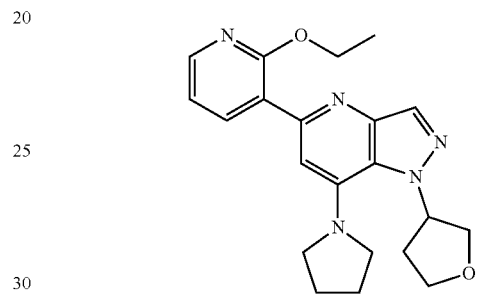

Prepared using the same procedure as described for example 1, from 2-ethoxy-3-(4,4,5,5-tetramethyl-1,3,2-dioxaborolan-2-yl)pyridine and (±)-5-chloro-7-(pyrrolidin-1-yl)-1-(tetrahydrofuran-3-yl)-1H-pyrazolo[4,3-b]pyridine. ¹H-NMR (500 MHz, Chloroform-d): δ 8.33 (s, 1H), 8.27 (d, J=7.3 Hz, 1H), 8.23-8.18 (m, 1H), 7.57 (s, 1H), 7.07-7.03 (m, 1H), 5.76-5.64 (m, 1H), 4.51 (q, J=7.1 Hz, 2H), 4.30 (q, J=7.9 Hz, 1H), 4.19 (dd, J=9.4, 7.3 Hz, 1H), 4.09-3.96 (m, 2H), 3.44-3.25 (m, 4H), 2.50-2.33 (m, 2H), 2.12-2.01 (m, 4H), 1.51-1.41 (m, 3H). LC-MS: tR=0.49 min (Method D), m/z=380.2 [M+H]⁺.

Example 4: 5-(2-ethoxy-3-pyridyl)-1-(oxetan-3-yl)-7-pyrrolidin-1-yl-pyrazolo[4,3-b]pyridine

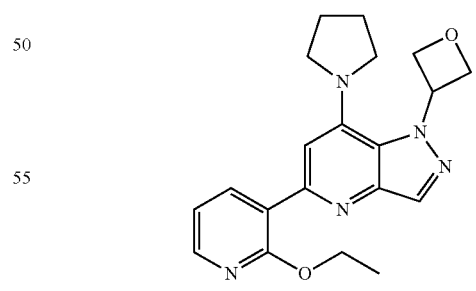

Prepared using the same procedure as described for example 1, from 2-ethoxy-3-(4,4,5,5-tetramethyl-1,3,2-dioxaborolan-2-yl)pyridine and 5-chloro-1-(oxetan-3-yl)-7-(pyrrolidin-1-yl)-1H-pyrazolo[4,3-b]pyridine. ¹H-NMR (500 MHz, Chloroform-d): δ 8.39 (s, 1H), 8.26 (dt, J=7.3, 1.6 Hz, 1H), 8.21 (dd, J=4.9, 1.8 Hz, 1H), 7.54 (s, 1H), 7.11-7.00 (m, 1H), 6.20 (m, 1H), 5.32 (t, J=6.5 Hz, 2H), 5.05

(t, J=7.1 Hz, 2H), 4.49 (q, J=7.0 Hz, 2H), 3.26 (brs, 4H), 2.09 (brs, 4H), 1.48-1.40 (m, 3H). LC-MS: tR=0.45 min (Method E), m/z=366.2 [M+H]$^+$.

Example 5: (±)-5-(2-ethoxy-3-pyridyl)-1-(oxetan-3-yl)-N-tetrahydrofuran-3-yl-pyrazolo[4,3-b]pyridin-7-amine

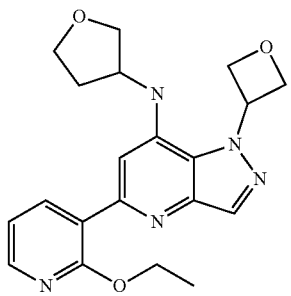 [SMILES: CCOc1ncccc1-c1cc(NC2CCOC2)c2c(cnn2C2COC2)n1]

Prepared using the same procedure as described for example 1, from 2-ethoxy-3-(4,4,5,5-tetramethyl-1,3,2-dioxaborolan-2-yl)pyridine and (±)-5-Chloro-1-(oxetan-3-yl)-N-(tetrahydrofuran-3-yl)-1H-pyrazolo[4,3-b]pyridin-7-amine. $^1$H-NMR (500 MHz, Chloroform-d): δ 8.24 (m, 2H), 8.18 (d, J=1.4 Hz, 1H), 7.20 (d, J=1.4 Hz, 1H), 7.06 (ddd, J=6.8, 5.0, 1.4 Hz, 1H), 6.29 (brs, 1H), 5.99-5.48 (m, 1H), 5.36 (t, J=7.8 Hz, 2H), 5.11 (q, J=6.3 Hz, 2H), 4.57-4.48 (m, 2H), 4.35 (d, J=5.5 Hz, 1H), 4.10-4.02 (m, 2H), 4.02-3.90 (m, 2H), 2.47-2.38 (m, 1H), 2.17-2.08 (m, 1H), 1.46 (t, J=7.1 Hz, 3H). LC-MS: tR=0.41 min (Method E), m/z=382.2 [M+H]$^+$.

Example 6: 5-(2-ethoxy-3-pyridyl)-1-isopropyl-N-[[(2S)-tetrahydrofuran-2-yl]methyl]pyrazolo[4,3-b]pyridin-7-amine

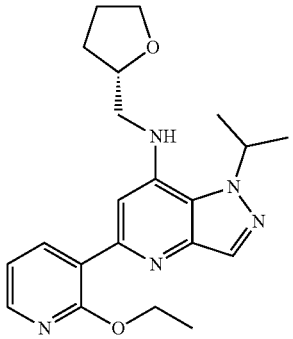 [SMILES: CCOc1ncccc1-c1cc(NC[C@@H]2CCCO2)c2c(cnn2C(C)C)n1]

Prepared using the same procedure as described for example 1, from 2-ethoxy-3-(4,4,5,5-tetramethyl-1,3,2-dioxaborolan-2-yl)pyridine and (S)-5-bromo-1-isopropyl-N-((tetrahydrofuran-2-yl)methyl)-1H-pyrazolo[4,3-b]pyridin-7-amine. $^1$H-NMR (600 MHz, Methanol-d$_4$): δ 8.08 (dd, J=5.0, 2.0 Hz, 1H), 7.91 (s, 1H), 7.89 (dd, J=7.3, 2.0 Hz, 1H), 6.97 (dd, J=7.3, 5.0 Hz, 1H), 6.95 (s, 1H), 5.08-4.99 (m, 1H), 4.35 (q, J=7.1 Hz, 2H), 4.27-4.17 (m, 1H), 3.83 (ddd, J=8.3, 7.1, 6.1 Hz, 1H), 3.71 (ddd, J=8.3, 7.4, 6.3 Hz, 1H), 3.39 (dd, J=13.4, 4.7 Hz, 1H), 3.30 (dd, J=13.4, 7.1 Hz, 1H), 2.07-1.97 (m, 1H), 1.95-1.82 (m, 2H), 1.71-1.64 (m, 1H), 1.49 (dd, J=8.7, 6.5 Hz, 6H), 1.30 (t, J=7.1 Hz, 3H). LC-MS: tR=0.59 min (Method D), m/z=382.1 [M+H]$^+$.

Example 7: 5-(2-ethoxy-3-pyridyl)-1-isopropyl-N-[[(2R)-tetrahydrofuran-2-yl]methyl]pyrazolo[4,3-b]pyridin-7-amine

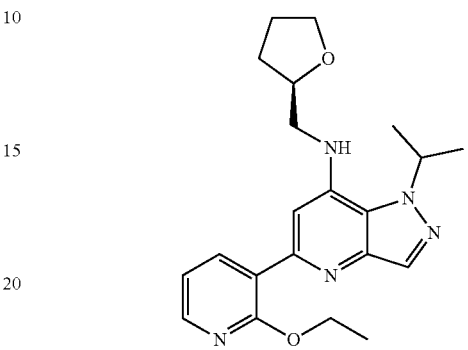

Prepared using the same procedure as described for example 1, from 2-ethoxy-3-(4,4,5,5-tetramethyl-1,3,2-dioxaborolan-2-yl)pyridine and (R)-5-bromo-1-isopropyl-N-((tetrahydrofuran-2-yl)methyl)-1H-pyrazolo[4,3-b]pyridin-7-amine. $^1$H-NMR (600 MHz, DMSO-d$_6$): δ 8.24-8.16 (m, 2H), 8.10 (s, 1H), 7.20 (s, 1H), 7.10 (dd, J=7.3, 4.9 Hz, 1H), 6.31 (t, J=5.7 Hz, 1H), 5.20 (p, J=6.4 Hz, 1H), 4.42 (qd, J=7.0, 2.3 Hz, 2H), 4.23 (p, J=6.3 Hz, 1H), 3.86-3.77 (m, 1H), 3.71-3.63 (m, 1H), 3.36 (m, 2H), 2.03-1.95 (m, 1H), 1.93-1.79 (m, 2H), 1.74-1.68 (m, 1H), 1.48 (dd, J=10.3, 6.4 Hz, 6H), 1.38 (t, J=7.1 Hz, 3H). LC-MS: tR=0.59 min (Method D), m/z=382.1 [M+H]$^+$.

Example 8: 5-(2-ethoxy-3-pyridyl)-1-isopropyl-N-[(3R)-tetrahydropyran-3-yl]pyrazolo[4,3-b]pyridin-7-amine

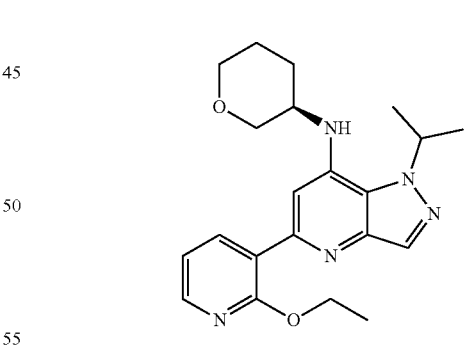

Prepared using the same procedure as described for example 1, from 2-ethoxy-3-(4,4,5,5-tetramethyl-1,3,2-dioxaborolan-2-yl)pyridine and (R)-5-bromo-1-isopropyl-N-(tetrahydro-2H-pyran-3-yl)-1H-pyrazolo[4,3-b]pyridin-7-amine. $^1$H-NMR (600 MHz, DMSO-d$_6$): δ 8.30 (s, 1H), 8.26-8.20 (m, 2H), 7.65 (s, 1H), 7.13 (dd, J=7.3, 4.9 Hz, 1H), 5.21 (hept, J=6.6 Hz, 1H), 4.69 (t, J=5.3 Hz, 1H), 4.48-4.33 (m, 2H), 3.89 (dq, J=7.0, 3.0 Hz, 1H), 3.65 (dt, J=9.5, 6.7 Hz, 1H), 3.51 (ddd, J=10.6, 5.2, 3.9 Hz, 1H), 3.40-3.31 (m, 1H), 3.03 (ddd, J=9.4, 7.2, 5.1 Hz, 1H), 2.19 (dtd, J=12.2, 7.6, 4.3 Hz, 1H), 2.02-1.87 (m, 2H), 1.88-1.78 (m, 1H), 1.71

(d, J=6.7 Hz, 3H), 1.39 (t, J=7.1 Hz, 3H), 1.15 (d, J=6.4 Hz, 3H). LC-MS: tR=0.5 min (Method D), m/z=382.1 [M+H]$^+$.

Example 9: 5-(2-ethoxy-3-pyridyl)-1-isopropyl-N-[(3S)-tetrahydropyran-3-yl]pyrazolo[4,3-b]pyridin-7-amine

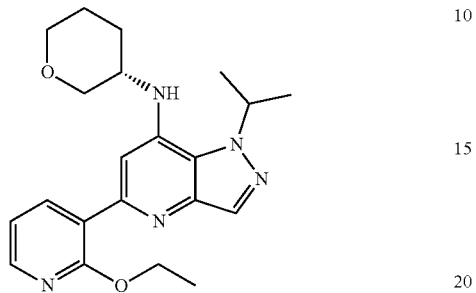

Prepared using the same procedure as described for example 1, from 2-ethoxy-3-(4,4,5,5-tetramethyl-1,3,2-dioxaborolan-2-yl)pyridine and (S)-5-bromo-1-isopropyl-N-(tetrahydro-2H-pyran-3-yl)-1H-pyrazolo[4,3-b]pyridin-7-amine. $^1$H-NMR (600 MHz, DMSO-d$_6$): δ 8.30 (s, 1H), 8.26-8.20 (m, 2H), 7.65 (s, 1H), 7.13 (dd, J=7.3, 4.9 Hz, 1H), 5.21 (hept, J=6.6 Hz, 1H), 4.69 (t, J=5.3 Hz, 1H), 4.48-4.33 (m, 2H), 3.89 (dq, J=7.0, 3.0 Hz, 1H), 3.65 (dt, J=9.5, 6.7 Hz, 1H), 3.51 (ddd, J=10.6, 5.2, 3.9 Hz, 1H), 3.40-3.31 (m, 1H), 3.03 (ddd, J=9.4, 7.2, 5.1 Hz, 1H), 2.19 (dtd, J=12.2, 7.6, 4.3 Hz, 1H), 2.02-1.87 (m, 2H), 1.88-1.78 (m, 1H), 1.71 (d, J=6.7 Hz, 3H), 1.39 (t, J=7.1 Hz, 3H), 1.15 (d, J=6.4 Hz, 3H). LC-MS: tR=0.5 min (Method D), m/z=382.1 [M+H]$^+$.

Example 10: 5-(2-ethoxy-3-pyridyl)-1-isopropyl-N-tetrahydropyran-4-yl-pyrazolo[4,3-b]pyridin-7-amine

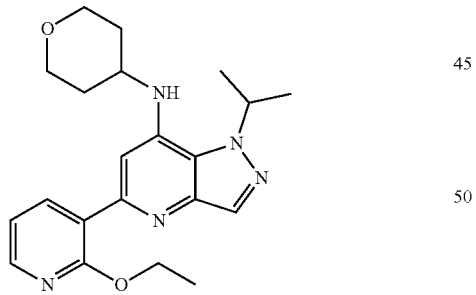

Prepared using the same procedure as described for example 1, from 2-ethoxy-3-(4,4,5,5-tetramethyl-1,3,2-dioxaborolan-2-yl)pyridine and 5-bromo-1-isopropyl-N-(tetrahydro-2H-pyran-4-yl)-1H-pyrazolo[4,3-b]pyridin-7-amine. $^1$H-NMR (600 MHz, DMSO-d$_6$): δ 8.22-8.16 (m, 2H), 8.10 (s, 1H), 7.20 (s, 1H), 7.10 (dd, J=7.3, 4.9 Hz, 1H), 5.94 (d, J=7.1 Hz, 1H), 5.26 (p, J=6.4 Hz, 1H), 4.42 (q, J=7.1 Hz, 2H), 3.94 (dt, J=12.0, 3.7 Hz, 2H), 3.80-3.68 (m, 1H), 3.48 (td, J=11.5, 2.1 Hz, 2H), 2.03 (dq, J=12.7, 2.1 Hz, 2H), 1.72 (dtd, J=13.1, 10.9, 4.3 Hz, 2H), 1.46 (d, J=6.4 Hz, 6H), 1.35 (t, J=7.0 Hz, 3H). LC-MS: tR=0.54 min (Method D), m/z=382.2 [M+H]$^+$.

Example 11: 5-(2-ethoxy-3-pyridyl)-1-isopropyl-N-[trans-4-methoxytetrahydrofuran-3-yl]pyrazolo[4,3-b]pyridin-7-amine

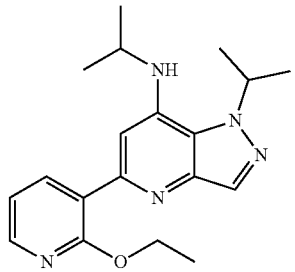 [SMILES: CCOc1ncccc1-c1cc(NC(C)C)c2c(cnn2C(C)C)n1]

Prepared using the same procedure as described for example 1, from 2-ethoxy-3-(4,4,5,5-tetramethyl-1,3,2-dioxaborolan-2-yl)pyridine and Trans-(±)-5-bromo-1-isopropyl-N-(trans-4-methoxytetrahydrofuran-3-yl)-1H-pyrazolo[4,3-b]pyridin-7-amine. $^1$H-NMR (600 MHz, DMSO-d$_6$): δ 8.24-8.16 (m, 2H), 8.14 (s, 1H), 7.23 (s, 1H), 7.11 (dd, J=7.4, 4.9 Hz, 1H), 6.21 (d, J=5.2 Hz, 1H), 5.25 (p, J=6.4 Hz, 1H), 4.50-4.37 (m, 2H), 4.18 (dd, J=9.2, 5.8 Hz, 1H), 4.10-4.03 (m, 2H), 3.92 (dd, J=10.1, 4.3 Hz, 1H), 3.83 (dd, J=10.1, 1.8 Hz, 1H), 3.79 (dd, J=9.2, 3.6 Hz, 1H), 3.30 (s, 3H), 1.45 (dd, J=13.9, 6.4 Hz, 6H), 1.38 (t, J=7.0 Hz, 3H). LC-MS: tR=0.54 min (Method D), m/z=398.1 [M+H]$^+$.

Example 12: 5-(2-ethoxy-3-pyridyl)-N,1-diisopropyl-pyrazolo[4,3-b]pyridin-7-amine Prepared using the same procedure as described for example 1, from 2-ethoxy-3-(4,4,5,5-tetramethyl-1,3,2-dioxaborolan-2-yl)pyridine and 5-bromo-N,1-diisopropyl-1H-pyrazolo[4,3-b]pyridin-7-amine. $^1$H-NMR (600 MHz, DMSO-d$_6$): δ 8.24-8.17 (m, 2H), 8.09 (s, 1H), 7.16 (s, 1H), 7.10 (dd, J=7.4, 4.9 Hz, 1H), 5.84 (d, J=7.3 Hz, 1H), 5.24 (h, J=6.5 Hz, 1H), 4.42 (q, J=7.0 Hz, 2H), 3.88-3.75 (m, 1H), 1.46 (d, J=6.4 Hz, 6H), 1.37 (t, J=7.1 Hz, 3H), 1.33 (d, J=6.3 Hz, 6H). LC-MS: tR=0.61 min (Method D), m/z=340.1 [M+H]$^+$.

Example 13: 5-(2-ethoxy-3-pyridyl)-1-isopropyl-N-methyl-pyrazolo[4,3-b]pyridin-7-amine

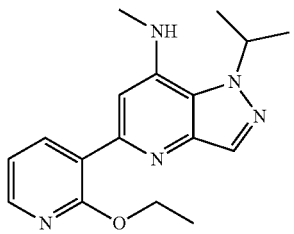 [SMILES: CCOc1ncccc1-c1cc(NC)c2c(cnn2C(C)C)n1]

Prepared using the same procedure as described for example 1, from 2-ethoxy-3-(4,4,5,5-tetramethyl-1,3,2-dioxaborolan-2-yl)pyridine and 5-bromo-1-isopropyl-N-methyl-1H-pyrazolo[4,3-b]pyridin-7-amine. $^1$H-NMR (600 MHz, DMSO-d$_6$): δ 8.24 (dd, J=7.4, 2.0 Hz, 1H), 8.20 (dd, J=4.8, 2.0 Hz, 1H), 8.10 (s, 1H), 7.12 (s, 1H), 7.10 (dd, J=7.4, 4.9 Hz, 1H), 6.46 (q, J=4.6 Hz, 1H), 5.20 (p, J=6.4 Hz, 1H), 4.43 (q, J=7.0 Hz, 2H), 2.92 (d, J=4.6 Hz, 3H), 1.48 (d, J=6.4 Hz, 6H), 1.39 (t, J=7.1 Hz, 3H). LC-MS: tR=0.5 min (Method D), m/z=312.1 [M+H]$^+$.

Example 14: 5-(2-ethoxy-3-pyridyl)-1-methyl-7-pyrrolidin-1-yl-pyrazolo[4,3-b]pyridine

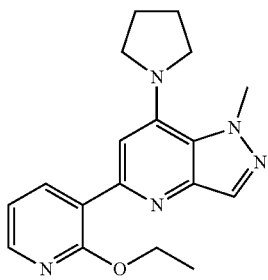 [SMILES: CCOc1ncccc1-c1cc(N2CCCC2)c2c(cnn2C)n1]

Prepared using the same procedure as described for example 1, from 2-ethoxy-3-(4,4,5,5-tetramethyl-1,3,2-dioxaborolan-2-yl)pyridine and 5-chloro-1-methyl-7-(pyrrolidin-1-yl)-1H-pyrazolo[4,3-b]pyridine. $^1$H-NMR (400 MHz, Chloroform-d): δ 8.23 (dd, J=7.6, 2.0 Hz, 1H), 8.19 (s, 1H), 8.18 (d, J=2.0 Hz, 1H), 7.44 (s, 1H), 7.02 (dd, J=7.6, 5.2 Hz, 1H), 4.47 (q, J=7.2 Hz, 2H), 4.24 (s, 3H), 3.40-3.37 (m, 4H), 2.09-1.88 (m, 4H), 1.43 (t, J=7.2 Hz, 3H). LC-MS: tR=2.23 min (Method G), m/z=324.2 [M+H]$^+$.

Example 15: 5-(2-ethoxy-3-pyridyl)-1-ethyl-3,6-dimethyl-pyrazolo[4,3-b]pyridine

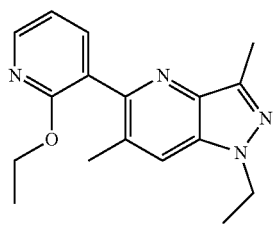 [SMILES: CCOc1ncccc1-c1nc2c(C)nn(CC)c2cc1C]

Prepared using the same procedure as described for example 1, from 2-ethoxy-3-(4,4,5,5-tetramethyl-1,3,2-dioxaborolan-2-yl)pyridine and 5-chloro-1-ethyl-3,6-dimethyl-1H-pyrazolo[4,3-b]pyridine (40 mg, 0.191 mmol). $^1$H-NMR (600 MHz, DMSO-d$_6$): δ 8.26 (dd, J=5.0, 2.0 Hz, 1H), 7.98 (s, 1H), 7.65 (dd, J=7.2, 2.0 Hz, 1H), 7.11 (dd, J=7.2, 5.0 Hz, 1H), 4.37 (q, J=7.2 Hz, 2H), 4.26 (broad s, 2H), 2.48 (s, 3H), 2.23 (s, 3H), 1.40 (t, J=7.2 Hz, 3H), 1.19 (t, J=7.0 Hz, 3H). LC-MS: tR=0.65 min (Method D), m/z=297.1 [M+H]$^+$.

Example 16: 5-(2-ethoxy-3-pyridyl)-1-ethyl-7-pyrrolidin-1-yl-pyrazolo[4,3-b]pyridine

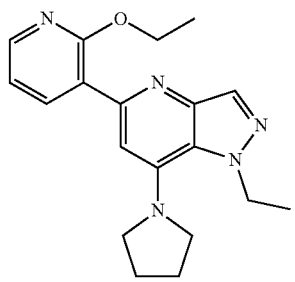 [SMILES: CCOc1ncccc1-c1cc(N2CCCC2)c2c(cnn2CC)n1]

Prepared using the same procedure as described for example 1, from 2-ethoxy-3-(4,4,5,5-tetramethyl-1,3,2-dioxaborolan-2-yl)pyridine and 5-bromo-1-ethyl-7-(pyrrolidin-1-yl)-1H-pyrazolo[4,3-b]pyridine. $^1$H-NMR (400 MHz, Chloroform-d): δ 8.24-8.17 (m, 3H), 7.49 (s, 1H), 7.04-7.01 (m, 1H), 4.52 (q, J=7.2 Hz, 2H), 4.47 (q, J=7.2 Hz, 2H), 3.40-3.30 (m, 4H), 2.09-2.00 (m, 4H), 1.49 (t, J=7.2 Hz, 3H), 1.43 (t, J=7.2 Hz, 3H). LC-MS: tR=1.67 min (Method A), m/z=338.2 [M+H]$^+$.

Example 17: 5-(2-ethoxy-3-pyridyl)-1-isopropyl-7-pyrrolidin-1-yl-pyrazolo[4,3-b]pyridine

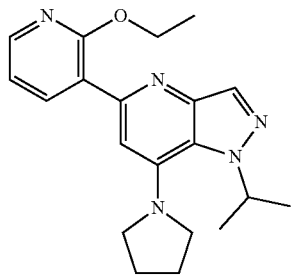 [SMILES: CCOc1ncccc1-c1cc(N2CCCC2)c2c(cnn2C(C)C)n1]

Prepared using the same procedure as described for example 1, from 2-ethoxy-3-(4,4,5,5-tetramethyl-1,3,2-dioxaborolan-2-yl)pyridine and 5-bromo-1-isopropyl-7-(pyrrolidin-1-yl)-1H-pyrazolo[4,3-b]pyridine. $^1$H-NMR (400 MHz, Chloroform-d): δ 8.29-8.25 (m, 2H), 8.18 (d, J=4.0 Hz, 1H), 7.51 (s, 1H), 7.04-7.01 (m, 1H), 5.18-5.11 (m, 1H), 4.68 (q, J=6.8 Hz, 2H), 3.31 (brs, 4H), 2.04 (brs, 4H), 1.51 (d, J=6.4 Hz, 6H), 1.44 (t, J=7.2 Hz, 3H). LC-MS: tR=1.82 min (Method K), m/z=352.2 [M+H]$^+$.

Example 18: 5-(2-ethoxy-3-pyridyl)-1-propyl-7-pyrrolidin-1-yl-pyrazolo[4,3-b]pyridine

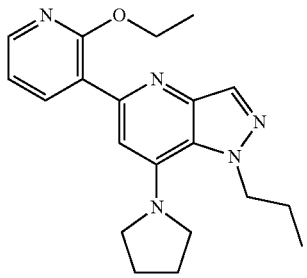 [SMILES: CCCn1ncc2nc(-c3cccnc3OCC)cc(N3CCCC3)c21]

Prepared using the same procedure as described for example 1, from 2-ethoxy-3-(4,4,5,5-tetramethyl-1,3,2-dioxaborolan-2-yl)pyridine and 5-bromo-1-propyl-7-(pyrrolidin-1-yl)-1H-pyrazolo[4,3-b]pyridine. $^1$H-NMR (400 MHz, Chloroform-d): δ 8.27-8.17 (m, 3H), 7.52 (s, 1H), 7.04-7.01 (m, 1H), 4.50-4.43 (m, 4H), 3.32 (s, 4H), 2.07-1.89 (m, 6H), 1.43 (t, J=7.2 Hz, 3H), 0.85 (t, J=7.6 Hz, 3H). LC-MS: tR=1.79 min (Method A), m/z=352.2 [M+H]$^+$.

Example 19 and Example 20: 5-(2-ethoxy-3-pyridyl)-1-ethyl-N-[tetrahydrofuran-3-yl]pyrazolo[4,3-b]pyridin-7-amine, Enantiomer 1 and Enantiomer 2

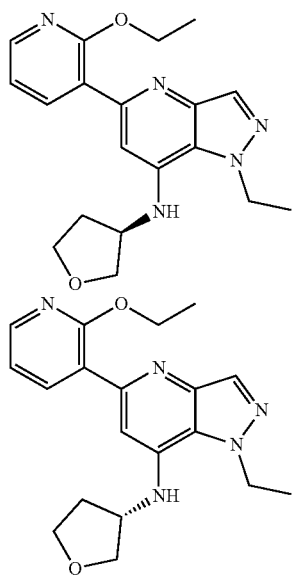

(±)-5-(2-Ethoxy-3-pyridyl)-1-ethyl-N-[tetrahydrofuran-3-yl]pyrazolo[4,3-b]pyridin-7-amine was prepared using the same procedure as described for example 1, from 2-ethoxy-3-(4,4,5,5-tetramethyl-1,3,2-dioxaborolan-2-yl)pyridine and (±)-5-bromo-1-ethyl-N-(tetrahydrofuran-3-yl)-1H-pyrazolo[4,3-b]pyridin-7-amine followed by separation by chiral SFC to afford 5-(2-ethoxy-3-pyridyl)-1-ethyl-N-[tetrahydrofuran-3-yl]pyrazolo[4,3-b]pyridin-7-amine, enantiomer 1 and enantiomer 2.

Example 19

5-(2-ethoxy-3-pyridyl)-1-ethyl-N-[tetrahydrofuran-3-yl]pyrazolo[4,3-b]pyridin-7-amine enantiomer 1. $^1$H-NMR (400 MHz, Chloroform-d): δ 8.21-8.18 (m, 2H), 8.10 (s, 1H), 7.10 (s, 1H), 7.04-7.00 (m, 1H), 4.60-4.56 (m, 3H), 4.49-4.47 (m, 2H), 4.30-4.29 (m, 1H), 4.06-4.02 (m, 2H), 3.94-3.92 (m, 2H), 2.46-2.37 (m, 1H), 2.10-2.07 (m, 1H), 1.54-1.52 (m, 3H), 1.42 (t, J=7.2 Hz, 3H). [α]$^{20}_D$=+7.00 (c=0.10, MeOH). LC-MS: tR=1.81 min (Method C), m/z=354.2 [M+H]$^+$.

Example 20

5-(2-ethoxy-3-pyridyl)-1-ethyl-N-[tetrahydrofuran-3-yl]pyrazolo[4,3-b]pyridin-7-amine enantiomer 2. $^1$H-NMR (400 MHz, Chloroform-d): δ 8.21-8.19 (m, 2H), 8.10 (s, 1H), 7.10 (s, 1H), 7.04-7.01 (m, 1H), 4.60-4.56 (m, 3H), 4.51-4.48 (m, 2H), 4.30-4.29 (m, 1H), 4.06-4.02 (m, 2H), 3.94-3.92 (m, 2H), 2.46-2.37 (m, 1H), 2.10-2.07 (m, 1H), 1.54-1.52 (m, 3H), 1.42 (t, J=7.2 Hz, 3H). [α]$^{20}_D$=−6.00 (c=0.10, MeOH). LC-MS: tR=1.81 min (Method C), m/z=354.2 [M+H]$^+$.

Example 21 and Example 22: 5-(2-ethoxy-3-pyridyl)-1-isopropyl-N-[tetrahydrofuran-3-yl]pyrazolo[4,3-b]pyridin-7-amine, Enantiomer 1 and Enantiomer 2

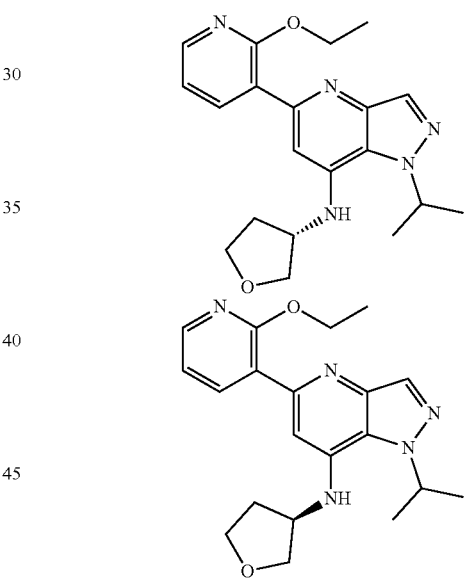

(±)-5-(2-ethoxy-3-pyridyl)-1-isopropyl-N-[tetrahydrofuran-3-yl]pyrazolo[4,3-b]pyridin-7-amine was prepared using the same procedure as described for example 1, from 2-ethoxy-3-(4,4,5,5-tetramethyl-1,3,2-dioxaborolan-2-yl)pyridine and (±)-5-bromo-1-isopropyl-N-(tetrahydrofuran-3-yl)-1H-pyrazolo[4,3-b]pyridin-7-amine followed by separation by chiral SFC to afford 5-(2-ethoxy-3-pyridyl)-1-isopropyl-N-[tetrahydrofuran-3-yl]pyrazolo[4,3-b]pyridin-7-amine, enantiomer 1 and enantiomer 2.

Example 21

5-(2-ethoxy-3-pyridyl)-1-isopropyl-N-[tetrahydrofuran-3-yl]pyrazolo[4,3-b]pyridin-7-amine, enantiomer 1. $^1$H-NMR (400 MHz, Chloroform-d): δ 8.22-8.16 (m, 3H), 7.12 (s, 1H), 7.05-7.02 (m, 1H), 4.88-4.86 (m, 1H), 4.65-4.63 (m, 1H), 4.47 (q, J=6.8 Hz, 2H), 4.32-4.31 (m, 1H), 4.08-4.06 (m, 2H), 4.05-3.94 (m, 2H), 2.47-2.38 (m, 1H), 2.12-2.09 (m, 1H), 1.66 (d, J=6.4 Hz, 6H), 1.43 (t, J=7.2 Hz, 3H). [α]°2°=+8.00 (c=0.10, MeOH). LC-MS: tR=1.92 min (Method C), m/z=368.2 [M+H]⁺.

Example 22

5-(2-ethoxy-3-pyridyl)-1-isopropyl-N-[tetrahydrofuran-3-yl]pyrazolo[4,3-b]pyridin-7-amine, enantiomer 2. ¹H-NMR (400 MHz, Chloroform-d): δ 8.23-8.16 (m, 3H), 7.12 (s, 1H), 7.05-7.02 (m, 1H), 4.90-4.85 (m, 1H), 4.65-4.63 (m, 1H), 4.49 (q, J=6.8 Hz, 2H), 4.32-4.31 (m, 1H), 4.08-4.04 (m, 2H), 3.96-3.94 (m, 2H), 2.47-2.38 (m, 1H), 2.12-2.09 (m, 1H), 1.66 (d, J=6.0 Hz, 6H), 1.43 (t, J=7.2 Hz, 3H). [α]°2°=−7.00 (c=0.10, MeOH). LC-MS: tR=1.91 min (Method C), m/z=368.2 [M+H]⁺.

Example 23: 5-(2-ethoxy-3-pyridyl)-1-propyl-N-[tetrahydrofuran-3-yl]pyrazolo[4,3-b]pyridin-7-amine, Enantiomer 1 and Enantiomer 2

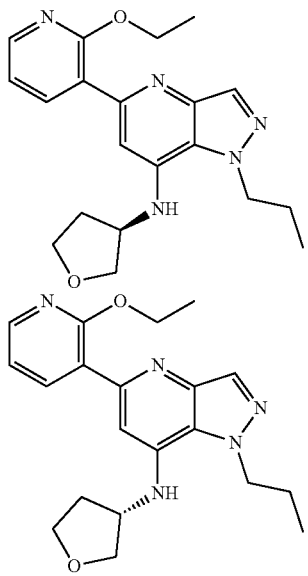

(±)-5-(2-Ethoxy-3-pyridyl)-1-propyl-N-[tetrahydrofuran-3-yl]pyrazolo[4,3-b]pyridin-7-amine was prepared using the same procedure as described for example 1, from 2-ethoxy-3-(4,4,5,5-tetramethyl-1,3,2-dioxaborolan-2-yl)pyridine and (±)-5-bromo-1-propyl-N-(tetrahydrofuran-3-yl)-1H-pyrazolo[4,3-b]pyridin-7-amine followed by separation by chiral SFC to afford 5-(2-ethoxy-3-pyridyl)-1-propyl-N-[tetrahydrofuran-3-yl]pyrazolo[4,3-b]pyridin-7-amine, enantiomer 1 and enantiomer 2.

Example 23

5-(2-ethoxy-3-pyridyl)-1-propyl-N-[tetrahydrofuran-3-yl]pyrazolo[4,3-b]pyridin-7-amine, enantiomer 1. ¹H-NMR (400 MHz, Chloroform-d): δ 8.21-8.18 (m, 2H), 8.09 (s, 1H), 7.10 (s, 1H), 7.04-7.01 (m, 1H), 4.59-4.57 (m, 3H), 4.51-4.46 (m, 2H), 4.29-4.28 (m, 1H), 4.05-4.01 (m, 2H), 3.94-3.90 (m, 2H), 2.44-2.38 (m, 1H), 2.08-2.05 (m, 1H), 1.97-1.92 (m, 2H), 1.42 (t, J=7.0 Hz, 3H), 0.98 (t, J=7.2 Hz, 3H). [α]°2°=+8.00 (c=0.10, MeOH). LC-MS: tR=1.64 min (Method A), m/z=368.2 [M+H]⁺.

Example 24

5-(2-ethoxy-3-pyridyl)-1-propyl-N-[tetrahydrofuran-3-yl]pyrazolo[4,3-b]pyridin-7-amine, enantiomer 2. ¹H-NMR (400 MHz, Chloroform-d): δ 8.22-8.18 (m, 2H), 8.09 (s, 1H), 7.10 (s, 1H), 7.04-7.00 (m, 1H), 4.59-4.57 (m, 3H), 4.51-4.46 (m, 2H), 4.29-4.28 (m, 1H), 4.05-4.01 (m, 2H), 3.94-3.90 (m, 2H), 2.45-2.38 (m, 1H), 2.08-2.05 (m, 1H), 1.97-1.91 (m, 2H), 1.42 (t, J=7.0 Hz, 3H), 0.98 (t, J=7.4 Hz, 3H). [α]°2°=−6.00 (c=0.10, MeOH). LC-MS: tR=1.63 min (Method A), m/z=368.2 [M+H]⁺.

Example 25: 1-isopropyl-5-(3-pyridyl)-N-[(3R)-tetrahydrofuran-3-yl]pyrazolo[4,3-b]pyridin-7-amine

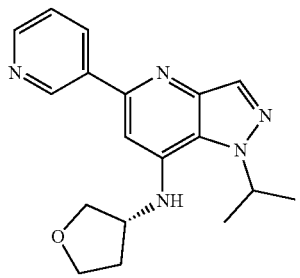 [SMILES: CC(C)n1ncc2nc(-c3cccnc3)cc(N[C@@H]3CCOC3)c21]

Prepared using the same procedure as described for example 1, from pyridin-3-ylboronic acid and (R)-5-bromo-1-isopropyl-N-(tetrahydrofuran-3-yl)-1H-pyrazolo[4,3-b]pyridin-7-amine. ¹H-NMR (400 MHz, Chloroform-d): δ 9.14 (s, 1H), 8.65 (brs, 1H), 8.35 (d, J=8.0 Hz, 1H), 8.19 (s, 1H), 7.84-7.41 (m, 1H), 6.78 (s, 1H), 4.87-4.82 (m, 1H), 4.78-4.77 (m, 1H), 4.38 (brs, 1H), 4.09-4.05 (m, 2H), 3.99-3.94 (m, 2H), 2.52-2.43 (m, 1H), 2.11-2.08 (m, 1H), 1.67 (d, J=6.0 Hz, 6H). [α]$_D^{20}$=−12.0 (c=0.10, MeOH). LC-MS: tR=1.54 min (Method C), m/z=324.1 [M+H]⁺.

Example 26: 1-isopropyl-5-pyrimidin-5-yl-N-[(3R)-tetrahydrofuran-3-yl]pyrazolo[4,3-b]pyridin-7-amine

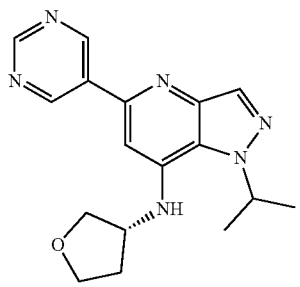 [SMILES: CC(C)n1ncc2nc(-c3cncnc3)cc(N[C@@H]3CCOC3)c21]

Prepared using the same procedure as described for example 1, from pyrimidin-5-ylboronic acid and (R)-5-bromo-1-isopropyl-N-(tetrahydrofuran-3-yl)-1H-pyrazolo[4,3-b]pyridin-7-amine. ¹H-NMR (400 MHz, Chloroform-d): δ 9.32 (s, 2H), 9.26 (s, 1H), 8.20 (s, 1H), 6.73 (s, 1H), 4.88-4.82 (m, 2H), 4.10-4.08 (brs, 1H), 4.08-4.05 (m, 2H), 4.00-3.95 (m, 2H), 2.52-2.45 (m, 1H), 2.11-2.07 (m, 1H), 1.68 (d, J=6.4 Hz, 6H). [α]$_D^{20}$=−6 (c=0.10, MeOH). LC-MS: tR=1.52 min (Method C), m/z=325.1 [M+H]⁺.

Example 27: 1-isopropyl-5-phenyl-N-[(3R)-tetrahydrofuran-3-yl]pyrazolo[4,3-b]pyridin-7-amine

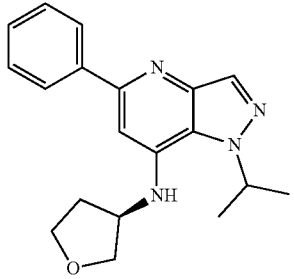 [SMILES: CC(C)n1ncc2nc(-c3ccccc3)cc(N[C@@H]3CCOC3)c21]

Prepared using the same procedure as described for example 1, from phenylboronic acid and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.19 (s, 1H), 7.96 (d, J=7.2 Hz, 2H), 7.53-7.40 (m, 3H), 6.79 (s, 1H), 4.88-4.83 (m, 1H), 4.76-4.63 (m, 1H), 4.42-4.34 (m, 1H), 4.09-4.04 (m, 2H), 3.98-3.93 (m, 2H), 2.50-2.42 (m, 1H), 2.11-2.07 (m, 1H), 1.66 (d, J=6.4 Hz, 6H). $[α]_D^{20}$= −12.00 (c=0.10, MeOH). LC-MS: tR=1.65 min (Method A), m/z=323.2 [M+H]$^+$.

Example 28: 1-isopropyl-5-(2-methoxy-3-pyridyl)-N-[(3R)-tetrahydrofuran-3-yl]pyrazolo[4,3-b]pyridin-7-amine

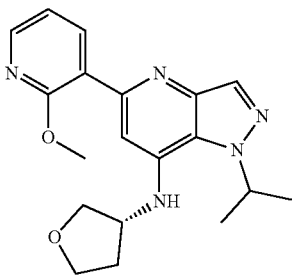 [SMILES: COc1ncccc1-c1cc(N[C@@H]2CCOC2)c2c(cnn2C(C)C)n1]

Prepared using the same procedure as described for example 1, from (2-methoxypyridin-3-yl)boronic acid and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.23 (d, J=4.8 Hz, 1H), 7.20-7.13 (m, 2H), 7.07-7.04 (m, 1H), 7.02 (s, 1H), 4.89-4.84 (m, 1H), 4.69-4.61 (m, 1H), 4.36-4.28 (m, 1H), 4.10-4.13 (m, 5H), 3.96-3.92 (m, 2H), 2.48-2.39 (m, 1H), 2.12-2.09 (m, 1H), 1.62 (d, J=6.4 Hz, 6H). [α]° 2°=−8.00 (c=0.10, MeOH). LC-MS: tR=1.84 min (Method C), m/z=354.1 [M+H]$^+$.

Example 29: 1-isopropyl-5-(2-methoxy-6-methyl-3-pyridyl)-N-[(3R)-tetrahydrofuran-3-yl]pyrazolo[4,3-b]pyridin-7-amine

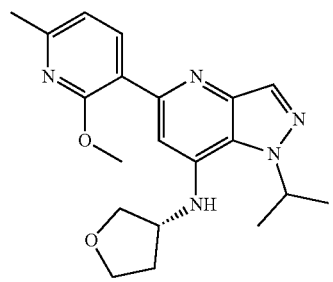 [SMILES: COc1nc(C)ccc1-c1cc(N[C@@H]2CCOC2)c2c(cnn2C(C)C)n1]

Prepared using the same procedure as described for example 1, from (2-methoxy-6-methylpyridin-3-yl)boronic acid and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.16 (s, 1H), 8.08 (d, J=7.2 Hz, 1H), 7.04 (s, 1H), 6.89 (d, J=7.6 Hz, 1H), 4.89-4.84 (m, 1H), 4.67-4.55 (m, 1H), 4.35-4.42 (m, 1H), 4.10-4.02 (m, 5H), 3.97-3.94 (m, 2H), 2.52 (s, 3H), 2.47-2.38 (m, 1H), 2.12-2.09 (m, 1H), 1.65 (d, J=6.4 Hz, 6H). [α]° 2°=−8 (c=0.10, MeOH). LC-MS: tR=1.99 min (Method C), m/z=368.2 [M+H]$^+$.

Example 30: 1-isopropyl-5-(3-methoxy-4-pyridyl)-N-[(3R)-tetrahydrofuran-3-yl]pyrazolo[4,3-b]pyridin-7-amine

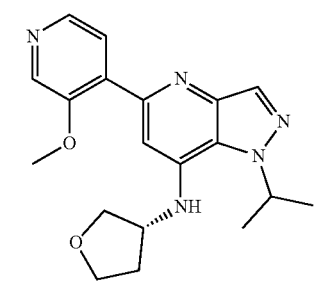 [SMILES: COc1cnccc1-c1cc(N[C@@H]2CCOC2)c2c(cnn2C(C)C)n1]

Prepared using the same procedure as described for example 1, from 3-methoxy-4-(4,4,5,5-tetramethyl-1,3,2-dioxaborolan-2-yl)pyridine and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.44 (s, 1H), 8.40 (d, J=4.4 Hz, 1H), 8.19 (s, 1H), 7.74 (d, J=4.8 Hz, 1H), 6.96 (s, 1H), 4.88-4.83 (m, 1H), 4.69-4.68 (brs, 1H), 4.31 (brs, 1H), 4.08-4.04 (m, 2H), 3.98-3.94 (m, 5H), 2.48-2.39 (m, 1H), 2.11-2.07 (m, 1H), 1.68-1.65 (m, 6H). $[a]_D^{20}$=−4.7 (c=0.10, MeOH). LC-MS: tR=1.58 min (Method C), m/z=354.1 [M+H]$^+$.

Example 31: 1-isopropyl-5-(4-methoxy-3-pyridyl)-N-[(3R)-tetrahydrofuran-3-yl]pyrazolo[4,3-b]pyridin-7-amine

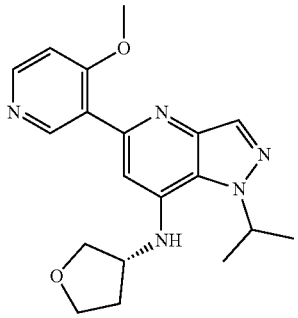 [SMILES: COc1ccncc1-c1cc(N[C@@H]2CCOC2)c2c(cnn2C(C)C)n1]

Prepared using the same procedure as described for example 1, from (4-methoxypyridin-3-yl)boronic acid and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.79 (s, 1H), 8.54 (d, J=5.6 Hz, 1H), 8.18 (s, 1H), 6.93 (d, J=5.6 Hz, 1H), 6.75 (s, 1H), 4.89-4.83 (m, 1H), 4.68-4.67 (m, 1H), 4.30 (brs, 1H), 4.06-4.02 (m, 2H), 3.96-3.93 (m, 5H), 2.45-2.37 (m, 1H), 2.10-2.07 (m, 1H), 1.67-1.66 (m, 6H). [α]$^{20}_D$=−8 (c=0.10, MeOH). LC-MS: tR=1.41 min (Method C), m/z=354.2 [M+H]$^+$.

Example 32: 5-(1,3-benzodioxol-4-yl)-1-isopropyl-N-[(3R)-tetrahydrofuran-3-yl]pyrazolo[4,3-b]pyridin-7-amine

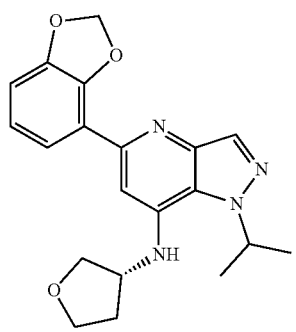 [SMILES: CC(C)n1ncc2nc(-c3cccc4c3OCO4)cc(N[C@@H]3CCOC3)c21]

Prepared using the same procedure as described for example 1, from benzo[d][1,3]dioxol-4-ylboronic acid and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.19 (s, 1H), 7.66 (d, J=8.0 Hz, 1H), 7.00-6.96 (m, 1H), 7.09 (s, 1H), 6.89 (d, J=7.2 Hz, 1H), 6.08 (s, 2H), 4.86-4.83 (m, 1H), 4.66-4.64 (m, 1H), 4.48-4.32 (m, 1H), 4.10-4.06 (m, 2H), 3.97-3.91 (m, 4H), 2.47-2.40 (m, 1H), 2.09-2.06 (m, 1H), 1.65 (d, J=6.4 Hz, 6H). [α]$^{20}_D$=−10 (c=0.10, MeOH). LC-MS: tR=1.69 min (Method A), m/z=367.1 [M+H]$^+$.

Example 33: 5-(4-ethoxyphenyl)-1-isopropyl-N-[(3R)-tetrahydrofuran-3-yl]pyrazolo[4,3-b]pyridin-7-amine

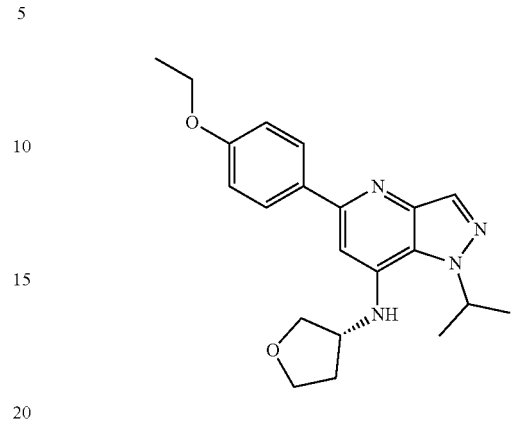

Prepared using the same procedure as described for example 1, from (4-ethoxyphenyl)boronic acid and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.17 (s, 1H), 7.91 (d, J=8.8 Hz, 2H), 7.00 (d, J=8.8 Hz, 2H), 6.74 (s, 1H), 4.87-4.80 (m, 1H), 4.73-4.61 (m, 1H), 4.42-4.33 (m, 1H), 4.33-4.05 (m, 4H), 3.97-3.94 (m, 2H), 2.50-2.43 (m, 1H), 2.10-2.02 (m, 1H), 1.65 (d, J=6.0 Hz, 6H), 1.40 (t, J=7.0 Hz, 3H). [α]$^{20}_D$=−8 (c=0.10, MeOH). LC-MS: tR=1.83 min (Method A), m/z=367.2 [M+H]$^+$.

Example 34: 5-(2-ethoxy-4-methyl-3-pyridyl)-1-isopropyl-N-[(3R)-tetrahydrofuran-3-yl]pyrazolo[4,3-b]pyridin-7-amine

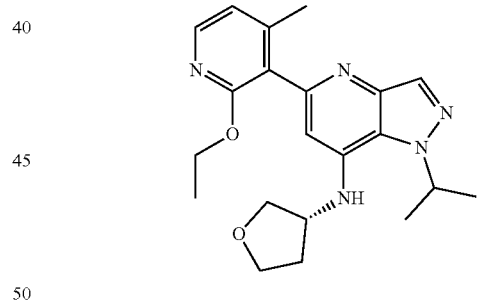

Prepared using the same procedure as described for example 1, from 2-ethoxy-4-methyl-3-(4,4,5,5-tetramethyl-1,3,2-dioxaborolan-2-yl)pyridine and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.13 (s, 1H), 8.06 (d, J=5.2 Hz, 1H), 6.83 (d, J=4.8 Hz, 1H), 6.43 (s, 1H), 4.89-4.88 (m, 1H), 4.66 (brs, 1H), 4.35 (q, J=6.8 Hz, 2H), 4.25 (brs, 1H), 4.07-3.98 (m, 2H), 3.93 (d, J=8.4 Hz, 2H), 2.41-2.36 (m, 2H), 2.19 (s, 3H), 2.06 (brs, 1H), 1.70-1.68 (m, 6H), 1.26 (t, J=6.8 Hz, 3H). [a]$^{20}_D$=−6.0 (c=0.10, MeOH). LC-MS: tR=1.9 min (Method C), m/z=382.2 [M+H]$^+$.

Example 35: 1-isopropyl-5-pyrazolo[1,5-a]pyridin-3-yl-N-[(3R)-tetrahydrofuran-3-yl]pyrazolo[4,3-b]pyridin-7-amine

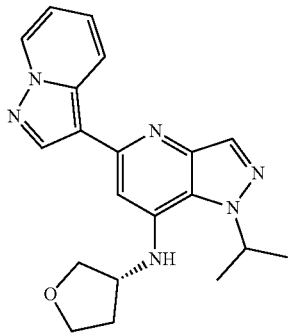 [SMILES: CC(C)n1ncc2nc(-c3cnn4ccccc34)cc(N[C@@H]3CCOC3)c21]

Prepared using the same procedure as described for example 1, from 3-(4,4,5,5-tetramethyl-1,3,2-dioxaborolan-2-yl)pyrazolo[1,5-a]pyridine and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.61 (d, J=8.8 Hz, 1H), 8.51 (d, J=7.2 Hz, 1H), 8.35 (s, 1H), 8.13 (s, 1H), 7.29 (t, J=7.6 Hz, 1H), 6.86 (t, J=6.4 Hz, 1H), 6.72 (s, 1H), 4.87-4.82 (m, 1H), 4.65 (brs, 1H), 4.40-4.39 (m, 1H), 4.11-4.07 (m, 2H), 3.97-3.95 (m, 2H), 2.52-2.43 (m, 1H), 2.12-2.09 (m, 1H), 1.66 (d, J=4.8 Hz, 6H). [a]$_D^{20}$=−10.0 (c=0.10, MeOH). LC-MS: tR=1.8 min (Method C), m/z=363.2 [M+H]$^+$.

Example 36: 5-(2-tert-butoxy-3-pyridyl)-1-isopropyl-N-[(3R)-tetrahydrofuran-3-yl]pyrazolo[4,3-b]pyridin-7-amine

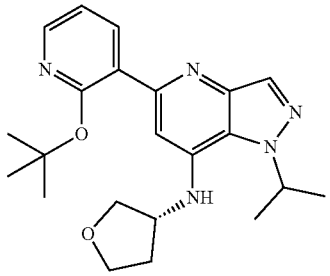 [SMILES: CC(C)n1ncc2nc(-c3cccnc3OC(C)(C)C)cc(N[C@@H]3CCOC3)c21]

Prepared using the same procedure as described for example 1, from (2-(tert-butoxy)pyridin-3-yl)boronic acid and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.18-8.13 (m, 3H), 7.08 (s, 1H), 6.99-6.97 (m, 1H), 4.89-4.85 (m, 1H), 4.83 (brs, 1H), 4.30 (brs, 1H), 4.07-4.02 (m, 2H), 3.95-3.91 (m, 2H), 2.45-2.38 (m, 1H), 2.08-2.03 (m, 1H), 1.66 (d, J=6.4 Hz, 6H), 1.61 (s, 9H). [a]$_D^{20}$=−8.0 (c=0.10, MeOH). LC-MS: tR=2.35 min (Method F), m/z=396.2 [M+H]$^+$.

Example 37: 1-isopropyl-5-[(3-methoxyphenyl)methyl]-N-[(3R)-tetrahydrofuran-3-yl]pyrazolo[4,3-b]pyridin-7-amine

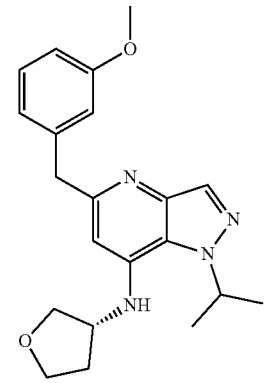 [SMILES: COc1cccc(Cc2cc(N[C@@H]3CCOC3)c3c(cnn3C(C)C)n2)c1]

Prepared using the same procedure as described for example 1, from 2-(3-methoxybenzyl)-4,4,5,5-tetramethyl-1,3,2-dioxaborolane and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.12 (s, 1H), 7.25-7.21 (m, 2H), 6.92-6.90 (m, 1H), 6.79-6.77 (m, 1H), 6.17 (s, 1H), 4.81-4.76 (m, 1H), 4.25-4.11 (m, 3H), 4.02-3.83 (m, 6H), 3.79 (s, 1H), 2.35-2.26 (m, 1H), 1.98-1.88 (m, 1H), 1.62 (d, J=6.4 Hz, 6H). [α]°2°=−4.33 (c=0.10, MeOH). LC-MS: tR=1.74 min (Method A), m/z=367.2 [M+H]$^+$.

Example 38: 5-(2,5-dimethoxy-4-pyridyl)-1-isopropyl-N-[(3R)-tetrahydrofuran-3-yl]pyrazolo[4,3-b]pyridin-7-amine

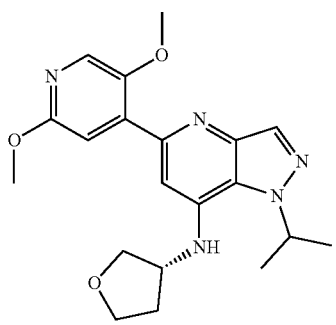 [SMILES: COc1cc(-c2cc(N[C@@H]3CCOC3)c3c(cnn3C(C)C)n2)c(OC)cn1]

Prepared using the same procedure as described for example 1, from (2,5-dimethoxypyridin-4-yl)boronic acid and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.18 (s, 1H), 7.92 (s, 1H), 7.17 (s, 1H), 6.90 (s, 1H), 4.89-4.84 (m, 1H), 4.67 (brs, 1H), 4.30 (brs, 1H), 4.07-4.03 (m, 2H), 3.95-3.92 (m, 5H), 3.86 (s, 3H), 2.47-2.38 (m, 1H), 2.09-2.06 (m, 1H), 1.67-1.65 (m, 6H). [a]$_D^{20}$=−10.0 (c=0.10, MeOH). LC-MS: tR=2 min (Method B), m/z=384.2 [M+H]$^+$.

Example 39: 1-isopropyl-5-(3-methyl-2-pyridyl)-N-[(3R)-tetrahydrofuran-3-yl]pyrazolo[4,3-b]pyridin-7-amine

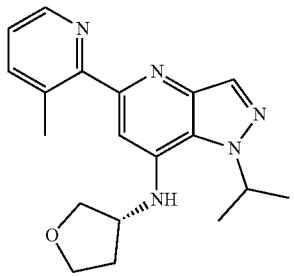 [SMILES: Cc1cccnc1-c1cc(N[C@@H]2CCOC2)c2c(cnn2C(C)C)n1]

Prepared using the same procedure as described for example 1, from (3-methylpyridin-2-yl)boronic acid and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.53 (d, J=4.0 Hz, 1H), 8.14 (s, 1H), 7.63 (d, J=7.6 Hz, 1H), 7.25-7.21 (m, 1H), 6.88 (s, 1H), 4.90-4.86 (m, 1H), 4.68 (brs, 1H), 4.40 (brs, 1H), 4.07-4.00 (m, 2H), 3.93-3.90 (m, 2H), 2.55 (s, 3H), 2.44-2.39 (m, 1H), 2.08-2.03 (m, 1H), 1.68-1.60 (m, 6H). $[α]_D^{20}$=−8 (c=0.10, MeOH). LC-MS: tR=1.7 min (Method C), m/z=338.2 [M+H]$^+$.

Example 40: 1-isopropyl-5-(3-methoxy-2-pyridyl)-N-[(3R)-tetrahydrofuran-3-yl]pyrazolo[4,3-b]pyridin-7-amine

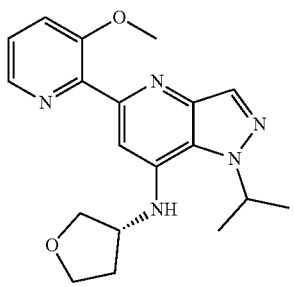 [SMILES: COc1cccnc1-c1cc(N[C@@H]2CCOC2)c2c(cnn2C(C)C)n1]

Prepared using the same procedure as described for example 1, from 3-methoxy-2-(tributylstannyl)pyridine and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.38 (d, J=3.6 Hz, 1H), 8.23 (s, 1H), 7.45-7.28 (m, 2H), 6.98 (s, 1H), 4.93-4.88 (m, 2H), 4.37 (brs, 1H), 4.09-4.03 (m, 2H), 3.95-3.91 (m, 5H), 2.46-2.37 (m, 1H), 2.11 (brs, 1H), 1.65-1.63 (m, 6H). $[α]_D^{20}$=−10 (c=0.10, MeOH). LC-MS: tR=1.86 min (Method C), m/z=354.2 [M+H]$^+$.

Example 41: 2-[1-isopropyl-7-[[(3R)-tetrahydrofuran-3-yl]amino]pyrazolo[4,3-b]pyridin-5-yl]benzonitrile

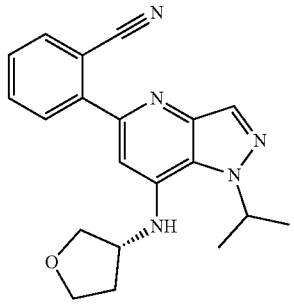 [SMILES: CC(C)n1ncc2nc(-c3ccccc3C#N)cc(N[C@@H]3CCOC3)c21]

Prepared using the same procedure as described for example 1, from (2-cyanophenyl)boronic acid and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.20 (s, 1H), 7.97 (d, J=8.0 Hz, 1H), 7.80 (d, J=7.6 Hz, 1H), 7.73-7.70 (m, 1H), 7.53-7.49 (m, 1H), 6.89 (s, 1H), 4.90-4.79 (m, 2H), 4.40-4.32 (m, 1H), 4.08-4.03 (m, 2H), 3.97-3.93 (m, 2H), 2.52-2.43 (m, 1H), 2.15-2.12 (m, 1H), 1.68 (d, J=6.8 Hz, 6H). $[α]_D^{20}$=−8.00 (c=0.10, MeOH). LC-MS: tR=2.11 min (Method B), m/z=348.1 [M+H]$^+$.

Example 42: 5-(2,3-dihydro-1,4-benzodioxin-5-yl)-1-isopropyl-N-[(3R)-tetrahydrofuran-3-yl]pyrazolo[4,3-b]pyridin-7-amine

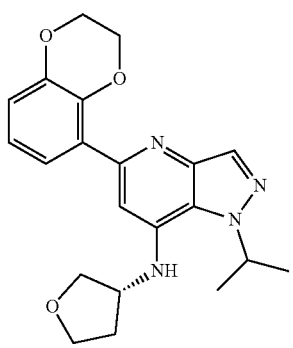 [SMILES: CC(C)n1ncc2nc(-c3cccc4c3OCCO4)cc(N[C@@H]3CCOC3)c21]

Prepared using the same procedure as described for example 1, from (2,3-dihydrobenzo[b][1,4]dioxin-5-yl)boronic acid and (R)-5-bromo-1-isopropyl-N-(tetrahydrofuran-3-yl)-1H-pyrazolo[4,3-b]pyridin-7-amine. $^1$H NMR (400 MHz, Chloroform-d): δ 8.18 (s, 1H), 7.25-7.17 (m, 1H), 6.98-6.95 (m, 2H), 6.79 (s, 1H), 4.88-4.61 (m, 2H), 4.40-4.28 (m, 5H), 4.09-4.03 (m, 2H), 3.96-3.92 (m, 2H), 2.45-2.36 (m, 1H), 2.10-2.09 (m, 1H), 1.65 (d, J=4.4 Hz, 6H). $[α]^{2°}_D$=−8 (c=0.10, MeOH). LC-MS: tR=1.81 min (Method F), m/z=381.2 [M+H]$^+$.

Example 43: 5-[(4-fluorophenyl)methyl]-1-isopropyl-N-[(3R)-tetrahydrofuran-3-yl]pyrazolo[4,3-b]pyridin-7-amine

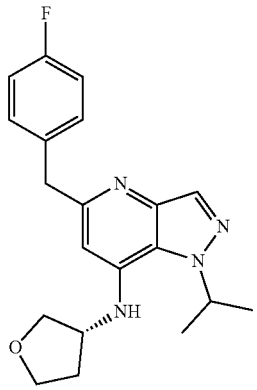 [SMILES: CC(C)n1ncc2nc(Cc3ccc(F)cc3)cc(N[C@@H]3CCOC3)c21]

Prepared using the same procedure as described for example 1, from 2-(4-fluorobenzyl)-4,4,5,5-tetramethyl-1,3,2-dioxaborolane and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.08 (s, 1H), 7.25-7.23 (m, 2H), 7.01-6.97 (m, 2H), 6.12 (s, 1H), 4.79-4.75 (m, 1H), 4.65-4.53 (m, 1H), 4.19-4.08 (m, 3H), 4.01-3.80 (m, 4H), 2.35-2.23 (m, 1H), 1.97-1.86 (m, 1H), 1.62 (d, J=6.0 Hz, 6H). $[α]°$ 2°=−22 (c=0.10, MeOH). LC-MS: tR=1.76 min (Method A), m/z=355.2 [M+H]$^+$.

Example 44: 5-[1-isopropyl-7-[[(3R)-tetrahydrofuran-3-yl]amino]pyrazolo[4,3-b]pyridin-5-yl]pyridine-3-carbonitrile

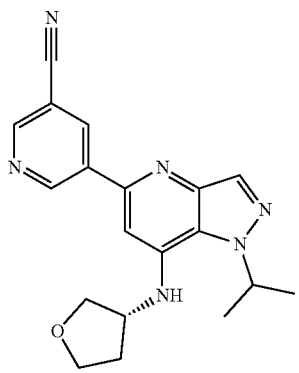 [SMILES: CC(C)n1ncc2nc(-c3cncc(C#N)c3)cc(N[C@@H]3CCOC3)c21]

Prepared using the same procedure as described for example 1, from (5-cyanopyridin-3-yl)boronic acid and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 9.37 (s, 1H), 8.90 (s, 1H), 8.64 (s, 1H), 8.19 (s, 1H), 6.76 (s, 1H), 4.91-4.78 (m, 2H), 4.43-4.36 (m, 1H), 4.12-4.05 (m, 2H), 4.00-3.96 (m, 2H), 2.52-2.47 (m, 1H), 2.15-2.03 (m, 1H), 1.68 (d, J=6.4 Hz, 6H).

Example 45: 1-isopropyl-5-[3-(methoxymethyl)phenyl]-N-[(3R)-tetrahydrofuran-3-yl]pyrazolo[4,3-b]pyridin-7-amine

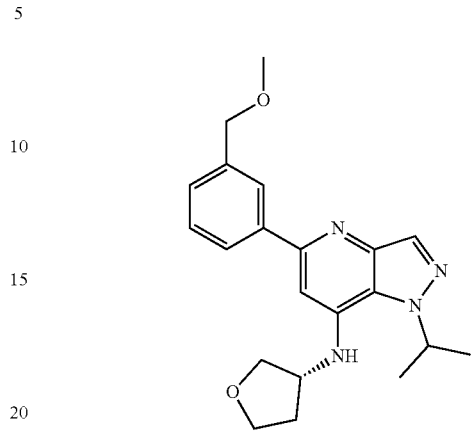

Prepared using the same procedure as described for example 1, from (3-(methoxymethyl)phenyl)boronic acid and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.19 (s, 1H), 7.94 (s, 1H), 7.88 (d, J=7.6 Hz, 1H), 7.50-7.41 (m, 2H), 6.79 (s, 1H), 4.87-4.82 (m, 1H), 4.71 (brs, 1H), 4.58 (s, 2H), 4.41-4.39 (m, 1H), 4.08-4.07 (m, 2H), 3.98-3.93 (m, 2H), 3.44 (s, 3H), 2.51-2.42 (m, 1H), 2.15-2.04 (m, 1H), 1.66 (d, J=6.0 Hz, 6H). $[α]_D^{20}$=−19.33 (c=0.20, MeOH). LC-MS: tR=1.67 min (Method A), m/z=367.2 [M+H]$^+$.

Example 46: 5-(5-ethoxy-3-pyridyl)-1-isopropyl-N-[(3R)-tetrahydrofuran-3-yl]pyrazolo[4,3-b]pyridin-7-amine

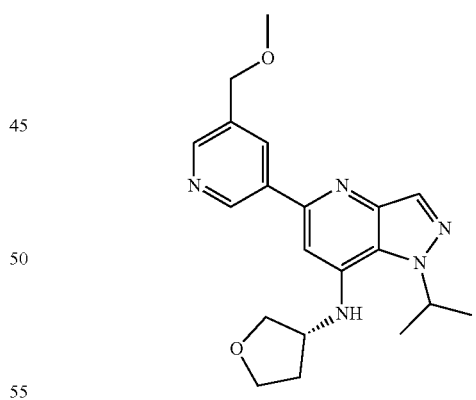

Prepared using the same procedure as described for example 1, from 3-ethoxy-5-(4,4,5,5-tetramethyl-1,3,2-dioxaborolan-2-yl)pyridine and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.70 (s, 1H), 8.35 (s, 1H), 8.20 (s, 1H), 7.94 (s, 1H), 6.79 (s, 1H), 4.90-4.70 (m, 2H), 4.38 (brs, 1H), 4.23 (q, J=6.8 Hz, 2H), 4.11-4.03 (m, 2H), 4.00-3.91 (m, 2H), 2.51-2.44 (m, 1H), 2.12-2.06 (m, 1H), 1.67 (d, J=8.0 Hz, 6H), 1.49 (t, J=7.0 Hz, 3H). $[α]°$ 2°=−10.6 (c=0.10, MeOH). LC-MS: tR=1.39 min (Method A), m/z=368.3 [M+H]$^+$.

Example 47: 1-isopropyl-5-(5-methoxy-3-pyridyl)-N-[(3R)-tetrahydrofuran-3-yl]pyrazolo[4,3-b]pyridin-7-amine

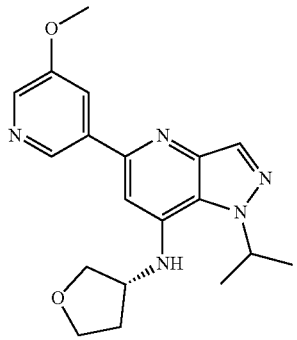 [SMILES: COc1cncc(-c2cc(N[C@@H]3CCOC3)c3c(cnn3C(C)C)n2)c1]

Prepared using the same procedure as described for example 1, from 3-methoxy-5-(4,4,5,5-tetramethyl-1,3,2-dioxaborolan-2-yl)pyridine and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.71 (s, 1H), 8.36 (s, 1H), 8.19 (s, 1H), 7.93 (s, 1H), 6.79 (s, 1H), 4.88-4.77 (m, 2H), 4.38 (brs, 1H), 4.09-4.04 (m, 2H), 3.98-3.94 (m, 5H), 2.50-2.44 (m, 1H), 2.10-2.07 (m, 1H), 1.68-1.66 (m, 6H). [α]°2°=−10 (c=0.10, MeOH). LC-MS: tR=1.71 min (Method C), m/z=354.2 [M+H]$^+$.

Example 48: 5-[3-(difluoromethoxy)phenyl]-1-isopropyl-N-[(3R)-tetrahydrofuran-3-yl]pyrazolo[4,3-b]pyridin-7-amine

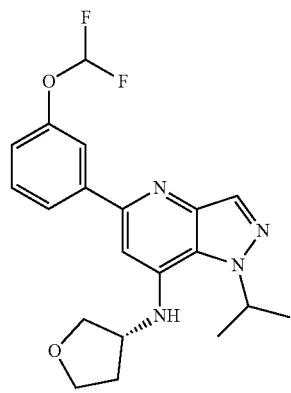 [SMILES: CC(C)n1ncc2nc(-c3cccc(OC(F)F)c3)cc(N[C@@H]3CCOC3)c21]

Prepared using the same procedure as described for example 1, from 2-(3-(difluoromethoxy)phenyl)-4,4,5,5-tetramethyl-1,3,2-dioxaborolane and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.19 (s, 1H), 7.81 (d, J=8.0 Hz, 1H), 7.75 (s, 1H), 7.48 (t, J=7.6 Hz, 1H), 7.20-7.16 (m, 1H), 6.75 (s, 1H), 6.63 (t, J=74.0 Hz, 1H), 4.88-4.80 (m, 1H), 4.73 (brs, 1H), 4.42-4.34 (m, 1H), 4.12-4.12 (m, 2H), 4.00-3.92 (m, 2H), 2.52-2.42 (m, 1H), 2.13-2.04 (m, 1H), 1.66 (d, J=6.8 Hz, 6H). [α]°2°=−6.33 (c=0.10, MeOH). LC-MS: tR=2.54 min (Method B), m/z=389.2 [M+H]$^+$.

Example 49: 1-isopropyl-5-(4-methoxypyrimidin-5-yl)-N-[(3R)-tetrahydrofuran-3-yl]pyrazolo[4,3-b]pyridin-7-amine

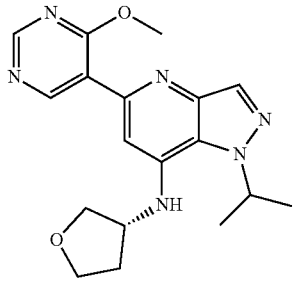 [SMILES: COc1ncncc1-c1cc(N[C@@H]2CCOC2)c2c(cnn2C(C)C)n1]

Prepared using the same procedure as described for example 1, from 4,4,4',4',5,5,5',5'-octamethyl-2,2'-bi(1,3,2-dioxaborolane), 5-bromo-4-methoxypyrimidine and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.99 (s, 1H), 8.83 (s, 1H), 8.19 (s, 1H), 6.90 (s, 1H), 4.89-4.86 (m, 1H), 4.80-4.70 (m, 1H), 4.35-4.28 (m, 1H), 4.10-4.04 (m, 5H), 3.98-3.94 (m, 2H), 2.48-2.40 (m, 1H), 2.15-2.10 (m, 1H), 1.67 (d, J=6.4 Hz, 6H). $[α]_D^{20}$=−6 (c=0.10, MeOH). LC-MS: tR=1.82 min (Method B), m/z=355.1 [M+H]$^+$.

Example 50: 5-(4-ethoxypyrimidin-5-yl)-1-isopropyl-N-[(3R)-tetrahydrofuran-3-yl]pyrazolo[4,3-b]pyridin-7-amine

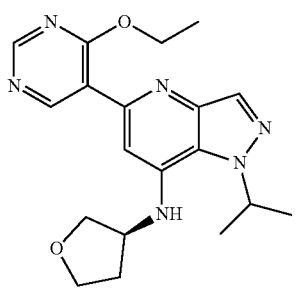 [SMILES: CCOc1ncncc1-c1cc(N[C@H]2CCOC2)c2c(cnn2C(C)C)n1]

Prepared using the same procedure as described for example 1, from 4,4,4',4',5,5,5',5'-octamethyl-2,2'-bi(1,3,2-dioxaborolane), 5-bromo-4-ethoxypyrimidine and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 9.05 (s, 1H), 8.80 (s, 1H), 8.18 (s, 1H), 7.01 (s, 1H), 4.87-4.84 (m, 1H), 4.65-4.72 (m, 1H), 4.60-4.55 (m, 2H), 4.27 (brs, 1H), 4.09-4.04 (m, 2H), 3.96-3.94 (m, 2H), 2.47-2.39 (m, 1H), 2.12-2.09 (m, 1H), 1.67 (d, J=3.2 Hz, 6H), 1.46 (t, J=7.2 Hz, 3H). $[α]_D^{20}$=−2.2 (c=0.10, MeOH). LC-MS: tR=1.81 min (Method C), m/z=369.2 [M+H]$^+$.

Example 51: 1-isopropyl-5-(5-methoxy-2-methyl-3-pyridyl)-N-[(3R)-tetrahydrofuran-3-yl]pyrazolo[4,3-b]pyridin-7-amine

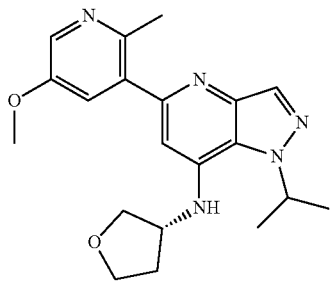 [SMILES: COc1cnc(C)c(-c2cc(N[C@@H]3CCOC3)c3c(cnn3C(C)C)n2)c1]

Prepared using the same procedure as described for example 1, from 4,4,4',4',5,5,5',5'-octamethyl-2,2'-bi(1,3,2-dioxaborolane), 3-bromo-5-methoxy-2-methylpyridine and (R)-5-bromo-1-isopropyl-N-(tetrahydrofuran-3-yl)-1H-pyrazolo[4,3-b]pyridin-7-amine. 1H-NMR (400 MHz, Chloroform-d): δ 8.27 (d, J=2.8 Hz, 1H), 8.15 (s, 1H), 7.32 (d, J=2.8 Hz, 1H), 6.44 (s, 1H), 4.87-4.82 (m, 1H), 4.76-4.74 (m, 1H), 4.27-4.26 (m, 1H), 4.05-3.99 (m, 2H), 3.95-3.88 (m, 5H), 2.54 (s, 3H), 2.43-2.36 (m, 1H), 2.06-2.01 (m, 1H), 1.67 (dd, J=3.2, 6.8 Hz, 6H). $[\alpha]_D^{20}$=−12 (c=0.10, MeOH). LC-MS: tR=1.63 min (Method C), m/z=368.2 [M+H]$^+$.

Example 52: 1-isopropyl-5-(2-methoxy-5-methyl-3-pyridyl)-N-[(3R)-tetrahydrofuran-3-yl]pyrazolo[4,3-b]pyridin-7-amine

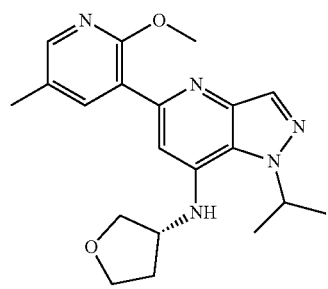 [SMILES: COc1ncc(C)cc1-c1cc(N[C@@H]2CCOC2)c2c(cnn2C(C)C)n1]

Prepared using the same procedure as described for example 1, from 4,4,4',4',5,5,5',5'-octamethyl-2,2'-bi(1,3,2-dioxaborolane), 3-bromo-2-methoxy-5-methylpyridine and (R)-5-bromo-1-isopropyl-N-(tetrahydrofuran-3-yl)-1H-pyrazolo[4,3-b]pyridin-7-amine. 1H-NMR (400 MHz, Chloroform-d): δ 8.18 (s, 1H), 8.03 (s, 2H), 7.04 (s, 1H), 4.89-4.84 (m, 1H), 4.71-4.59 (m, 1H), 4.37-4.28 (m, 1H), 4.08-3.94 (m, 7H), 2.46-2.34 (m, 1H), 2.34 (s, 3H), 2.12-2.09 (m, 1H), 1.66 (d, J=6.8 Hz, 6H). $[\alpha]_D^{20}$=−12 (c=0.10, MeOH).

LC-MS: tR=1.94 min (Method C), m/z=368.2 [M+H]$^+$.

Example 53: 5-(2-ethoxyphenyl)-1-isopropyl-N-[(3R)-tetrahydrofuran-3-yl]pyrazolo[4,3-b]pyridin-7-amine

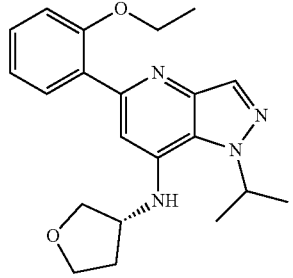 [SMILES: CCOc1ccccc1-c1cc(N[C@@H]2CCOC2)c2c(cnn2C(C)C)n1]

Prepared using the same procedure as described for example 1, from (2-ethoxyphenyl)boronic acid and (R)-5-bromo-1-isopropyl-N-(tetrahydrofuran-3-yl)-1H-pyrazolo[4,3-b]pyridin-7-amine. 1H-NMR (400 MHz, Chloroform-d): δ 8.18 (s, 1H), 7.79 (d, J=7.2 Hz, 1H), 7.38-7.34 (m, 1H), 7.11-7.07 (m, 1H), 7.02-6.98 (m, 2H), 4.89-4.85 (m, 1H), 4.68-4.55 (m, 1H), 4.33-4.25 (m, 1H), 4.13-4.02 (m, 4H), 3.94-3.92 (m, 2H), 2.43-2.38 (m, 1H), 2.15-2.05 (m, 1H), 1.66 (d, J=6.0 Hz, 6H), 1.39 (t, J=7.2 Hz, 3H). $[\alpha]_D^{20}$=−8 (c=0.10, MeOH). LC-MS: tR=1.75 min (Method A), m/z=367.1 [M+H]$^+$.

Example 54: 5-[1-isopropyl-7-[[(3R)-tetrahydrofuran-3-yl]amino]pyrazolo[4,3-b]pyridin-5-yl]-6-methoxy-pyridine-3-carbonitrile

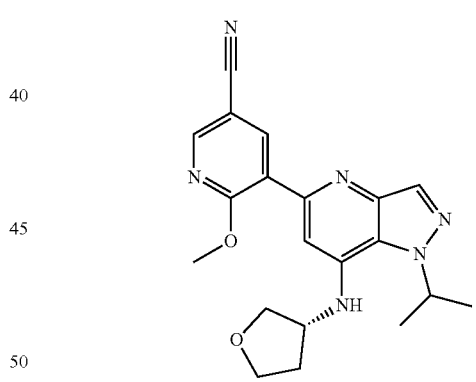

Prepared using the same procedure as described for example 1, from 4,4,4',4',5,5,5',5'-octamethyl-2,2'-bi(1,3,2-dioxaborolane), 4-bromo-6-methoxynicotinonitrile and (R)-5-bromo-1-isopropyl-N-(tetrahydrofuran-3-yl)-1H-pyrazolo[4,3-b]pyridin-7-amine. 1H-NMR (400 MHz, Chloroform-d): δ 8.52 (d, J=2.0 Hz, 1H), 8.45 (d, J=2.0 Hz, 1H), 8.16 (s, 1H), 6.98 (s, 1H), 4.89-4.84 (m, 1H), 4.72-4.71 (m, 1H), 4.28-4.27 (m, 1H), 4.10-4.05 (m, 5H), 3.96-3.95 (m, 2H), 2.49-2.40 (m, 1H), 2.11-2.08 (m, 1H), 1.66 (d, J=6.4 Hz, 6H). $[\alpha]_D^{20}$=−2 (c=0.10, MeOH). LC-MS: tR=1.88 min (Method C), m/z=379.2 [M+H]$^+$.

Example 55: 6-ethoxy-5-[1-isopropyl-7-[[(3R)-tetra-hydrofuran-3-yl]amino]pyrazolo[4,3-b]pyridin-5-yl]pyridine-3-carbonitrile

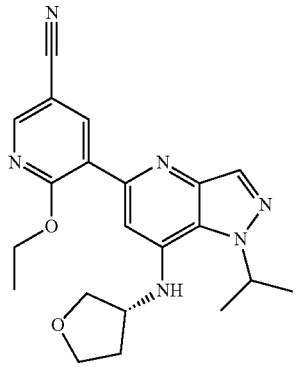 [SMILES: CCOc1ncc(C#N)cc1-c1cc(N[C@@H]2CCOC2)c2c(cnn2C(C)C)n1]

Prepared using the same procedure as described for example 1, from 4,4,4',4',5,5,5',5'-octamethyl-2,2'-bi(1,3,2-dioxaborolane), 4-bromo-6-ethoxynicotinonitrile and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.51-8.49 (m, 2H), 8.16 (s, 1H), 7.07 (s, 1H), 4.87-4.86 (m, 1H), 4.72-4.71 (m, 1H), 4.57 (q, J=6.8 Hz, 2H), 4.30-4.28 (brs, 1H), 4.09-4.03 (m, 2H), 3.96-3.94 (m, 2H), 2.46-2.41 (m, 1H), 2.13-2.08 (m, 1H), 1.66 (dd, J=6.8 Hz, 6H), 1.46 (t, J=7.2 Hz, 3H). $[α]_D^{20}$=−7.3 (c=0.10, MeOH). LC-MS: tR=2.38 min (Method B), m/z=393.2 [M+H]$^+$.

Example 56: 5-(2-ethyl-3-pyridyl)-1-isopropyl-N-[(3R)-tetrahydrofuran-3-yl]pyrazolo[4,3-b]pyridin-7-amine

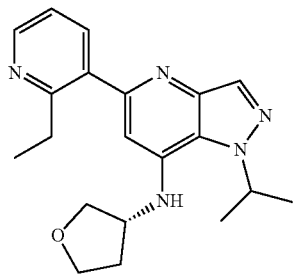 [SMILES: CCc1ncccc1-c1cc(N[C@@H]2CCOC2)c2c(cnn2C(C)C)n1]

Prepared using the same procedure as described for example 1, from (2-ethylpyridin-3-yl)boronic acid and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.62 (d, J=5.2 Hz, 1H), 8.15 (s, 1H), 7.73 (d, J=7.6 Hz, 1H), 7.25-7.23 (m, 1H), 6.44 (s, 1H), 4.90-4.85 (m, 1H), 4.80-4.70 (m, 1H), 4.30-4.22 (m, 1H), 4.08-3.99 (m, 2H), 3.94-3.92 (m, 2H), 2.92 (q, J=7.6 Hz, 2H), 2.43-2.36 (m, 1H), 2.07-2.04 (m, 1H), 1.69 (d, J=6.8 Hz, 6H), 1.26 (t, J=7.6 Hz, 3H). [α]° 2°=−6 (c=0.10, MeOH). LC-MS: tR=1.58 min (Method C), m/z=352.2 [M+H]$^+$.

Example 57: 1-isopropyl-5-[(4-methoxyphenyl)methyl]-N-[(3R)-tetrahydrofuran-3-yl]pyrazolo[4,3-b]pyridin-7-amine

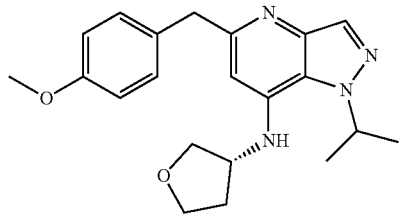 [SMILES: COc1ccc(Cc2cc(N[C@@H]3CCOC3)c3c(cnn3C(C)C)n2)cc1]

Prepared using the same procedure as described for example 1, from 2-(4-methoxybenzyl)-4,4,5,5-tetramethyl-1,3,2-dioxaborolane and (R)-5-bromo-1-isopropyl-N-(tetrahydrofuran-3-yl)-1H-pyrazolo[4,3-b]pyridin-7-amine. $^1$H-NMR (400 MHz, Chloroform-d): δ 8.10 (s, 1H), 7.24 (d, J=8.4 Hz, 2H), 6.85 (d, J=8.4 Hz, 2H), 6.14 (s, 1H), 4.81-4.74 (m, 2H), 4.19-4.10 (m, 3H), 4.01-3.82 (m, 4H), 3.79 (s, 3H), 2.35-2.27 (m, 1H), 1.94-1.91 (m, 1H), 1.62 (d, J=6.8 Hz, 6H). [α]° 2°=−4 (c=0.10, MeOH). LC-MS: tR=1.96 min (Method F), m/z=367.2 [M+H]$^+$.

Example 58: 1-isopropyl-5-[2-(methoxymethyl)-3-pyridyl]-N-[(3R)-tetrahydrofuran-3-yl]pyrazolo[4,3-b]pyridin-7-amine

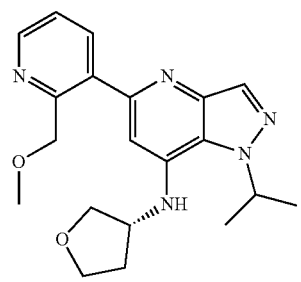 [SMILES: COCc1ncccc1-c1cc(N[C@@H]2CCOC2)c2c(cnn2C(C)C)n1]

Prepared using the same procedure as described for example 1, from 4,4,4',4',5,5,5',5'-octamethyl-2,2'-bi(1,3,2-dioxaborolane), 3-bromo-2-(methoxymethyl)pyridine and (R)-5-bromo-1-isopropyl-N-(tetrahydrofuran-3-yl)-1H-pyrazolo[4,3-b]pyridin-7-amine. $^1$H-NMR (400 MHz, DMSO-d$_6$): δ 8.60-8.59 (m, 1H), 8.12 (s, 1H), 7.95-7.93 (m, 1H), 7.47-7.44 (m, 1H), 6.78 (s, 1H), 6.23 (d, J=5.2 Hz, 1H), 5.30-5.23 (m, 1H), 4.59 (s, 2H), 4.30-4.22 (m, 1H), 4.02-3.98 (m, 1H), 3.91-3.89 (m, 1H), 3.78-3.75 (m, 2H), 3.22 (s, 3H), 2.31-2.26 (m, 1H), 2.04-1.99 (m, 1H), 1.47-1.44 (m, 6H). [α]° 2°=−10 (c=0.10, MeOH). LC-MS: tR=1.77 min (Method B), m/z=368.1 [M+H]$^+$.

Example 59: 5-(2-ethoxy-3-pyridyl)-1-isopropyl-3-methyl-pyrazolo[4,3-b]pyridine

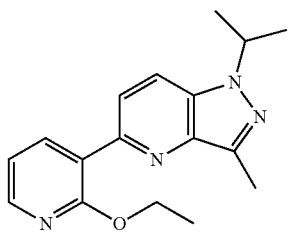 [SMILES: CCOc1ncccc1-c1ccc2c(n1)c(C)nn2C(C)C]

Prepared using the same procedure as described for example 1, from 2-ethoxy-3-(4,4,5,5-tetramethyl-1,3,2-dioxaborolan-2-yl)pyridine and 5-chloro-1-isopropyl-3-methyl-1H-pyrazolo[4,3-b]pyridine. $^1$H-NMR (400 MHz, Chloroform-d): 8.26-8.20 (m, 2H), 7.95 (d, J=9.2 Hz, 1H), 7.75 (d, J=9.2 Hz, 1H), 7.07-7.03 (m, 1H), 4.84-4.77 (m, 1H), 4.52-4.47 (m, 2H), 2.71 (s, 3H), 1.62 (d, J=2.4 Hz, 6H), 1.42 (t, J=7.2 Hz, 3H). LC-MS: tR=2.74 min (Method C), m/z=297.1 [M+H]$^+$.

Example 60: 1-isopropyl-3,6-dimethyl-5-phenyl-pyrazolo[4,3-b]pyridine

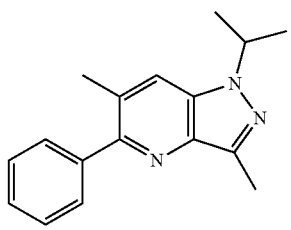 [SMILES: Cc1cc2c(nc1-c1ccccc1)c(C)nn2C(C)C]

Prepared using the same procedure as described for example 1, from phenylboronic acid and 5-chloro-1-isopropyl-3,6-dimethyl-1H-pyrazolo[4,3-b]pyridine. $^1$H-NMR (400 MHz, Chloroform-d): 7.59 (s, 1H), 7.54-7.52 (m, 2H), 7.49-7.45 (m, 2H), 7.40 (s, 1H), 4.81-4.74 (m, 1H), 2.68 (s, 3H), 2.44 (s, 3H), 1.61 (d, J=6.8 Hz, 6H). LC-MS: tR=2.31 min (Method A), m/z=266.1 [M+H]$^+$.

Example 61: 1-isopropyl-5-(2-methoxy-3-pyridyl)-3,6-dimethyl-pyrazolo[4,3-b]pyridine

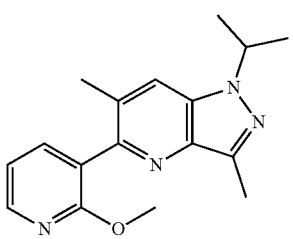 [SMILES: COc1ncccc1-c1nc2c(C)nn(C(C)C)c2cc1C]

Prepared using the same procedure as described for example 1, from (2-methoxy-3-pyridyl)boronic acid and 5-chloro-1-isopropyl-3,6-dimethyl-1H-pyrazolo[4,3-b]pyridine. $^1$H-NMR (400 MHz, Chloroform-d): 8.26-8.25 (m, 1H), 7.64 (dd, J=2.0 Hz, 7.2 Hz, 1H), 7.58 (s, 1H), 7.04 (dd, J=4.8 Hz, 7.2 Hz 1H), 4.82-4.72 (m, 1H), 3.93 (s, 3H), 2.67 (s, 3H), 2.29 (s, 3H), 1.61 (d, J=7.2 Hz, 6H). LC-MS: tR=2.38 min (Method C), m/z=297.1 [M+H]$^+$.

Example 62: 1-isopropyl-5-(2-methoxyphenyl)-3,6-dimethyl-pyrazolo[4,3-b]pyridine

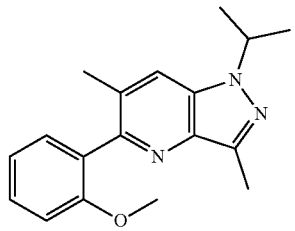 [SMILES: COc1ccccc1-c1nc2c(C)nn(C(C)C)c2cc1C]

Prepared using the same procedure as described for example 1, from (2-methoxyphenyl)boronic acid and 5-chloro-1-isopropyl-3,6-dimethyl-1H-pyrazolo[4,3-b]pyridine. $^1$H-NMR (400 MHz, Chloroform-d): 7.56 (s, 1H), 7.42-7.39 (m, 1H), 7.31-7.28 (m, 1H), 7.08-7.05 (m, 1H), 7.00-6.98 (m, 1H), 4.80-4.74 (m, 1H), 3.78 (s, 3H), 2.67 (s, 3H), 2.26 (s, 3H), 1.61 (d, J=6.8 Hz, 6H). LC-MS: tR=2.23 min (Method F), m/z=296.1 [M+H]$^+$.

Example 63: 5-(2-ethoxy-3-pyridyl)-1-isopropyl-3,6-dimethyl-pyrazolo[4,3-b]pyridine

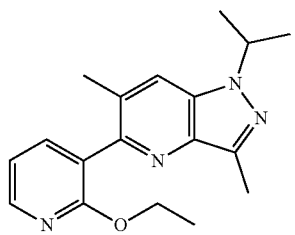 [SMILES: CCOc1ncccc1-c1nc2c(C)nn(C(C)C)c2cc1C]

Prepared using the same procedure as described for example 1, from (2-ethoxy-3-pyridyl)boronic acid and 5-chloro-1-isopropyl-3,6-dimethyl-1H-pyrazolo[4,3-b]pyridine. $^1$H-NMR (400 MHz, Chloroform-d): 8.23 (dd, J=2.0 Hz, 4.8 Hz, 1H), 7.64 (dd, J=2.0 Hz, 7.2 Hz, 1H), 7.57 (s, 1H), 7.01 (dd, J=4.8 Hz, 7.2 Hz 1H), 4.81-4.74 (m, 1H), 4.42-4.39 (m, 2H), 2.67 (s, 3H), 2.31 (s, 3H), 1.61 (d, J=7.2 Hz, 6H) 1.29 (t, J=7.2 Hz, 3H). LC-MS: tR=2.38 min (Method B), m/z=311.1 [M+H]$^+$.

Example 64: 1-isopropyl-3,6-dimethyl-5-(2-propoxy-3-pyridyl)pyrazolo[4,3-b]pyridine

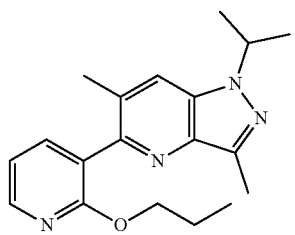 [SMILES: CCCOc1ncccc1-c1nc2c(C)nn(C(C)C)c2cc1C]

Prepared using the same procedure as described for example 1, from (2-propoxy-3-pyridyl)boronic acid and 5-chloro-1-isopropyl-3,6-dimethyl-1H-pyrazolo[4,3-b]pyridine. ¹H-NMR (400 MHz, CDCl₃): δ=8.23 (dd, J=1.8, 5.1 Hz, 1H), 7.63 (dd, J=1.9, 6.9 Hz, 1H), 7.56 (s, 1H), 7.03-6.98 (m, 1H), 4.77 (qt, J=6.8 Hz, 1H), 4.27 (br s, 2H), 2.67 (s, 3H), 2.31 (s, 3H), 1.72-1.64 (m, 2H), 1.61 (d, J=6.6 Hz, 6H), 0.88 (t, J=7.4 Hz, 3H). LC-MS: tR=2.87 min (Method C), m/z=325.1 [M+H]⁺.

Example 65: 5-(2-ethoxy-3-pyridyl)-1-isopropyl-N,3-dimethyl-pyrazolo[4,3-b]pyridin-7-amine

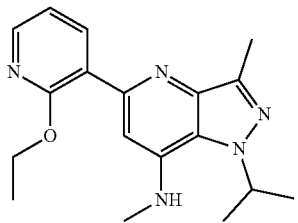 [SMILES: CCOc1ncccc1-c1cc(NC)c2c(n1)c(C)nn2C(C)C]

Prepared using the same procedure as described for example 1, from (2-ethoxy-3-pyridyl)boronic acid and 5-chloro-1-isopropyl-N,3-dimethyl-1H-pyrazolo[4,3-b]pyridin-7-amine. ¹H-NMR (400 MHz, Chloroform-d): δ 8.29-8.27 (m, 1H), 8.13-8.18 (m, 1H), 7.17 (s, 1H), 7.05-7.02 (m, 1H), 4.83 (brs, 1H), 4.52-4.47 (m, 3H), 3.07 (d, J=5.2 Hz, 3H), 2.65 (s, 3H), 1.62 (d, J=6.4 Hz, 6H), 1.45 (t, J=6.8 Hz, 3H). LC-MS: tR=1.74 min (Method A), m/z=326.1 [M+H]⁺.

Example 66: 5-(2-ethoxy-3-pyridyl)-N-ethyl-1-isopropyl-3-methyl-pyrazolo[4,3-b]pyridin-7-amine

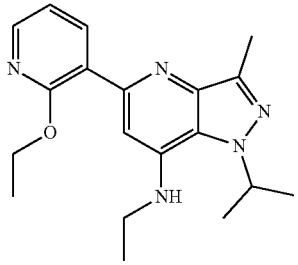 [SMILES: CCNc1cc(-c2cccnc2OCC)nc2c(C)nn(C(C)C)c12]

Prepared using the same procedure as described for example 1, from (2-ethoxy-3-pyridyl)boronic acid and 5-bromo-N-ethyl-1-isopropyl-3-methyl-1H-pyrazolo[4,3-b]pyridin-7-amine. ¹H-NMR (400 MHz, Chloroform-d): δ 8.27-8.25 (m, 1H), 8.18-8.16 (m, 1H), 7.14 (s, 1H), 7.04-7.01 (m, 1H), 4.86-4.78 (m, 1H), 4.51-4.45 (m, 2H), 4.36 (brs, 1H), 3.43-3.36 (m, 2H), 2.64 (s, 3H), 1.63 (d, J=6.4 Hz, 6H), 1.43 (t, J=7.2 Hz, 6H). LC-MS: tR=1.88 min (Method A), m/z=340.1 [M+H]⁺.

Example 67: (±)-5-[[[5-(2-ethoxy-3-pyridyl)-1-isopropyl-3-methyl-pyrazolo[4,3-b]pyridin-7-yl]amino]methyl]-1-methyl-pyrrolidin-2-one

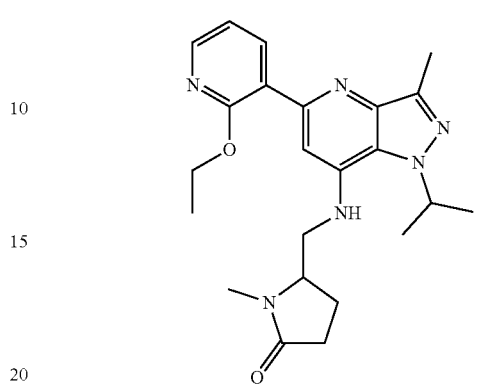

Prepared using the same procedure as described for example 1, from (2-ethoxy-3-pyridyl)boronic acid and (±)-5-(((5-chloro-1-isopropyl-3-methyl-1H-pyrazolo[4,3-b]pyridin-7-yl)amino)methyl)-1-methylpyrrolidin-2-one. ¹H-NMR (400 MHz, Chloroform-d): δ 8.26 (dd, J=1.6, 7.6 Hz, 1H), 8.19 (d, J=2.0, 4.8 Hz, 1H), 7.18 (s, 1H), 7.04 (dd, J=4.8, 7.2 Hz, 1H), 4.75-4.72 (m, 1H), 4.51-4.46 (m, 2H), 4.39 (brs, 1H), 4.00-3.99 (m, 1H), 3.57-3.50 (m, 2H), 2.94 (s, 3H), 2.64 (s, 3H), 2.53-2.51 (m, 2H), 2.49-2.32 (m, 1H), 2.03-2.02 (m, 1H), 1.62 (d, J=6.4 Hz, 6H), 1.40 (t, J=7.2 Hz, 3H). LC-MS: tR=1.94 min (Method C), m/z=423.1 [M+H]⁺.

Example 68: 4-[[[5-(2-ethoxy-3-pyridyl)-1-isopropyl-3-methyl-pyrazolo[4,3-b]pyridin-7-yl]amino]methyl]-1-methyl-pyrrolidin-2-one

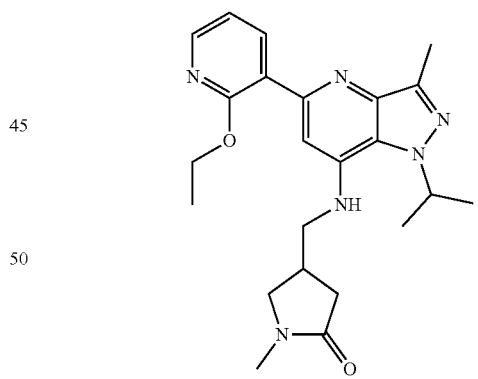

Prepared using the same procedure as described for example 1, from (2-ethoxy-3-pyridyl)boronic acid and (±)-4-(((5-chloro-1-isopropyl-3-methyl-1H-pyrazolo[4,3-b]pyridin-7-yl)amino)methyl)-1-methylpyrrolidin-2-one. ¹H-NMR (400 MHz, Chloroform-d): δ 8.27 (dd, J=2.0, 7.6 Hz, 1H), 8.19 (d, J=4.0 Hz, 1H), 7.15 (s, 1H), 7.05-7.03 (m, 1H), 4.86-4.83 (m, 1H), 4.49 (q, J=7.2 Hz, 2H), 3.62 (t, J=9.6 Hz, 1H), 3.45-3.41 (m, 2H), 3.30-3.26 (m, 1H), 2.95-2.80 (m, 4H), 2.72-2.64 (m, 4H), 2.34-2.29 (m, 1H), 1.62 (d, J=6.4 Hz, 6H), 1.42 (t, J=7.2 Hz, 3H). LC-MS: tR=2.03 min (Method B), m/z=423.1 [M+H]⁺.

Example 69: 5-(2-ethoxy-3-pyridyl)-1-isopropyl-3-methyl-pyrazolo[4,3-b]pyridin-7-amine

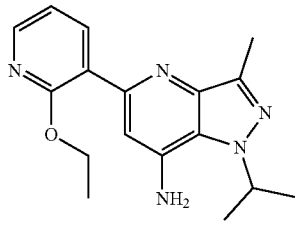 [SMILES: CCOc1ncccc1-c1cc(N)c2c(n1)c(C)nn2C(C)C]

A solution of 5-(2-ethoxypyridin-3-yl)-1-isopropyl-N-(4-methoxybenzyl)-3-methyl-1H-pyrazolo[4,3-b]pyridin-7-amine (1.25 g, 2.90 mmol) in TFA (15 mL) was stirred at 60° C. for 18 hours. The mixture was concentrated and the residue was dissolved in ethyl acetate (200 mL). The resulting mixture was washed with saturated aqueous NaHCO$_3$ (30 mL), brine (20 mL), dried over Na$_2$SO$_4$ and concentrated. The crude mixture was purified by flash chromatography with petroleum ether:ethyl acetate=3:1 to 2:1 to give 5-(2-ethoxy-3-pyridyl)-1-isopropyl-3-methyl-pyrazolo[4,3-b]pyridin-7-amine. $^1$H-NMR (400 MHz, Chloroform-d): δ 8.22 (dd, J=2.0, 7.2 Hz, 1H), 8.17 (dd, J=2.0, 4.8 Hz, 1H), 7.18 (s, 1H), 7.02 (dd, J=4.8, 7.2 Hz, 1H), 4.92-4.85 (m, 1H), 4.49 (q, J=7.2 Hz, 2H), 4.31 (brs, 2H), 2.65 (s, 3H), 1.64 (d, J=6.4 Hz 6H), 1.42 (t, J=7.2 Hz 3H). LC-MS: tR=1.91 min (Method C), m/z=312 [M+H]$^+$.

Example 70: 5-(2-ethoxy-3-pyridyl)-1-isopropyl-pyrazolo[4,3-b]pyridine

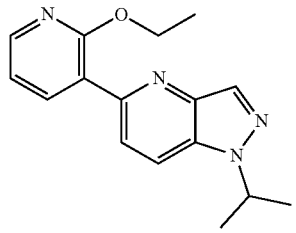 [SMILES: CCOc1ncccc1-c1ccc2c(cnn2C(C)C)n1]

To a solution of CuBr$_2$ (120 mg, 0.54 mmol) and isopentyl nitrite (63 mg, 0.54 mmol) in CH$_3$CN (10 mL) was added 5-(2-ethoxypyridin-3-yl)-1-isopropyl-1H-pyrazolo[4,3-b]pyridine (100 mg, 0.34 mmol) at 40° C. The mixture was stirred at 80° C. for 1 hour. The reaction mixture was concentrated under reduced pressure. The residue was purified by preparative-TLC (SiO$_2$, petroleum ether:ethyl acetate=5:1) and purified by flash silica gel chromatography (Eluent of 0~20% ethyl acetate/petroleum ether) to give 7-bromo-5-(2-ethoxypyridin-3-yl)-1-isopropyl-1H-pyrazolo[4,3-b]pyridine. To a solution of 7-bromo-5-(2-ethoxypyridin-3-yl)-1-isopropyl-1H-pyrazolo[4,3-b]pyridine (70 mg, 0.19 mmol) in ethyl acetate (7 mL) and MeOH (3 mL) was added Pd/C (7 mg). The mixture was stirred at 15° C. for 0.25 hours under H$_2$. The reaction mixture was filtered and was concentrated. The residue was purified by flash silica gel chromatography (Eluent of 0~25% ethyl acetate/petroleum ether) to give 5-(2-ethoxy-3-pyridyl)-1-isopropyl-pyrazolo[4,3-b]pyridine. $^1$H-NMR (400 MHz, Chloroform-d): δ 8.28 (s, 1H), 8.20 (t, J=4.4 Hz, 2H), 7.98 (d, J=8.4 Hz, 1H), 7.82 (d, J=9.2 Hz, 1H), 7.04 (t, J=6.8 Hz, 1H), 4.82-4.92 (m, 1H), 4.49 (q, J=6.8 Hz, 2H), 1.65 (s, 3H), 1.63 (s, 3H), 1.41 (t, J=7.2 Hz, 3H). LC-MS: tR=2.38 min (Method C), m/z=283.2 [M+H]$^+$.

Example 71: 2-(2-ethoxy-3-pyridyl)-6-isopropyl-3,8-dimethyl-imidazo[1,5-a]pyrimidine

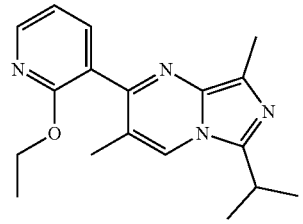 [SMILES: CCOc1ncccc1-c1nc2c(C)nc(C(C)C)n2cc1C]

2-Methoxy pyridine (96 mg, 93 μl, 0.882 mmol) was added to N-(1-(4-(2-ethoxypyridin-3-yl)-5-methylpyrimidin-2-yl)ethyl)isobutyramide (130 mg, 0.396 mmol) in dichloromethane (5.2 mL). Trifluoromethanesulfonic anhydride (139 μl, 0.827 mmol) was added slowly. The reaction mixture was stirred at 35° C. for 3 hours. The reaction was quenched with saturated aqueous NaHCO$_3$. The mixture was extracted with ethyl acetate. The organic phase was washed with brine, dried over MgSO$_4$ and concentrated in vacuo. The crude material was purified via flash chromatography on silica gel (etyl acetate/heptane) followed by purification by SFC to afford the title compound. $^1$H-NMR (600 MHz, DMSO-d$_6$): δ 8.42 (d, J=1.4 Hz, 1H), 8.27 (dd, J=5.0, 1.9 Hz, 1H), 7.71 (dd, J=7.2, 1.9 Hz, 1H), 7.11 (dd, J=7.2, 5.0 Hz, 1H), 4.48-4.29 (m, 2H), 3.41 (p, J=6.9 Hz, 1H), 2.38 (s, 3H), 1.99 (d, J=1.3 Hz, 3H), 1.31 (d, J=6.8 Hz, 6H), 1.24 (t, J=7.0 Hz, 3H). LC-MS: tR=0.51 min (Method D), m/z=311.3 [M+H]$^+$.

Example 72: 2-(2-ethoxy-3-pyridyl)-6-isopropyl-8-methyl-imidazo[1,5-a]pyrimidine

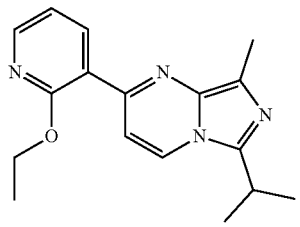 [SMILES: CCOc1ncccc1-c1ccn2c(C(C)C)nc(C)c2n1]

Prepared using the same procedure as described for example 71, from 1-(4-(2-Ethoxypyridin-3-yl)-5-methylpyrimidin-2-yl)ethanamine and isobutyric anhydride. $^1$H-NMR (600 MHz, Chloroform-d): δ 8.29 (dd, J=7.4, 2.0 Hz, 1H), 8.22 (dd, J=4.9, 2.0 Hz, 1H), 7.93 (d, J=7.6 Hz, 1H), 7.23 (d, J=7.6 Hz, 1H), 7.04 (dd, J=7.4, 4.9 Hz, 1H), 4.50 (q, J=7.1 Hz, 2H), 3.29 (hept, J=6.9 Hz, 1H), 2.63 (s, 3H), 1.52-1.39 (m, 9H). LC-MS: tR=0.48 min (Method E), m/z=297.3 [M+H]$^+$.

Example 73: 6-cyclobutyl-2-(2-ethoxy-3-pyridyl)-8-methyl-imidazo[1,5-a]pyrimidine

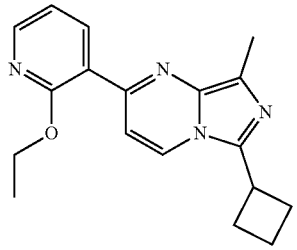 [SMILES: CCOc1ncccc1-c1ccn2c(C3CCC3)nc(C)c2n1]

Prepared using the same procedure as described for example 71, from 1-(4-(2-Ethoxypyridin-3-yl)-5-methylpyrimidin-2-yl)ethanamine and cyclobutanecarbonyl chloride (prepared from cyclobutanecarboxylic acid and oxalylchloride). $^1$H-NMR (600 MHz, Chloroform-d): δ 8.29 (dd, J=7.4, 2.0 Hz, 1H), 8.21 (dd, J=4.9, 2.0 Hz, 1H), 7.83 (d, J=7.6 Hz, 1H), 7.20 (d, J=7.6 Hz, 1H), 7.03 (dd, J=7.5, 4.9 Hz, 1H), 4.49 (q, J=7.0 Hz, 2H), 3.89-3.74 (m, 1H), 2.65 (s, 3H), 2.64-2.53 (m, 2H), 2.52-2.40 (m, 2H), 2.21-2.13 (m, 1H), 2.08-1.99 (m, 1H), 1.43 (t, J=7.1 Hz, 3H). LC-MS: tR=0.57 min (Method D), m/z=309.3 [M+H]$^+$.

Example 74: 6-cyclopropyl-2-(2-ethoxy-3-pyridyl)-8-methyl-imidazo[1,5-a]pyrimidine

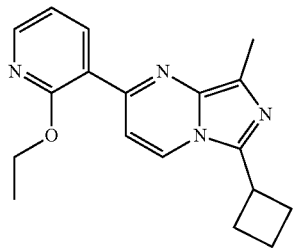 [SMILES: CCOc1ncccc1-c1ccn2c(C3CCC3)nc(C)c2n1]

Prepared using the same procedure as described for example 71, from 1-(4-(2-Ethoxypyridin-3-yl)-5-methylpyrimidin-2-yl)ethanamine and cyclopropanecarbonyl chloride (prepared from cyclopropanecarboxylic acid and oxalylchloride). $^1$H-NMR (600 MHz, Chloroform-d): δ 8.29 (dd, J=7.4, 2.0 Hz, 1H), 8.22 (dd, J=4.9, 2.0 Hz, 1H), 8.11 (d, J=7.6 Hz, 1H), 7.25 (d, J=7.6 Hz, 1H), 7.03 (dd, J=7.5, 4.9 Hz, 1H), 4.50 (q, J=7.1 Hz, 2H), 2.59 (s, 3H), 2.01 (tt, J=8.1, 5.6 Hz, 1H), 1.44 (t, J=7.0 Hz, 3H), 1.13-1.03 (m, 4H). LC-MS: tR=0.53 min (Method D), m/z=295.3 [M+H]$^+$.

Example 75: 2-(2-ethoxy-3-pyridyl)-6-(1-ethylpropyl)-8-methyl-imidazo[1,5-a]pyrimidine

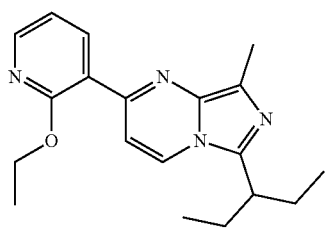 [SMILES: CCOc1ncccc1-c1ccn2c(C(CC)CC)nc(C)c2n1]

Prepared using the same procedure as described for example 71, from 1-(4-(2-Ethoxypyridin-3-yl)-5-methylpyrimidin-2-yl)ethanamine and 2-ethylbutanoyl chloride (prepared from 2-methylbutanoic acid and oxalylchloride). $^1$H-NMR (600 MHz, Chloroform-d): δ 8.31 (dd, J=7.4, 2.0 Hz, 1H), 8.21 (dd, J=4.9, 2.0 Hz, 1H), 7.97 (d, J=7.7 Hz, 1H), 7.21 (d, J=7.6 Hz, 1H), 7.04 (dd, J=7.4, 4.9 Hz, 1H), 4.51 (q, J=7.0 Hz, 2H), 2.86 (tt, J=8.8, 5.5 Hz, 1H), 2.64 (s, 3H), 1.98-1.89 (m, 2H), 1.88-1.76 (m, 2H), 1.44 (t, J=7.0 Hz, 3H), 0.83 (t, J=7.4 Hz, 6H). LC-MS: tR=0.59 min (Method D), m/z=311.3 [M+H]$^+$.

Example 76: (±)-2-(2-ethoxy-3-pyridyl)-8-methyl-6-sec-butyl-imidazo[1,5-a]pyrimidine

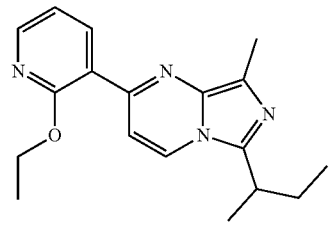

Prepared using the same procedure as described for example 71, from 1-(4-(2-Ethoxypyridin-3-yl)-5-methylpyrimidin-2-yl)ethanamine and 2-methylbutanoyl chloride (prepared from 2-ethylbutanoic acid and oxalylchloride). $^1$H-NMR (600 MHz, Chloroform-d): δ 8.30 (dd, J=7.4, 2.0 Hz, 1H), 8.21 (dd, J=4.9, 2.0 Hz, 1H), 7.94 (d, J=7.6 Hz, 1H), 7.21 (d, J=7.6 Hz, 1H), 7.04 (dd, J=7.4, 4.9 Hz, 1H), 4.50 (q, J=7.1 Hz, 2H), 3.06 (h, J=7.0 Hz, 1H), 2.63 (s, 3H), 1.95 (dt, J=13.5, 7.3 Hz, 1H), 1.77 (ddd, J=14.0, 7.5, 6.7 Hz, 1H), 1.50-1.39 (m, 6H), 0.91 (t, J=7.4 Hz, 3H). LC-MS: tR=0.63 min (Method D), m/z=325.3 [M+H]$^+$.

Example 77: 2-(2-ethoxy-3-pyridyl)-8-methyl-6-(3-methyloxetan-3-yl)imidazo[1,5-a]pyrimidine

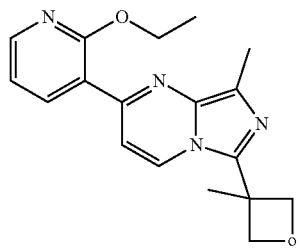

Prepared using the same procedure as described for example 71, from 1-(4-(2-Ethoxypyridin-3-yl)-5-methylpyrimidin-2-yl)ethanamine and 3-methyloxetane-3-carbonyl chloride (prepared from 3-methyloxetane-3-carboxylic acid and oxalylchloride). $^1$H-NMR (600 MHz, Chloroform-d): δ 8.33 (dd, J=7.5, 2.0 Hz, 1H), 8.23 (dd, J=4.9, 2.0 Hz, 1H), 8.05 (d, J=7.6 Hz, 1H), 7.30 (d, J=7.6 Hz, 1H), 7.05 (dd, J=7.4, 4.9 Hz, 1H), 5.23 (d, J=6.1 Hz, 2H), 4.82 (d, J=6.0 Hz, 2H), 4.51 (q, J=7.1 Hz, 2H), 2.64 (s, 3H), 1.90 (s, 3H), 1.45 (t, J=7.1 Hz, 3H). LC-MS: tR=0.51 min (Method D), m/z=325.3 [M+H]$^+$.

Example 78: 2-(2-ethoxy-3-pyridyl)-8-methyl-6-(2,2-trifluoroethyl)imidazo[1,5-a]pyrimidine

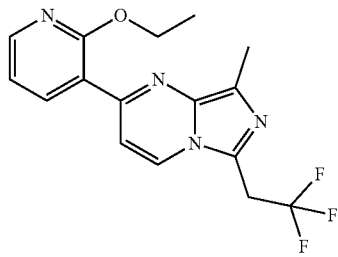 [SMILES: CCOc1ncccc1-c1ccn2c(CC(F)(F)F)nc(C)c2n1]

Prepared using the same procedure as described for example 71, from 1-(4-(2-Ethoxypyridin-3-yl)-5-methylpyrimidin-2-yl)ethanamine and 3,3,3-trifluoropropanoyl chloride (prepared from 3,3,3-trifluoropropanoic acid and oxalylchloride). $^1$H-NMR (500 MHz, Chloroform-d): δ 8.36 (dd, J=7.5, 2.0 Hz, 1H), 8.27 (dd, J=4.9, 2.0 Hz, 1H), 8.05 (d, J=7.6 Hz, 1H), 7.42 (d, J=7.7 Hz, 1H), 7.08 (dd, J=7.4, 4.9 Hz, 1H), 4.54 (q, J=7.1 Hz, 2H), 3.90 (q, J=10.0 Hz, 2H), 2.67 (s, 3H), 1.46 (t, J=7.1 Hz, 3H). LC-MS: tR=0.67 min (Method D), m/z=337.3 [M+H]$^+$.

Example 79: 2-(2-ethoxy-3-pyridyl)-8-methyl-6-(oxetan-3-yl)imidazo[1,5-a]pyrimidine

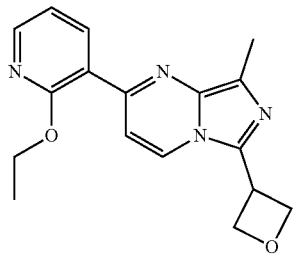 [SMILES: CCOc1ncccc1-c1ccn2c(C3COC3)nc(C)c2n1]

Prepared using the same procedure as described for example 71, from 1-(4-(2-Ethoxypyridin-3-yl)-5-methylpyrimidin-2-yl)ethanamine and oxetane-3-carbonyl chloride (prepared from oxetane-3-carboxylic acid and oxalylchloride). $^1$H-NMR (600 MHz, Chloroform-d): δ 8.32 (dd, J=7.4, 2.0 Hz, 1H), 8.23 (dd, J=4.9, 2.0 Hz, 1H), 8.09 (d, J=7.6 Hz, 1H), 7.31 (d, J=7.6 Hz, 1H), 7.05 (dd, J=7.5, 4.9 Hz, 1H), 5.19-5.10 (m, 4H), 4.62 (p, J=7.6 Hz, 1H), 4.50 (q, J=7.1 Hz, 2H), 2.65 (s, 3H), 1.44 (t, J=7.1 Hz, 3H). LC-MS: tR=0.56 min (Method J), m/z=311.3 [M+H]$^+$.

Example 80: 6-cyclopentyl-2-(2-ethoxy-3-pyridyl)-8-methyl-imidazo[1,5-a]pyrimidine

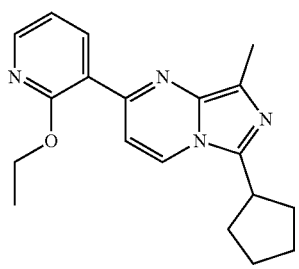 [SMILES: CCOc1ncccc1-c1ccn2c(C3CCCC3)nc(C)c2n1]

Prepared using the same procedure as described for example 71, from 1-(4-(2-Ethoxypyridin-3-yl)-5-methylpyrimidin-2-yl)ethanamine and cyclopentanecarbonyl chloride (prepared from cyclopentanecarboxylic acid and oxalylchloride) $^1$H-NMR (600 MHz, DMSO-d$_6$): δ 8.54 (d, J=7.6 Hz, 1H), 8.27 (dd, J=4.9, 2.0 Hz, 1H), 8.20 (dd, J=7.4, 2.0 Hz, 1H), 7.18 (d, J=7.6 Hz, 1H), 7.15 (dd, J=7.4, 4.9 Hz, 1H), 4.45 (q, J=7.0 Hz, 2H), 3.52 (p, J=8.1 Hz, 1H), 2.45 (s, 3H), 2.14-2.01 (m, 2H), 1.89-1.82 (m, 2H), 1.80-1.71 (m, 2H), 1.70-1.60 (m, 2H), 1.37 (t, J=7.0 Hz, 3H). LC-MS: tR=0.58 min (Method D), m/z=323.3 [M+H]$^+$.

Example 81: (±)-2-(2-ethoxy-3-pyridyl)-8-methyl-6-tetrahydrofuran-3-yl-imidazo[1,5-a]pyrimidine

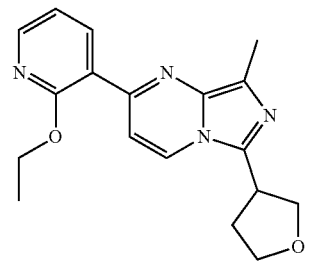 [SMILES: CCOc1ncccc1-c1ccn2c(C3CCOC3)nc(C)c2n1]

Prepared using the same procedure as described for example 71, from 1-(4-(2-Ethoxypyridin-3-yl)-5-methylpyrimidin-2-yl)ethanamine and (±)-tetrahydrofuran-3-carbonyl chloride (prepared from (±)-tetrahydrofuran-3-carboxylic acid and oxalylchloride). $^1$H-NMR (600 MHz, DMSO-d$_6$): δ 8.61 (d, J=7.6 Hz, 1H), 8.27 (dd, J=4.9, 2.0 Hz, 1H), 8.21 (dd, J=7.4, 2.0 Hz, 1H), 7.22 (d, J=7.6 Hz, 1H), 7.15 (dd, J=7.4, 4.9 Hz, 1H), 4.45 (q, J=7.0 Hz, 2H), 4.13 (t, J=7.7 Hz, 1H), 4.00-3.89 (m, 2H), 3.89-3.77 (m, 2H), 2.46 (s, 3H), 2.41-2.32 (m, 1H), 2.27-2.17 (m, 1H), 1.37 (t, J=7.0 Hz, 3H). LC-MS: tR=0.49 min (Method D), m/z=325.3 [M+H]$^+$.

Example 82: 6-tert-butyl-2-(2-ethoxy-3-pyridyl)-8-methyl-imidazo[1,5-a]pyrimidine

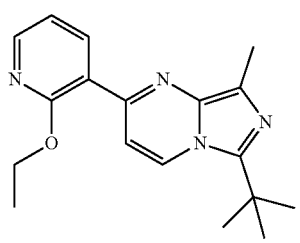 [SMILES: CCOc1ncccc1-c1ccn2c(C(C)(C)C)nc(C)c2n1]

Prepared using the same procedure as described for example 71, from 1-(4-(2-Ethoxypyridin-3-yl)-5-methylpyrimidin-2-yl)ethanamine and pivaloyl chloride. $^1$H-NMR (600 MHz, Chloroform-d): δ 8.32 (dd, J=7.5, 2.0 Hz, 1H), 8.25-8.15 (m, 2H), 7.21 (d, J=7.8 Hz, 1H), 7.03 (dd, J=7.4, 4.8 Hz, 1H), 4.51 (q, J=7.1 Hz, 2H), 2.63 (s, 3H), 1.45 (t, J=7.1 Hz, 3H), 1.25 (s, 9H). LC-MS: tR=0.55 min (Method D), m/z=311.6 [M+H]$^+$.

Example 83 and Example 84: 2-(2-ethoxy-3-pyridyl)-8-methyl-6-[1-methylpropyl]imidazo[1,5-a]pyrimidine, Enantiomer 1 and Enantiomer 2

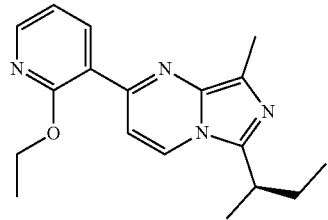

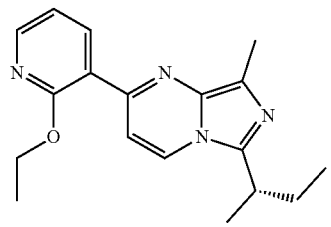

(±)-2-(2-ethoxy-3-pyridyl)-8-methyl-6-[1-methylpropyl]imidazo[1,5-a]pyrimidine was prepared using the same procedure as described for example 71, from 1-(4-(2-ethoxypyridin-3-yl)-5-methylpyrimidin-2-yl)ethanamine and (±)-2-methylbutanoyl chloride followed by separation by chiral SFC to afford 2-(2-ethoxy-3-pyridyl)-8-methyl-6-[1-methylpropyl]imidazo[1,5-a]pyrimidine, enantiomer 1 and enantiomer 2.

Example 83

2-(2-ethoxy-3-pyridyl)-8-methyl-6-[1-methylpropyl]imidazo[1,5-a]pyrimidine, enantiomer 1. $^1$H-NMR (400 MHz, Chloroform-d): δ 8.31 (dd, J=2.0, 7.6 Hz, 1H), 8.22 (d, J=2.0, 4.4 Hz, 1H), 7.94 (d, J=8.0 Hz, 1H), 7.22 (d, J=7.2 Hz, 1H), 7.04 (dd, J=4.8, 7.6 Hz, 1H), 4.51 (q, J=7.2 Hz, 2H), 3.09-3.04 (m, 1H), 2.64 (s, 3H), 2.00-1.93 (m, 1H), 1.80-1.76 (m, 1H), 1.46-1.43 (m, 6H), 0.92 (t, J=6.8 Hz, 3H). LC-MS: tR=2.38 min (Method F), m/z=311.1 [M+H]$^+$.

Example 84

2-(2-ethoxy-3-pyridyl)-8-methyl-6-[1-methylpropyl]imidazo[1,5-a]pyrimidine, enantiomer 2. $^1$H-NMR (400 MHz, Chloroform-d): δ 8.31 (dd, J=2.0, 7.6 Hz, 1H), 8.22 (dd, J=2.0, 4.8 Hz, 1H), 7.94 (d, J=8.0 Hz, 1H), 7.22 (d, J=7.2 Hz, 1H), 7.04 (dd, J=4.8, 7.6 Hz, 1H), 4.51 (q, J=7.2 Hz, 2H), 3.11-3.02 (m, 1H), 2.64 (s, 3H), 2.00-1.92 (m, 1H), 1.80-1.76 (m, 1H), 1.46-1.43 (m, 6H), 0.92 (t, J=7.6 Hz, 3H). LC-MS: tR=1.81 min (Method A), m/z=311.1 [M+H]$^+$.

Example 85: 5-(2-ethoxy-3-pyridyl)-7-[(3R)-3-methoxypyrrolidin-1-yl]-1-methyl-pyrazolo[4,3-b]pyridine

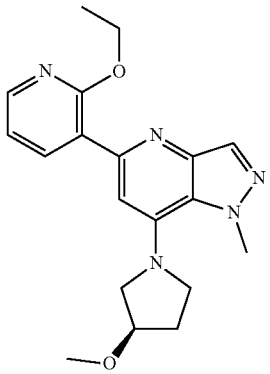 [SMILES: CCOc1ncccc1-c1cc(N2CC[C@@H](OC)C2)c2c(cnn2C)n1]

A mixture of 7-chloro-5-(2-ethoxypyridin-3-yl)-1-methyl-1H-pyrazolo[4,3-b]pyridine (0.35 mmol), (R)-3-methoxypyrrolidine (0.46 mmol) and N, N-diisopropylethylamine (0.46 mmol) in DMSO was stirred at 100° C. for 48 hours. After the reaction was complete, the mixture was cooled to room temperature and water (3 ml) was added. The solution was extracted with dichloromethane (3 ml). The dichloromethane solution was washed with water (2×4 mL), dried over Na$_2$SO$_4$ and concentrated in vacuo. The crude product was subjected to HPLC to give, 5-(2-ethoxy-3-pyridyl)-7-[(3R)-3-methoxypyrrolidin-1-yl]-1-methyl-pyrazolo[4,3-b]pyridine. $^1$H NMR (500 MHz, Chloroform-d): δ 8.02-8.32 (m, 3H), 7.46 (s, 1H), 7.02 (dd, J=7.1, 4.9 Hz, 1H), 4.47 (q, J=7.0 Hz, 2H), 4.26 (s, 3H), 4.14 (d, J=2.7 Hz, 1H), 3.50-3.62 (m, 1H), 3.47 (d, J=3.3 Hz, 2H), 3.14-3.42 (m, 4H), 2.25 (dt, J=13.6, 6.7 Hz, 1H), 1.97-2.18 (m, 1H), 1.43 (t, J=7.1 Hz, 3H). LC-MS: tR=0.43 min (Method E), m/z=354 [M+H]$^+$.

Example 86: 5-(2-ethoxy-3-pyridyl)-N-[(1R,2R)-2-methoxycyclopentyl]-1-methyl-pyrazolo[4,3-b]pyridin-7-amine

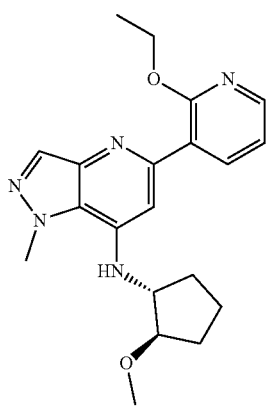 [SMILES: CCOc1ncccc1-c1cc(N[C@@H]2CCC[C@H]2OC)c2c(cnn2C)n1]

Prepared using the same procedure as described for example 85, from (1R,2R)-2-methoxycyclopentan-1-amine Example 87: (±)-5-(2-ethoxy-3-pyridyl)-7-(3-fluoro-3-methyl-pyrrolidin-1-yl)-1-methyl-pyrazolo[4,3-b]pyridine

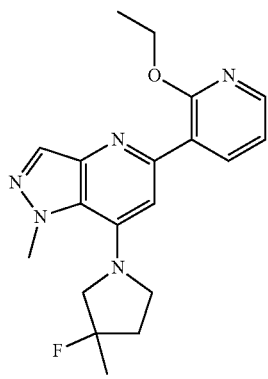 [SMILES: CCOc1ncccc1-c1cc(N2CCC(C)(F)C2)c2c(cnn2C)n1]

Prepared using the same procedure as described for example 85, from (±)-3-fluoro-3-methylpyrrolidine and 7-chloro-5-(2-ethoxypyridin-3-yl)-1-methyl-1H-pyrazolo[4,3-b]pyridine. LC-MS: tR=0.46 min (Method E), m/z=356.2 [M+H]+.

Example 88: 5-(2-ethoxy-3-pyridyl)-N-(3-methoxy-cyclopentyl)-1-methyl-pyrazolo[4,3-b]pyridin-7-amine

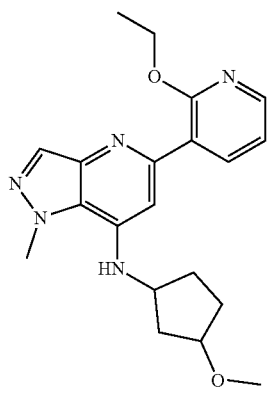 [SMILES: CCOc1ncccc1-c1cc(NC2CCC(OC)C2)c2c(cnn2C)n1]

Prepared using the same procedure as described for example 85, from (±)-3-methoxycyclopentan-1-amine and 7-chloro-5-(2-ethoxypyridin-3-yl)-1-methyl-1H-pyrazolo[4,3-b]pyridine. LC-MS: tR=0.47 min (Method E), m/z=368.2 [M+H]+.

In Vitro Testing
PDE1 Inhibition Assay

PDE1A, PDE1B and PDE1C assays were performed as follows: the assays were performed in 60 μL samples containing a fixed amount of the PDE1 enzyme (sufficient to convert 20-25% of the cyclic nucleotide substrate), a buffer (50 mM HEPES (4-(2-hydroxyethyl)-1-piperazineethane-sulfonic acid) pH 7.6; 10 mM MgCl$_2$; 0.02% Tween20), 0.1 mg/ml BSA (bovine serum albumin), 15 nM tritium labelled cAMP and varying amounts of inhibitors. Reactions were initiated by addition of the cyclic nucleotide substrate, and reactions were allowed to proceed for 1 hr at room temperature before being terminated through mixing with 20 μL (0.2 mg) yttrium silicate SPA beads (PerkinElmer). The beads were allowed to settle for 1 hour in the dark before the plates were counted in a Wallac 1450 Microbeta counter. The measured signals were converted to activity relative to an uninhibited control (100%) and IC$_{50}$ values were calculated using XlFit (model 205, IDBS).

The invention claimed is:
1. A compound according to formula (I)

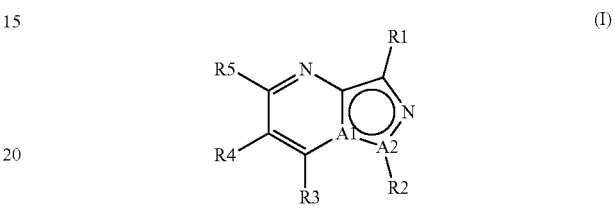

wherein
A1=C, A2=N and R3=-NR6R7
R1 is selected from the group consisting of hydrogen, linear or branched C$_{1-4}$ alkyl and C$_{3-4}$ cycloalkyl, wherein said linear or branched C$_{1-4}$ alkyl and C$_{3-4}$ cycloalkyl can optionally be substituted with one or more halogen;
R2 is selected from the group consisting of linear or branched C$_{1-6}$ alkyl, saturated monocyclic C$_{3-6}$ cycloalkyl, oxetanyl, tetrahydrofuranyl and tetrahydropyranyl, wherein said linear or branched C$_{1-6}$ alkyl and saturated monocyclic C$_{3-6}$ cycloalkyl can optionally be substituted with one or more halogen, and wherein said oxetanyl, tetrahydrofuranyl and tetrahydropyranyl can be optionally substituted one or more times with a substituent selected from methyl and halogen;
R4 is hydrogen;
R5 is a 5-6 membered heteroaryl which can be substituted one or more times with one or more substituents selected from C$_{1-4}$ alkoxy, —CH$_2$—C$_{1-4}$alkoxy, —CN, linear or branched C$_{1-4}$ alkyl and C$_{3-4}$ cycloalkyl, wherein said linear or branched C$_{1-4}$ alkyl, said C$_{3-4}$ cycloalkyl, said C$_{1-4}$ alkoxy and said —CH$_2$—C$_{1-4}$alkoxy can optionally be substituted with one or more halogen;
R6 is selected from the group consisting of hydrogen, linear or branched C$_{1-6}$ alkyl and C$_{3-6}$ cycloalkyl, wherein said linear or branched C$_{1-6}$ alkyl and C$_{3-6}$ cycloalkyl can be optionally substituted with one or more fluorine; and R7 is selected from the group consisting of hydrogen, linear or branched C$_{1-6}$ alkyl, C$_{3-6}$ cycloalkyl, oxetanyl, tetrahydrofuranyl, tetrahydropyranyl, —CH$_2$-oxetanyl, —CH$_2$-tetrahydrofuranyl, —CH$_2$-tetrahydropyranyl and —CH$_2$-pyrrolidinyl, wherein said linear or branched C$_{1-6}$ alkyl, C$_{3-6}$ cycloalkyl, oxetanyl, tetrahydrofuranyl, tetrahydropyranyl, —CH$_2$-oxetanyl, —CH$_2$-tetrahydrofuranyl, —CH$_2$-tetrahydropyranyl and CH$_2$-pyrrolidinyl-2-one can be optionally substituted with one or more substituents selected from methyl, methoxy, ethoxy, oxo and fluorine; or
R6 and R7 are connected to form a 5-7 membered saturated heterocyclic ring with the nitrogen atom to which they are attached and 4-6 carbon atoms; wherein said heterocyclic ring can be optionally substituted with one or more substituents selected from methoxy, methyl and fluorine;

or a pharmaceutically acceptable salt thereof.

2. The compound, or pharmaceutically acceptable salt thereof, according to claim 1, wherein R6 is hydrogen and R7 is selected from the group consisting of hydrogen, linear or branched $C_{1-6}$ alkyl, $C_{3-6}$ cycloalkyl, oxetanyl, tetrahydrofuranyl, tetrahydropyranyl, —CH$_2$-oxetanyl, —CH$_2$-tetrahydrofuranyl, —CH$_2$-tetrahydropyranyl and —CH$_2$-pyrrolidinyl, wherein said linear or branched $C_{1-6}$ alkyl, $C_{3-6}$ cycloalkyl, oxetanyl, tetrahydrofuranyl, tetrahydropyranyl, —CH$_2$-oxetanyl, —CH$_2$-tetrahydrofuranyl, —CH$_2$-tetrahydropyranyl and CH$_2$-pyrrolidinyl-2-one can be optionally substituted with one or more substituents selected from methyl, methoxy, ethoxy, oxo and fluorine.

3. The compound, or pharmaceutically acceptable salt thereof, according to claim 1, wherein R6 and R7 are connected to form a 5-7 membered saturated heterocyclic ring with the nitrogen atom to which they are attached and 4-6 carbon atoms; wherein said heterocyclic ring can be optionally substituted with one or more substituents selected from methoxy, methyl and fluorine.

4. The compound or pharmaceutically acceptable salt thereof according to claim 1, wherein R1 is selected from hydrogen and unsubstituted linear or branched $C_{1-4}$ alkyl.

5. The compound or pharmaceutically acceptable salt thereof according to claim 1, wherein R2 is selected from linear or branched $C_{1-6}$ alkyl, saturated monocyclic $C_{3-6}$ cycloalkyl; wherein said linear or branched $C_{1-6}$ alkyl and saturated monocyclic $C_{3-6}$ cycloalkyl can be optionally substituted with one or more halogen; or R2 is selected from the group consisting of oxetanyl, tetrahydrofuranyl and tetrahydropyranyl, all of which can be optionally substituted with a substituent selected from methyl and halogen.

6. The compound or pharmaceutically acceptable salt thereof according to claim 1, wherein R5 is a 6 membered heteroaryl selected from pyridyl and pyrimidyl.

7. The compound or pharmaceutically acceptable salt thereof according to claim 1, wherein the compound is selected from the group consisting of:

1: 5-(2-ethoxy-3-pyridyl)-1,3-dimethyl-7-pyrrolidin-1-yl-pyrazolo[4,3-b]pyridine;
2: 5-(2-ethoxy-3-pyridyl)-N,1-di(tetrahydrofuran-3-yl)pyrazolo[4,3-b]pyridin-7-amine;
3: (±)-5-(2-ethoxy-3-pyridyl)-7-pyrrolidin-1-yl-1-tetrahydrofuran-3-yl-pyrazolo[4,3-b]pyridine;
4: 5-(2-ethoxy-3-pyridyl)-1-(oxetan-3-yl)-7-pyrrolidin-1-yl-pyrazolo[4,3-b]pyridine;
5: (±)-5-(2-ethoxy-3-pyridyl)-1-(oxetan-3-yl)-N-tetrahydrofuran-3-yl-pyrazolo[4,3-b]pyridin-7-amine;
6: 5-(2-ethoxy-3-pyridyl)-1-isopropyl-N-[[(2S)-tetrahydrofuran-2-yl]methyl]pyrazolo[4,3-b]pyridin-7-amine;
7: 5-(2-ethoxy-3-pyridyl)-1-isopropyl-N-[[(2R)-tetrahydrofuran-2-yl]methyl]pyrazolo[4,3-b]pyridin-7-amine;
8: 5-(2-ethoxy-3-pyridyl)-1-isopropyl-N-[(3R)-tetrahydropyran-3-yl]pyrazolo[4,3-b]pyridin-7-amine;
9: 5-(2-ethoxy-3-pyridyl)-1-isopropyl-N-[(3S)-tetrahydropyran-3-yl]pyrazolo[4,3-b]pyridin-7-amine;
10: 5-(2-ethoxy-3-pyridyl)-1-isopropyl-N-tetrahydropyran-4-yl-pyrazolo[4,3-b]pyridin-7-amine;
11: 5-(2-ethoxy-3-pyridyl)-1-isopropyl-N-[trans-4-methoxytetrahydrofuran-3-yl]pyrazolo[4,3-b]pyridin-7-amine
12: 5-(2-ethoxy-3-pyridyl)-N,1-diisopropyl-pyrazolo[4,3-b]pyridin-7-amine;
13: 5-(2-ethoxy-3-pyridyl)-1-isopropyl-N-methyl-pyrazolo[4,3-b]pyridin-7-amine;
14: 5-(2-ethoxy-3-pyridyl)-1-methyl-7-pyrrolidin-1-yl-pyrazolo[4,3-b]pyridine;
16: 5-(2-ethoxy-3-pyridyl)-1-ethyl-7-pyrrolidin-1-yl-pyrazolo[4,3-b]pyridine;
17: 5-(2-ethoxy-3-pyridyl)-1-isopropyl-7-pyrrolidin-1-yl-pyrazolo[4,3-b]pyridine;
18: 5-(2-ethoxy-3-pyridyl)-1-propyl-7-pyrrolidin-1-yl-pyrazolo[4,3-b]pyridine,
19: 5-(2-ethoxy-3-pyridyl)-1-ethyl-N-[tetrahydrofuran-3-yl]pyrazolo[4,3-b]pyridin-7-amine, enantiomer 1,
20: 5-(2-ethoxy-3-pyridyl)-1-ethyl-N-[tetrahydrofuran-3-yl]pyrazolo[4,3-b]pyridin-7-amine, enantiomer 2;
21: 5-(2-ethoxy-3-pyridyl)-1-isopropyl-N-[tetrahydrofuran-3-yl]pyrazolo[4,3-b]pyridin-7-amine, enantiomer 1
22: 5-(2-ethoxy-3-pyridyl)-1-isopropyl-N-[tetrahydrofuran-3-yl]pyrazolo[4,3-b]pyridin-7-amine; enantiomer 2;
23: 5-(2-ethoxy-3-pyridyl)-1-propyl-N-[tetrahydrofuran-3-yl]pyrazolo[4,3-b]pyridin-7-amine, enantiomer 1;
24: 5-(2-ethoxy-3-pyridyl)-1-propyl-N-[tetrahydrofuran-3-yl]pyrazolo[4,3-b]pyridin-7-amine, enantiomer 2;
25: 1-isopropyl-5-(3-pyridyl)-N-[(3R)-tetrahydrofuran-3-yl]pyrazolo[4,3-b]pyridin-7-amine;
26: 1-isopropyl-5-pyrimidin-5-yl-N-[(3R)-tetrahydrofuran-3-yl]pyrazolo[4,3-b]pyridin-7-amine;
28: 1-isopropyl-5-(2-methoxy-3-pyridyl)-N-[(3R)-tetrahydrofuran-3-yl]pyrazolo[4,3-b]pyridin-7-amine;
29: 1-isopropyl-5-(2-methoxy-6-methyl-3-pyridyl)-N-[(3R)-tetrahydrofuran-3-yl]pyrazolo[4,3-b]pyridin-7-amine;
30: 1-isopropyl-5-(3-methoxy-4-pyridyl)-N-[(3R)-tetrahydrofuran-3-yl]pyrazolo[4,3-b]pyridin-7-amine;
31: 1-isopropyl-5-(4-methoxy-3-pyridyl)-N-[(3R)-tetrahydrofuran-3-yl]pyrazolo[4,3-b]pyridin-7-amine;
34: 5-(2-ethoxy-4-methyl-3-pyridyl)-1-isopropyl-N-[(3R)-tetrahydrofuran-3-yl]pyrazolo[4,3-b]pyridin-7-amine;
36: 5-(2-tert-butoxy-3-pyridyl)-1-isopropyl-N-[(3R)-tetrahydrofuran-3-yl]pyrazolo[4,3-b]pyridin-7-amine;
38: 5-(2,5-dimethoxy-4-pyridyl)-1-isopropyl-N-[(3R)-tetrahydrofuran-3-yl]pyrazolo[4,3-b]pyridin-7-amine;
39: 1-isopropyl-5-(3-methyl-2-pyridyl)-N-[(3R)-tetrahydrofuran-3-yl]pyrazolo[4,3-b]pyridin-7-amine;
40: 1-isopropyl-5-(3-methoxy-2-pyridyl)-N-[(3R)-tetrahydrofuran-3-yl]pyrazolo[4,3-b]pyridin-7-amine;
44: 5-[1-isopropyl-7-[[(3R)-tetrahydrofuran-3-yl]amino]pyrazolo[4,3-b]pyridin-5-yl]pyridine-3-carbonitrile;
46: 5-(5-ethoxy-3-pyridyl)-1-isopropyl-N-[(3R)-tetrahydrofuran-3-yl]pyrazolo[4,3-b]pyridin-7-amine;
47: 1-isopropyl-5-(5-methoxy-3-pyridyl)-N-[(3R)-tetrahydrofuran-3-yl]pyrazolo[4,3-b]pyridin-7-amine;
49: 1-isopropyl-5-(4-methoxypyrimidin-5-yl)-N-[(3R)-tetrahydrofuran-3-yl]pyrazolo[4,3-b]pyridin-7-amine;
50: 5-(4-ethoxypyrimidin-5-yl)-1-isopropyl-N-[(3R)-tetrahydrofuran-3-yl]pyrazolo[4,3-b]pyridin-7-amine;
51: 1-isopropyl-5-(5-methoxy-2-methyl-3-pyridyl)-N-[(3R)-tetrahydrofuran-3-yl]pyrazolo[4,3-b]pyridin-7-amine;
52: 1-isopropyl-5-(2-methoxy-5-methyl-3-pyridyl)-N-[(3R)-tetrahydrofuran-3-yl]pyrazolo[4,3-b]pyridin-7-amine;
54: 5-[1-isopropyl-7-[[(3R)-tetrahydrofuran-3-yl]amino]pyrazolo[4,3-b]pyridin-5-yl]-6-methoxy-pyridine-3-carbonitrile;

55: 6-ethoxy-5-[1-isopropyl-7-[[(3R)-tetrahydrofuran-3-yl]amino]pyrazolo[4,3-b]pyridin-5-yl]pyridine-3-carbonitrile;
56: 5-(2-ethyl-3-pyridyl)-1-isopropyl-N-[(3R)-tetrahydrofuran-3-yl]pyrazolo[4,3-b]pyridin-7-amine;
58: 1-isopropyl-5-[2-(methoxymethyl)-3-pyridyl]-N-[(3R)-tetrahydrofuran-3-yl]pyrazolo[4,3-b]pyridin-7-amine;
65: 5-(2-ethoxy-3-pyridyl)-1-isopropyl-N,3-dimethyl-pyrazolo[4,3-b]pyridin-7-amine;
66: 5-(2-ethoxy-3-pyridyl)-N-ethyl-1-isopropyl-3-methyl-pyrazolo[4,3-b]pyridin-7-amine;
67: (±)-5-[[[5-(2-ethoxy-3-pyridyl)-1-isopropyl-3-methyl-pyrazolo[4,3-b]pyridin-7-yl]amino]methyl]-1-methyl-pyrrolidin-2-one;
68: 4-[[[5-(2-ethoxy-3-pyridyl)-1-isopropyl-3-methyl-pyrazolo[4,3-b]pyridin-7-yl]amino]methyl]-1-methyl-pyrrolidin-2-one;
69: 5-(2-ethoxy-3-pyridyl)-1-isopropyl-3-methyl-pyrazolo[4,3-b]pyridin-7-amine;
85: 5-(2-ethoxy-3-pyridyl)-7-[(3R)-3-methoxypyrrolidin-1-yl]-1-methyl-pyrazolo[4,3-b]pyridine;
86: 5-(2-ethoxy-3-pyridyl)-N-[(1R,2R)-2-methoxycyclopentyl]-1-methyl-pyrazolo[4,3-b]pyridin-7-amine;
87: (±)-5-(2-ethoxy-3-pyridyl)-7-(3-fluoro-3-methyl-pyrrolidin-1-yl)-1-methyl-pyrazolo[4,3-b]pyridine; and
88: 5-(2-ethoxy-3-pyridyl)-N-(3-methoxycyclopentyl)-1-methyl-pyrazolo[4,3-b]pyridin-7-amine;

or a pharmaceutically acceptable salt of any of these compounds.

8. A pharmaceutical composition comprising a therapeutically effective amount of the compound of claim 1 or a pharmaceutically acceptable salt thereof, and one or more pharmaceutically acceptable carriers, diluents and/or excipients.

9. The pharmaceutical composition of claim 8, comprising the therapeutically effective amount of the compound, or a pharmaceutically acceptable salt thereof, and the one or more pharmaceutically acceptable carriers, diluents and/or excipients, wherein the compound is selected from the group consisting of:

1: 5-(2-ethoxy-3-pyridyl)-1,3-dimethyl-7-pyrrolidin-1-yl-pyrazolo[4,3-b]pyridine;
2: 5-(2-ethoxy-3-pyridyl)-N,1-di(tetrahydrofuran-3-yl)pyrazolo[4,3-b]pyridin-7-amine;
3: (±)-5-(2-ethoxy-3-pyridyl)-7-pyrrolidin-1-yl-1-tetrahydrofuran-3-yl-pyrazolo[4,3-b]pyridine;
4: 5-(2-ethoxy-3-pyridyl)-1-(oxetan-3-yl)-7-pyrrolidin-1-yl-pyrazolo[4,3-b]pyridine;
5: (±)-5-(2-ethoxy-3-pyridyl)-1-(oxetan-3-yl)-N-tetrahydrofuran-3-yl-pyrazolo[4,3-b]pyridin-7-amine;
6: 5-(2-ethoxy-3-pyridyl)-1-isopropyl-N-[[(2S)-tetrahydrofuran-2-yl]methyl]pyrazolo[4,3-b]pyridin-7-amine;
7: 5-(2-ethoxy-3-pyridyl)-1-isopropyl-N-[[(2R)-tetrahydrofuran-2-yl]methyl]pyrazolo[4,3-b]pyridin-7-amine;
8: 5-(2-ethoxy-3-pyridyl)-1-isopropyl-N-[(3R)-tetrahydropyran-3-yl]pyrazolo[4,3-b]pyridin-7-amine;
9: 5-(2-ethoxy-3-pyridyl)-1-isopropyl-N-[(3S)-tetrahydropyran-3-yl]pyrazolo[4,3-b]pyridin-7-amine;
10: 5-(2-ethoxy-3-pyridyl)-1-isopropyl-N-tetrahydropyran-4-yl-pyrazolo[4,3-b]pyridin-7-amine;
11: 5-(2-ethoxy-3-pyridyl)-1-isopropyl-N-[trans-4-methoxytetrahydrofuran-3-yl]pyrazolo[4,3-b]pyridin-7-amine
12: 5-(2-ethoxy-3-pyridyl)-N,1-diisopropyl-pyrazolo[4,3-b]pyridin-7-amine;
13: 5-(2-ethoxy-3-pyridyl)-1-isopropyl-N-methyl-pyrazolo[4,3-b]pyridin-7-amine;
14: 5-(2-ethoxy-3-pyridyl)-1-methyl-7-pyrrolidin-1-yl-pyrazolo[4,3-b]pyridine;
16: 5-(2-ethoxy-3-pyridyl)-1-ethyl-7-pyrrolidin-1-yl-pyrazolo[4,3-b]pyridine;
17: 5-(2-ethoxy-3-pyridyl)-1-isopropyl-7-pyrrolidin-1-yl-pyrazolo[4,3-b]pyridine;
18: 5-(2-ethoxy-3-pyridyl)-1-propyl-7-pyrrolidin-1-yl-pyrazolo[4,3-b]pyridine,
19: 5-(2-ethoxy-3-pyridyl)-1-ethyl-N-[tetrahydrofuran-3-yl]pyrazolo[4,3-b]pyridin-7-amine, enantiomer 1,
20: 5-(2-ethoxy-3-pyridyl)-1-ethyl-N-[tetrahydrofuran-3-yl]pyrazolo[4,3-b]pyridin-7-amine, enantiomer 2;
21: 5-(2-ethoxy-3-pyridyl)-1-isopropyl-N-[tetrahydrofuran-3-yl]pyrazolo[4,3-b]pyridin-7-amine, enantiomer 1
22: 5-(2-ethoxy-3-pyridyl)-1-isopropyl-N-[tetrahydrofuran-3-yl]pyrazolo[4,3-b]pyridin-7-amine; enantiomer 2;
23: 5-(2-ethoxy-3-pyridyl)-1-propyl-N-[tetrahydrofuran-3-yl]pyrazolo[4,3-b]pyridin-7-amine, enantiomer 1;
24: 5-(2-ethoxy-3-pyridyl)-1-propyl-N-[tetrahydrofuran-3-yl]pyrazolo[4,3-b]pyridin-7-amine, enantiomer 2;
25: 1-isopropyl-5-(3-pyridyl)-N-[(3R)-tetrahydrofuran-3-yl]pyrazolo[4,3-b]pyridin-7-amine;
26: 1-isopropyl-5-pyrimidin-5-yl-N-[(3R)-tetrahydrofuran-3-yl]pyrazolo[4,3-b]pyridin-7-amine;
28: 1-isopropyl-5-(2-methoxy-3-pyridyl)-N-[(3R)-tetrahydrofuran-3-yl]pyrazolo[4,3-b]pyridin-7-amine;
29: 1-isopropyl-5-(2-methoxy-6-methyl-3-pyridyl)-N-[(3R)-tetrahydrofuran-3-yl]pyrazolo[4,3-b]pyridin-7-amine;
30: 1-isopropyl-5-(3-methoxy-4-pyridyl)-N-[(3R)-tetrahydrofuran-3-yl]pyrazolo[4,3-b]pyridin-7-amine;
31: 1-isopropyl-5-(4-methoxy-3-pyridyl)-N-[(3R)-tetrahydrofuran-3-yl]pyrazolo[4,3-b]pyridin-7-amine;
34: 5-(2-ethoxy-4-methyl-3-pyridyl)-1-isopropyl-N-[(3R)-tetrahydrofuran-3-yl]pyrazolo[4,3-b]pyridin-7-amine;
36: 5-(2-tert-butoxy-3-pyridyl)-1-isopropyl-N-[(3R)-tetrahydrofuran-3-yl]pyrazolo[4,3-b]pyridin-7-amine;
38: 5-(2,5-dimethoxy-4-pyridyl)-1-isopropyl-N-[(3R)-tetrahydrofuran-3-yl]pyrazolo[4,3-b]pyridin-7-amine;
39: 1-isopropyl-5-(3-methyl-2-pyridyl)-N-[(3R)-tetrahydrofuran-3-yl]pyrazolo[4,3-b]pyridin-7-amine;
40: 1-isopropyl-5-(3-methoxy-2-pyridyl)-N-[(3R)-tetrahydrofuran-3-yl]pyrazolo[4,3-b]pyridin-7-amine;
44: 5-[1-isopropyl-7-[[(3R)-tetrahydrofuran-3-yl]amino]pyrazolo[4,3-b]pyridin-5-yl]pyridine-3-carbonitrile;
46: 5-(5-ethoxy-3-pyridyl)-1-isopropyl-N-[(3R)-tetrahydrofuran-3-yl]pyrazolo[4,3-b]pyridin-7-amine;
47: 1-isopropyl-5-(5-methoxy-3-pyridyl)-N-[(3R)-tetrahydrofuran-3-yl]pyrazolo[4,3-b]pyridin-7-amine;
49: 1-isopropyl-5-(4-methoxypyrimidin-5-yl)-N-[(3R)-tetrahydrofuran-3-yl]pyrazolo[4,3-b]pyridin-7-amine;
50: 5-(4-ethoxypyrimidin-5-yl)-1-isopropyl-N-[(3R)-tetrahydrofuran-3-yl]pyrazolo[4,3-b]pyridin-7-amine;
51: 1-isopropyl-5-(5-methoxy-2-methyl-3-pyridyl)-N-[(3R)-tetrahydrofuran-3-yl]pyrazolo[4,3-b]pyridin-7-amine;
52: 1-isopropyl-5-(2-methoxy-5-methyl-3-pyridyl)-N-[(3R)-tetrahydrofuran-3-yl]pyrazolo[4,3-b]pyridin-7-amine;
54: 5-[1-isopropyl-7-[[(3R)-tetrahydrofuran-3-yl]amino]pyrazolo[4,3-b]pyridin-5-yl]-6-methoxy-pyridine-3-carbonitrile;

55: 6-ethoxy-5-[1-isopropyl-7-[[(3R)-tetrahydrofuran-3-yl]amino]pyrazolo[4,3-b]pyridin-5-yl]pyridine-3-carbonitrile;
56: 5-(2-ethyl-3-pyridyl)-1-isopropyl-N-[(3R)-tetrahydrofuran-3-yl]pyrazolo[4,3-b]pyridin-7-amine;
58: 1-isopropyl-5-[2-(methoxymethyl)-3-pyridyl]-N-[(3R)-tetrahydrofuran-3-yl]pyrazolo[4,3-b]pyridin-7-amine;
65: 5-(2-ethoxy-3-pyridyl)-1-isopropyl-N,3-dimethyl-pyrazolo[4,3-b]pyridin-7-amine;
66: 5-(2-ethoxy-3-pyridyl)-N-ethyl-1-isopropyl-3-methyl-pyrazolo[4,3-b]pyridin-7-amine;
67: (±)-5-[[[5-(2-ethoxy-3-pyridyl)-1-isopropyl-3-methyl-pyrazolo[4,3-b]pyridin-7-yl]amino]methyl]-1-methyl-pyrrolidin-2-one;
68: 4-[[[5-(2-ethoxy-3-pyridyl)-1-isopropyl-3-methyl-pyrazolo[4,3-b]pyridin-7-yl]amino]methyl]-1-methyl-pyrrolidin-2-one;
69: 5-(2-ethoxy-3-pyridyl)-1-isopropyl-3-methyl-pyrazolo[4,3-b]pyridin-7-amine;
85: 5-(2-ethoxy-3-pyridyl)-7-[(3R)-3-methoxypyrrolidin-1-yl]-1-methyl-pyrazolo[4,3-b]pyridine;
86: 5-(2-ethoxy-3-pyridyl)-N-[(1R,2R)-2-methoxycyclopentyl]-1-methyl-pyrazolo[4,3-b]pyridin-7-amine;
87: (±)-5-(2-ethoxy-3-pyridyl)-7-(3-fluoro-3-methyl-pyrrolidin-1-yl)-1-methyl-pyrazolo[4,3-b]pyridine; and
88: 5-(2-ethoxy-3-pyridyl)-N-(3-methoxycyclopentyl)-1-methyl-pyrazolo[4,3-b]pyridin-7-amine.

\* \* \* \* \*